US011311774B2

(12) United States Patent
Choi et al.

(10) Patent No.: US 11,311,774 B2
(45) Date of Patent: Apr. 26, 2022

(54) ELECTRONIC DEVICE AND METHOD OF PROCESSING EXERCISE INFORMATION BY ELECTRONIC DEVICE

(71) Applicant: Samsung Electronics Co., Ltd., Suwon-si (KR)

(72) Inventors: Hyeeun Choi, Suwon-si (KR); Daesung Cho, Suwon-si (KR); Minhwan Jo, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/914,963

(22) Filed: Jun. 29, 2020

(65) Prior Publication Data

US 2021/0060384 A1 Mar. 4, 2021

(30) Foreign Application Priority Data

Aug. 30, 2019 (KR) .................. 10-2019-0107670

(51) Int. Cl.
*A63B 71/00* (2006.01)
*A63B 24/00* (2006.01)
*A63B 71/06* (2006.01)

(52) U.S. Cl.
CPC ...... *A63B 24/0062* (2013.01); *A63B 71/0622* (2013.01); *A63B 2220/70* (2013.01); *A63B 2225/50* (2013.01)

(58) Field of Classification Search
CPC .................. A63B 24/0062; A63B 2024/0065
See application file for complete search history.

(56) References Cited

U.S. PATENT DOCUMENTS 7,062,225 B2 * 6/2006 White ............... H04M 1/72412
 455/41.2
7,556,590 B2 * 7/2009 Watterson .......... A63B 24/0084
 482/8

(Continued)

FOREIGN PATENT DOCUMENTS

CN 104883596 A 9/2015
CN 105183152 A 12/2015
(Continued)

OTHER PUBLICATIONS

Rushil Khurana et al., GymCam: Detecting, Recognizing and Tracking Simultaneous Exercises in Unconstrained Scenes, Dec. 27, 2018, pp. 1-17, Proceedings of the ACM on Interactive, Mobile, Wearable and Ubiquitous Technologies, vol. 2, No. 4, Article 185, XP058423743.

(Continued)

*Primary Examiner* — Alvin A Hunter
(74) *Attorney, Agent, or Firm* — Jefferson IP Law, LLP

(57) ABSTRACT

An electronic device and a method of processing exercise information by an electronic device are provided. The electronic device includes at least one communication module, a display, at least one sensor, and a processor. The processor may perform control to make a connection with at least one external electronic device through the communication module, identify first exercise-related information measured during a first time interval, based on information received from the at least one external electronic device, identify second exercise-related information measured during a second time interval after the first time interval, based on information received from the at least one external electronic device, and when it is determined that the identified first exercise-related information and the identified second exercise-related information are information on a correlated exercise, based on a configured reference, display the first (Continued)

exercise-related information and the second exercise-related information as one continuous exercise through the display.

21 Claims, 48 Drawing Sheets

(56) References Cited

U.S. PATENT DOCUMENTS

| | | | |
|---|---|---|---|
| 7,695,406 B2* | 4/2010 | Waters | A63F 13/10 482/8 |
| 7,766,794 B2* | 8/2010 | Oliver | A63B 24/0062 482/8 |
| 8,839,155 B2 | 9/2014 | Ording | |
| 9,009,516 B1 | 4/2015 | Gabayan et al. | |
| 9,089,733 B2* | 7/2015 | Fisbein | A63B 22/00 |
| 9,778,280 B2 | 10/2017 | Yuen et al. | |
| 9,940,682 B2 | 4/2018 | Hoffman et al. | |
| 10,275,200 B2 | 4/2019 | Kang et al. | |
| 10,926,137 B2* | 2/2021 | Quast | G06K 9/00342 |
| 2009/0149299 A1 | 6/2009 | Tchao et al. | |
| 2015/0057944 A1 | 2/2015 | White et al. | |
| 2017/0046503 A1 | 2/2017 | Cho et al. | |
| 2017/0239525 A1 | 8/2017 | Kim et al. | |
| 2017/0353845 A1 | 12/2017 | Jeong et al. | |
| 2018/0064397 A1 | 3/2018 | Horikawa et al. | |
| 2018/0193695 A1 | 7/2018 | Lee | |
| 2018/0345077 A1 | 12/2018 | Blahnik et al. | |
| 2019/0008394 A1 | 1/2019 | Rao et al. | |

FOREIGN PATENT DOCUMENTS

| | | |
|---|---|---|
| CN | 105706095 A | 6/2016 |
| CN | 106030446 A | 10/2016 |
| CN | 106469250 A | 3/2017 |
| CN | 106934750 A | 7/2017 |
| CN | 108378484 A | 8/2018 |
| CN | 109196546 A | 1/2019 |
| CN | 109769011 A | 5/2019 |
| JP | 4456416 B2 | 4/2010 |
| JP | 2011-508615 A | 3/2011 |
| JP | 2017-124086 A | 7/2017 |
| KR | 10-2017-0099259 A | 8/2017 |
| KR | 10-2017-0111508 A | 10/2017 |
| KR | 10-1856058 B1 | 5/2018 |
| KR | 10-2018-0100753 A | 9/2018 |
| KR | 10-1931724 B1 | 3/2019 |

OTHER PUBLICATIONS

International Search Report dated Nov. 24, 2020, issued in International Application No. PCT/KR2020/010820.
European Search Report dated Jan. 14, 2021, issued in European Application No. 20193311.6.
Chinese Office Action dated Jul. 20, 2021, issued in Chinese Patent Application No. 202010876841.4.
Chinese Office Action dated Oct. 15, 2021, issued in Chinese Patent Application No. 202010876841.4.

* cited by examiner

|  | Treadmill | 7:26 ~ 7:56 |
|  | Weight machines | 8:06 ~ 8:11 |
|  | Arm curls | 8:16 ~ 8:21 |
|  | Exercise bike | 8:21 ~ 8:41 |
FIG.30

ELECTRONIC DEVICE AND METHOD OF PROCESSING EXERCISE INFORMATION BY ELECTRONIC DEVICE

CROSS-REFERENCE TO RELATED APPLICATION(S)

This application is based on and claims priority under 35 U.S.C. § 119(a) of a Korean patent application number 10-2019-0107670, filed on Aug. 30, 2019, in the Korean Intellectual Property Office, the disclosure of which is incorporated by reference herein in its entirety.

BACKGROUND

1. Field

The disclosure relates to an electronic device and a method of processing exercise information by an electronic device.

2. Description of Related Art

Recently, as interest in health increases, electronic devices provide various health-related functions for measuring and processing user exercise information. For example, an electronic device which can be worn on at least a part of a user's body may sense information according to movement of the user's body. The electronic device may include a three-axis acceleration sensor, a sensor for sensing motion information such as a gyro sensor, and a location measurement device such as a Global Positioning System (GPS) module. Accordingly, the electronic device may provide motion information identified according to movement of the user's body and/or exercise information of the user on the basis of location information identified through a GPS module.

The above information is presented as background information only to assist with an understanding of the disclosure. No determination has been made, and no assertion is made, as to whether any of the above might be applicable as prior art with regard to the disclosure.

SUMMARY

When an amount of exercise is measured through an electronic device, the electronic device may operate in a manual mode in which a user directly selects an exercise type and measures the amount of exercise or in an automatic mode in which an exercise type is automatically recognized on the basis of movement determined by various sensors included in the electronic device and the amount of exercise is measured.

For example, when the user exercises within a specific facility (for example, a fitness club or a gymnasium (GYM)) having various exercise machine, an amount of exercise is measured using only sensors included in the electronic device even though there is an accurate value set or measured by each exercise machine, and thus a relatively inaccurate exercise result may be recorded. In another example, when the user walks for exercise, if the user walks for exercise without using any exercise machine and then continuously walks for exercise using an exercise machine (for example, a treadmill), it may be difficult to determine the amount of exercise according to the exercise type since the exercise is processed as separate exercises.

Aspects of the disclosure are to address at least the above-mentioned problems and/or disadvantages and to provide at least the advantages described below. Accordingly, an aspect of the disclosure is to provide an electronic device capable of providing accurate exercise information for each exercise type by measuring exercise-related information on the basis of accurate data through a link between the electronic device and an exercise machine, and a method of processing exercise information by the electronic device.

Another aspect of the disclosure is to provide an electronic device capable of providing an accurate amount of exercise for each exercise type by connecting the electronic device and an exercise machine and merging the same type of continuous exercises, and a method of processing exercise information by the electronic dev ice.

Additional aspects will be set forth in part in the description which follows and, in part, will be apparent from the description, or may be learned by practice of the presented embodiments.

In accordance with an aspect of the disclosure, an electronic device is provided. The electronic device includes at least one communication module, a display, a processor operatively connected to the at least one communication module and the display, and a memory operatively connected to the processor, wherein the memory stores instructions causing the processor to, when executed, make a connection with at least one external electronic device through the at least one communication module, identify first exercise-related information measured during a first time interval, based on information received from the at least one external electronic device, identify second exercise-related information measured during a second time interval after the first time interval, based on information received from the at least one external electronic device, and when it is determined that the identified first exercise-related information and the identified second exercise-related information are information on a correlated exercise, based on a configured reference, display the first exercise-related information and the second exercise-related information as one continuous exercise through the display.

In accordance with another aspect of the disclosure, an electronic device is provided. The electronic device includes at least one communication module, a display, at least one sensor, a processor operatively connected to the at least one communication module, the display, and the at least one sensor, and a memory operatively connected to the processor, wherein the memory causes the processor to, when executed, store first exercise-related information in the memory, based on information measured during a first time interval by the at least one sensor, make a connection with at least one external electronic device through the at least one communication module, identify second exercise-related information measured during a second time interval after the first time interval, based on information received from the at least one external electronic device, and when it is determined that the stored first exercise-related information and the identified second exercise-related information are information on a correlated exercise, based on a configured reference, display the first exercise-related information and the second exercise-related information as one continuous exercise through the display.

In accordance with another aspect of the disclosure, an electronic device is provided. The electronic device includes at least one communication module, a display, at least one sensor, a processor operatively connected to the at least one communication module, the display, and the at least one sensor, and a memory operatively connected to the processor, wherein the memory causes the processor to, when executed, make a connection with at least one external electronic device through the at least one communication module, store first exercise-related information measured during a first time interval in the memory, based on information received from the at least one external electronic device, store second exercise-related information in the memory, based on information measured during a second time interval after the first time interval by at least one sensor, and when it is determined that the stored first exercise-related information and the stored second exercise-related information are information on a correlated exercise, based on a configured reference, display the first exercise-related information and the second exercise-related information as one continuous exercise through the display.

Various embodiments may measure exercise on the basis of accurate data and provide accurate records by making a link between an exercise machine which has an accurate setting value and is capable of transmitting the same and an electronic device (for example, a wearable electronic device).

Various embodiments may provide integrated exercise information to a user by linking an electronic device (for example, a wearable electronic device) with an exercise machine and merging a plurality of pieces of information on the same type of exercises to one exercise.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 30 illustrates a result screen of individual exercises in an electronic device according to an embodiment of the disclosure;

Throughout the drawings, like reference numerals will be understood to refer to like parts, components and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
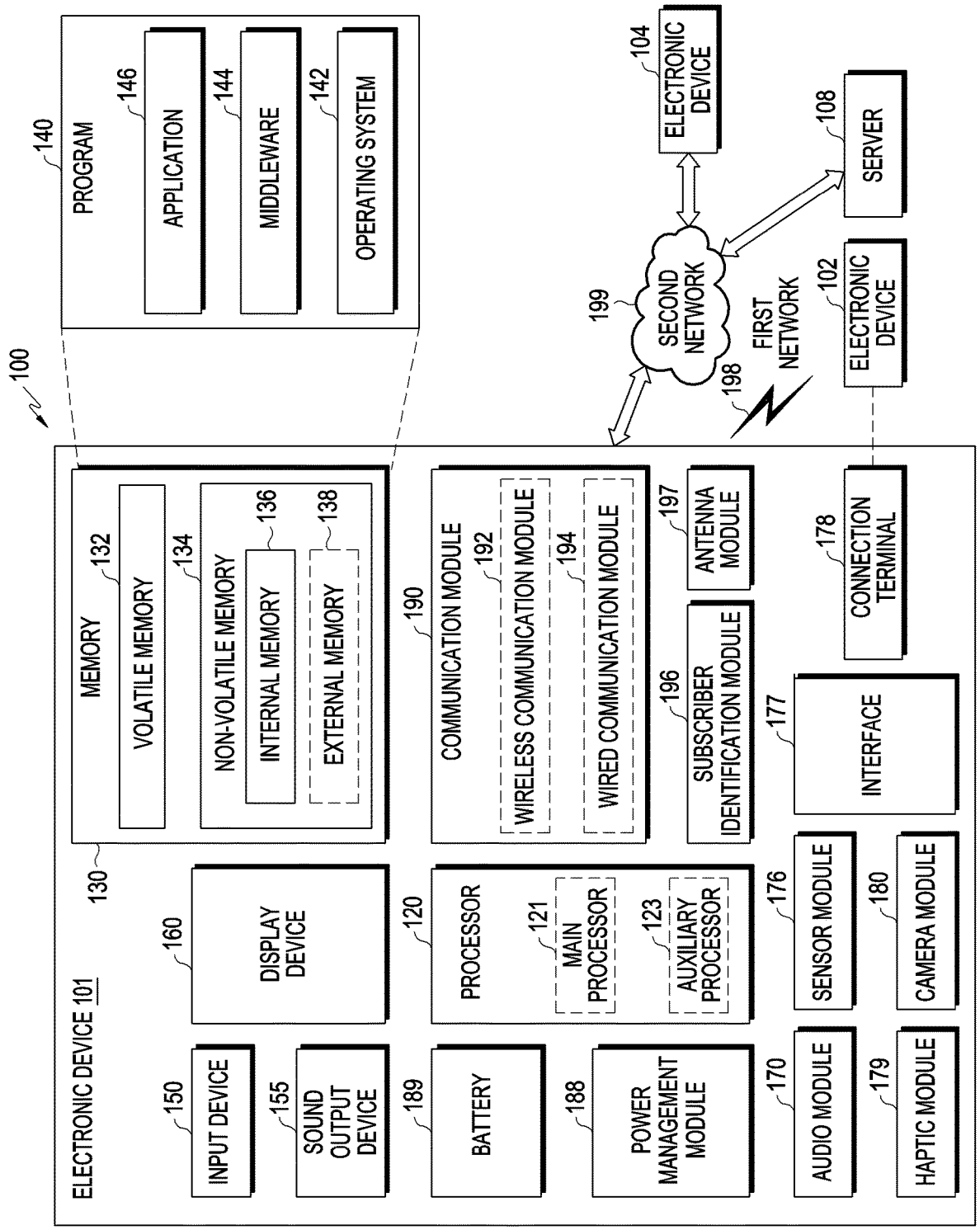
FIG. 1 illustrates a network environment according to an embodiment of the disclosure.

FIG. 1 is a block diagram illustrating an electronic device in a network environment according to an embodiment of the disclosure.

Referring to FIG. 1, an electronic device 101 in a network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by a component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module may include an antenna including a radiating element composed of a conductive material or a conductive pattern formed in or on a substrate (e.g., printed circuit board (PCB)). According to an embodiment, the antenna module 197 may include a plurality of antennas. In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a second electronic device 220, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
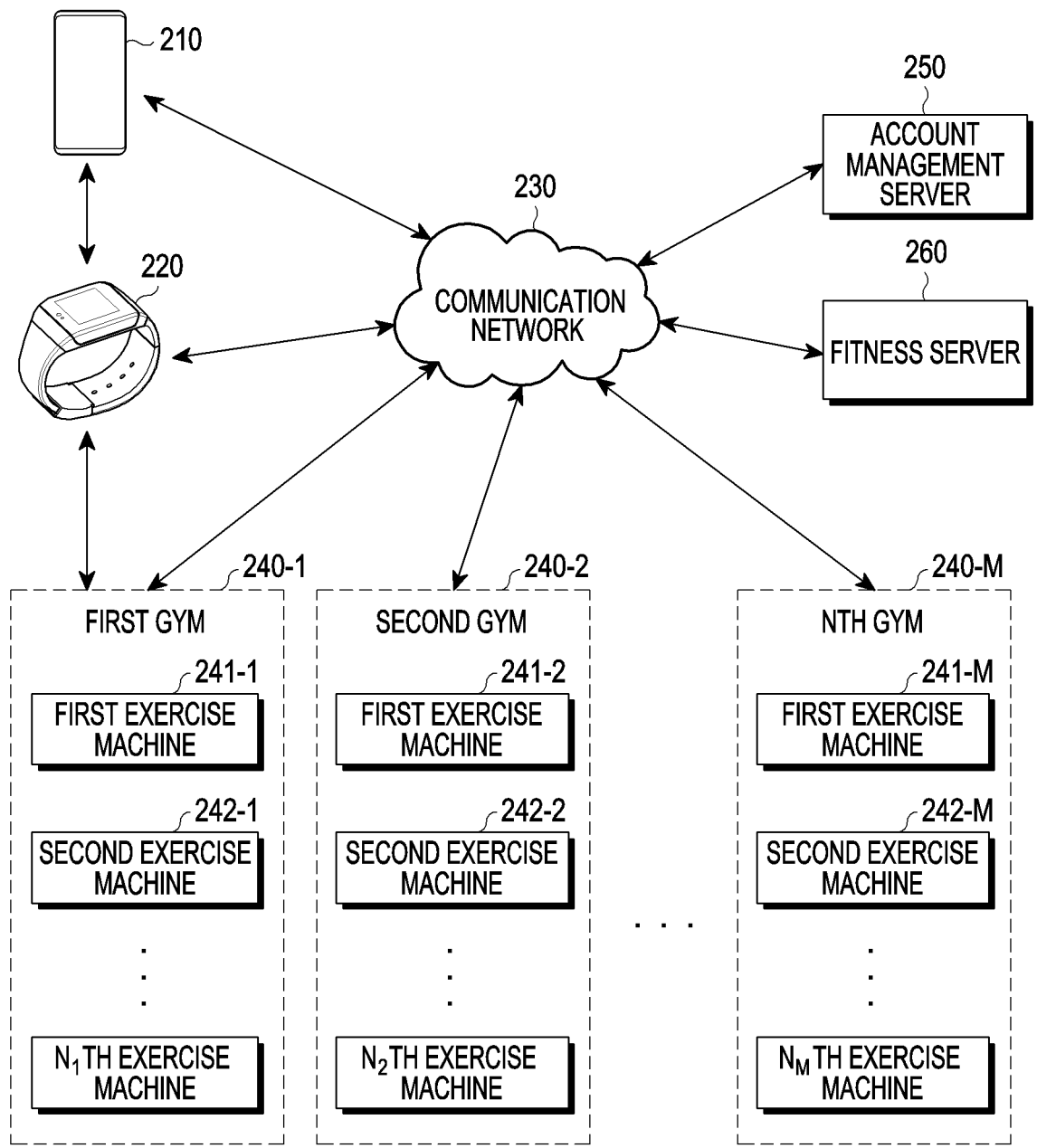
FIG. 2 illustrates a system including an electronic device and an account management server according to an embodiment of the disclosure.

FIG. 2 is a block diagram of a system including an electronic device and an account management server according to an embodiment of the disclosure.

Referring to FIG. 2, the system according to various embodiments may include a first electronic device 210 (for example, a smartphone), a second electronic device 220 (for example, a wearable electronic device), a communication network 230, at least one GYM 240-1 to 240-M, an account management server 250, and fitness server 260. In the following embodiments, the electronic device may include the first electronic device 210 or the second electronic device 220. Each GYM 240-1 to 240-M may have at least one piece of exercise machine 241-1 to 241-M installed therein. The first electronic device 210 or the second electronic device 220 may transmit and receive exercise-related data by performing short-range wireless communication with each piece of exercise machine 241-1 to 241- of each GYM 240-1 to 240-M through a short-range communication module.

The exercise-related data generated through the first electronic device, the second electronic device 220, or the exercise machine 241-1 to 241-M may be transmitted to the fitness server 260 through the communication network 230, and the transmitted exercise-related data may be stored in the fitness server 260.

The fitness server 260 may manage information in units of each GYM 240-1 to 240-M. The fitness server 260 may be separately configured for each GYM 240-1 to 240-M or a plurality of GYMs 240-1 to 240-M may be managed by one fitness server 260.

The account management server 250 may manage account information of the user of each electronic device 210 or 220 subscribed to each GYM 240-1 to 240-M as a member. According to various embodiments, the account management server 250 may be an integrated account server that integratively manages accounts for a plurality of fitness servers 260 through one user account.

A plurality of pieces of exercise machine 241-1 to 241-M, and 242-1 to 242-M . . . installed in each GYM 240-1 to 240-M may store information on a manufacturer, a model name, and a type of the exercise machine in a memory. According to various embodiments, the type of the exercise machine 241-1 to 241-M may include at least one of a treadmill, an exercise bike, a rowing machine, a stair climber, an elliptical trainer, a weight machine, or an arm curl machine.

An electronic device mentioned in various embodiments below may be used as a meaning including the first electronic device 210 or the second electronic device 220.

Figure 3:
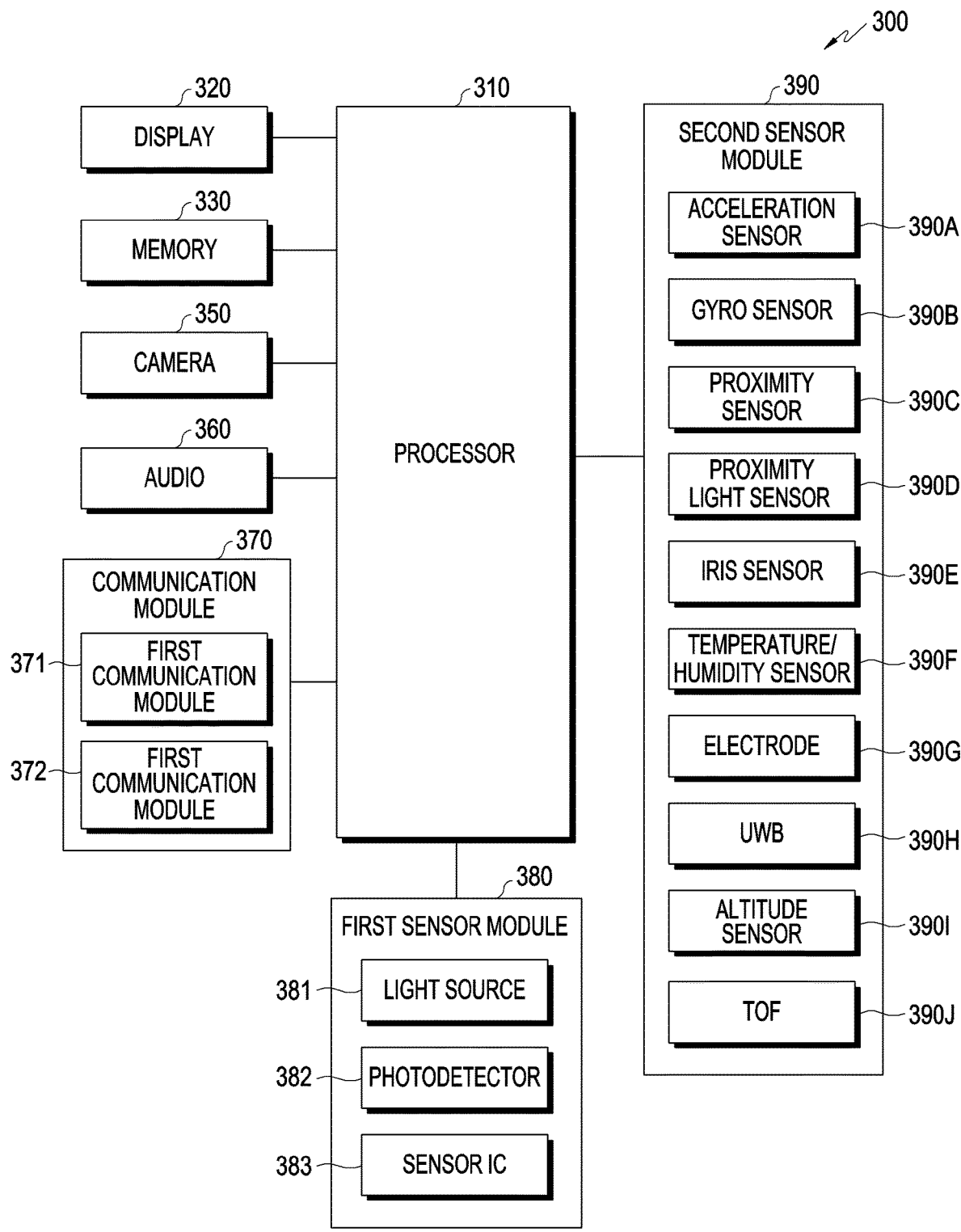
FIG. 3 is a block diagram illustrating a detailed configuration of an electronic device according to an embodiment of the disclosure.

FIG. 3 is a block diagram illustrating a detailed configuration of an electronic device according to an embodiment of the disclosure.

Referring to FIG. 3, an electronic device 300 (for example, the first electronic device 210 or the second electronic device 220 of FIG. 2) may include at least one of a processor 310, a display 320, a memory 330, a camera 350, an audio device 360, a communication module 370, a first sensor module 380, and a second sensor module 390.

The first sensor module 380 may include a light source 381, a photodetector 382, and a sensor IC 383. The second sensor module 390 may include at least one of an acceleration sensor 390A, a gyro sensor 390B, a proximity sensor 390C, a proximity light sensor 390D, an iris sensor 390E, a temperature/humidity sensor 390F, an electrode 390G, an ultra wideband (UWB) 390H, an altitude sensor 3901, and a Time of Flight (TOF) sensor 390J.

According to various embodiments, the first sensor module 380 of the electronic device 300 may operate as a photoplethysmography (PPG) sensor by the light source 381, the photodetector 382, and the sensor IC 383.

The light source 381 may include Light Emitting Diodes (LEDs) having various N wavelengths. A green wavelength is a wavelength most frequently used for measuring a heart rate and may have an advantage of being strong against noise since it shallowly penetrates the skin. A red wavelength may have an advantage of measuring a more accurate heart rate since it relatively deeply penetrates the skin. If there is an InfraRed (IR) wavelength, it is possible to acquire more much biometric information as well as a heart rate and oxygen saturation (SpO2) together with the red wavelength. If there are red, green, and IR wavelengths, it may be possible to measure skin tone. Further, when a blue wavelength is added, tendency of blood sugar may be measured. As various LED wavelengths are added, much more biometric information may be acquired. The number of wavelengths of the light source 381 is not limited to one but may be plural, and one or more emitters may be included for each wavelength.

The photodetector 382 may include one or more photodiodes. The same photodetectors 382 may be configured at locations separated by a predetermined distance from the light source 381 or one or more light sources may be configured at locations separated by different distances from the light source 381.

The sensor IC 383 may include a sensor driver controller for directly controlling a sensor and an Analog to Digital Converter (ADC). The sensor driver controller may include an emitter controller and a detector controller and may serve to directly drive an emitter or a detector. The sensor driver controller may include a role of Analog Front End (AFE). The AFE may include an amplifier for amplifying a detector value with LED drivers, an ADC for converting an analog value from the detector into a digital value, and a controller for controlling the LED driver and the ADC. The light (photo) incident through the photodetector 382 may be transmitted to the processor 310 through various filters and an ADC, and the corresponding value may be extracted as a biometric information value to be measured through an algorithm and may be shown to the user, stored through a relevant application, or transmitted to an external device.

The second sensor module 390 may include an electrode 390G for measuring electrocardiogram (ECG), bioelectrical impedance analysis (BIA), galvanic skin response (GSR), and electroencephalography (EEG) as well as an optical sensor for biometric measurement of the first sensor module 380.

The second sensor module 390 may include at least one of an acceleration sensor 390A for determining a situation of the user, a proximity sensor 390C, a gyro sensor 390B, and an iris sensor 390E. The second sensor module 390 may include at least one of a temperature/humidity sensor 390F for determining an external environment of the user, a proximity light sensor 390D, a TOF sensor 390J, and a UWB 390H.

The display 320 may provide information on current state of exercise including an exercise duration time, a heart rate, and burned calories, or an exercise guide to the user. The exercise guide may be provided in the form of at least one of a sound, vibration, or graphic.

The processor 310 may perform control to provide a resultant screen to the display 320 after exercise ends. According to various embodiments, when exercise starts, user biometric information may be measured using the first sensor module 380 or the second sensor module 390. The processor 310 may measure motion information of the user along with the biometric information, transfer at least some of the measured biometric information to the used exercise machine 241-1 to 241-M through the communication module 370, and receive exercise configuration information from the exercise machine 241-1 to 241-M. The processor 310 may receive exercise state information from the exercise machine 241-1 to 241-M through the communication module 370 and control the display 320 to display the resultant screen. According to various embodiments, when there is user identification information (identifier) configured by the electronic device 300, the corresponding information may be transmitted to the exercise machine 241-1 to 241-M when a link with each piece of exercise machine 241-1 to 241-M is made.

Figure 4:
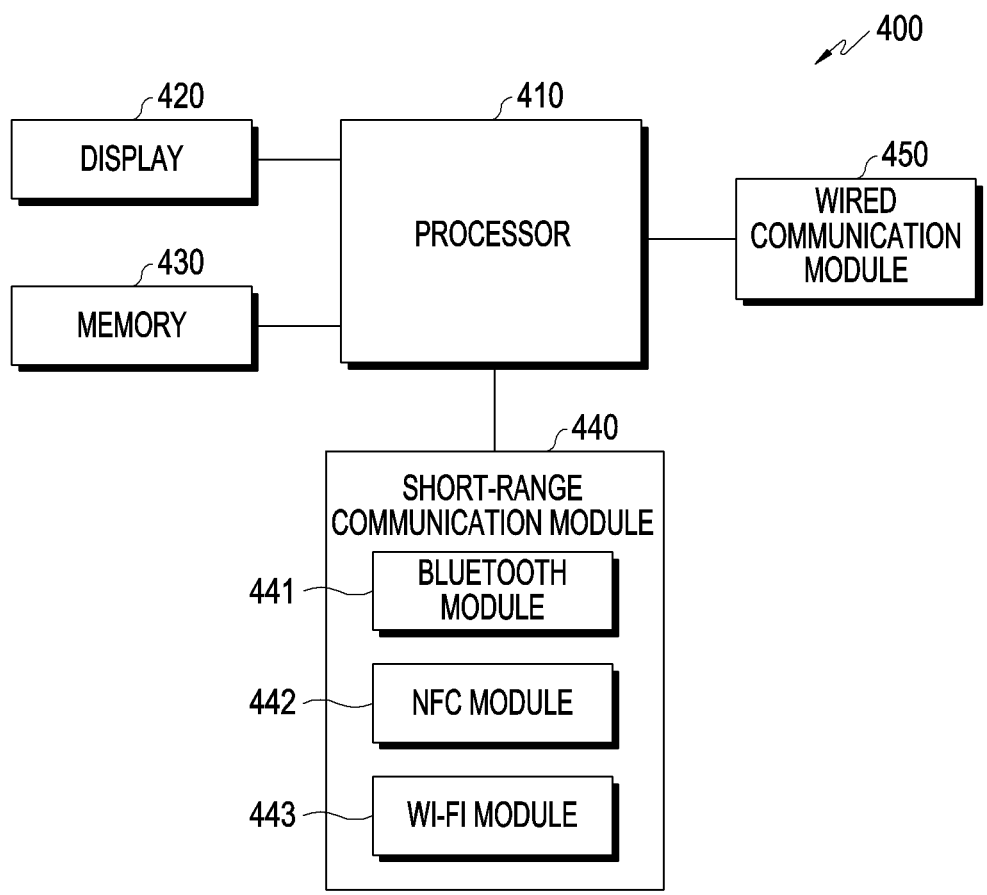
FIG. 4 is a block diagram illustrating a detailed configuration of an exercise machine according to an embodiment of the disclosure.

FIG. 4 is a block diagram illustrating a detailed configuration of exercise machine according to an embodiment of the disclosure.

Referring to FIG. 4, an exercise machine 400 (for example, the exercise machine 241-1 to 241-M of FIG. 2) may include a processor 410, a display 420, a memory 430, a short-range communication module 440, and a wired communication module 450. The short-range communication module 440 may include a Bluetooth module 441, a Near Field Communication (NFC) module 442, and a Wi-Fi module 443.

The processor 410 may transfer state information or configuration to the electronic device 300 through the short-range communication module 440 during exercise. The processor 410 may receive user biometric information from the electronic device 300 through the short-range communication module 440 and display the user biometric information on the display 420.

According to various embodiments, the exercise machine 400 may link to an external device or a server (for example, the account management server 250 or the fitness server 260) through the wired communication module 450.

The electronic device 220 according to one of various embodiments may include at least one communication module 370, the display 320, the processor 310 operatively connected to the at least one communication module 370 and the display 320, and the memory 330 operatively connected to the processor 310, wherein the memory 330 may store instructions causing the processor 310 to, when executed, make a connection with at least one exercise machine 400 through the at least one communication module 370, identify first exercise-related information measured during a first time interval, based on information received from the at least one exercise machine 400, identify second exercise-related information measured during a second time interval after the first time interval, based on information received from the at least one exercise machine 400, and when it is determined that the identified first exercise-related information and the identified second exercise-related information are information on a correlated exercise on the basis of a configured reference, display the first exercise-related information and the second exercise-related information as one continuous exercise through the display 320.

According to various embodiments, the configured reference may include at least one of a start time or an end time of the first time interval or the second time interval, a type of the exercise machine corresponding to the first time interval or the second time interval, identification information of the exercise machine, exercise time information, location information, or environment information.

According to various embodiments, the information displayed as the one continuous exercise may be transmitted to the second electronic device 220 through the at least one communication module 370.

According to various embodiments, the at least one exercise machine 400 may be an exercise machine including at least one short-range communication module 440.

According to various embodiments, the instructions may cause the processor 310 to make a connection with the at least one exercise machine 400 through a first communication module 371 and transmit connection information for sharing data, make a connection with the at least one exercise machine 400 through a second communication module 372, based on the connection information for sharing data, and transmit and receive exercise-related information to and from the at least one external electronic device through the second communication module 372.

According to various embodiments, the connection information for sharing the data may include at least one of a Bluetooth Low Energy (BLE) address, a local name, or a user account.

According to various embodiments, the instructions may cause the processor 310 to transmit user account information to the at least one exercise machine 400 through the at least one communication module 370 and receive a login result from the at least one exercise machine 400.

According to various embodiments, the electronic device 220 may further include at least one sensor 380 and 390, and the instructions may cause the processor 310 to receive information related to an exercise type from the at least one exercise machine 400 when the connection with the at least one exercise machine 400 is made, and drive a preset sensor among the at least one sensor 380 and 390 on the basis of the received information related to the exercise type.

The electronic device 220 according to one of various embodiments may include at least one communication module 370, the display 320, at least one sensor 380 and 390, the processor 310 operatively connected to the at least one communication module 370, the display 320, and the at least one sensor 380 and 390, and the memory 330 operatively connected to the processor 310, wherein the memory 330 may cause the processor 310 to, when executed, store first exercise-related information in the memory 330 on the basis of information measured during a first time interval by the at least one sensor 380 and 390, make a connection with at least one exercise machine 400 through the at least one communication module 370, identify second exercise-related information measured during a second time interval after the first time interval, based on information received from the at least one exercise machine 400, and when it is determined that the stored first exercise-related information and the identified second exercise-related information are information on a correlated exercise on the basis of a configured reference, display the first exercise-related information and the second exercise-related information as one continuous exercise through the display 320.

According to various embodiments, the configured reference may include at least one of a start time or an end time of the first time interval or the second time interval, a type of the exercise machine corresponding to the first time interval or the second time interval, identification information of the exercise machine, exercise time information, location information, or environment information.

According to various embodiments, the at least one exercise machine 400 may be an exercise machine including at least one short-range communication module 440.

According to various embodiments, the instructions may cause the processor 310 to make a connection with the at least one exercise machine 400 through a first communication module 371 and transmit connection information for sharing data, make a connection with the at least one exercise machine 400 through a second communication module 372 on the basis of the connection information for sharing data, and transmit and receive exercise-related information to and from the at least one exercise machine 400 through the second communication module 372.

According to various embodiments, the connection information for sharing the data may include at least one of a Bluetooth Low Energy (BLE) address, a local name, or a user account.

According to various embodiments, the instructions may cause the processor 310 to transmit user account information to the at least one exercise machine 400 through the at least one communication module 370 and receive a login result from the at least one exercise machine 400.

According to various embodiments, the instructions may cause the processor 310 to receive information related to an exercise type from the at least one exercise machine 400 when the connection with the at least one exercise machine 400 is made through the at least one communication module 370, and drive a preset sensor among the at least one sensor 380 and 390 on the basis of the received information related to the exercise type.

The electronic device 220 according to one of various embodiments may include at least one communication module 370, the display 320, at least one sensor 380 and 390, the processor 310 operatively connected to the at least one communication module 370, the display 320, and the at least one sensor 380 and 390, and the memory 330 operatively connected to the processor 310, wherein the memory 330 may store instructions causing the processor 310 to, when executed, make a connection with at least one exercise machine 400 through the at least one communication module 370, store first exercise-related information measured during a first time interval in the memory, based on information received from the at least one exercise machine 400, store second exercise-related information in the memory 330 on the basis of information measured during a second time interval after the first time interval by at least one sensor 380 and 390, and when it is determined that the stored first exercise-related information and the stored second exercise-related information are information on a correlated exercise on the basis of a configured reference, display the first exercise-related information and the second exercise-related information as one continuous exercise through the display 320.

According to various embodiments, the at least one exercise machine 400 may be an exercise machine including at least one short-range communication module 440.

According to various embodiments, the instructions may cause the processor 310 to make a connection with the at least one exercise machine 400 through a first communication module 371 and transmit connection information for sharing data, make a connection with the at least one exercise machine 400 through a second communication module 372 on the basis of the connection information for sharing data, and transmit and receive exercise-related information to and from the at least one exercise machine 400 through the second communication module.

According to various embodiments, the connection information for sharing the data may include at least one of a Bluetooth Low Energy (BLE) address, a local name, or a user account.

According to various embodiments, the instructions may cause the processor 310 to transmit user account information to the at least one exercise machine 400 through the at least one communication module 370 and receive a login result from the at least one exercise machine 400.

Figure 5:
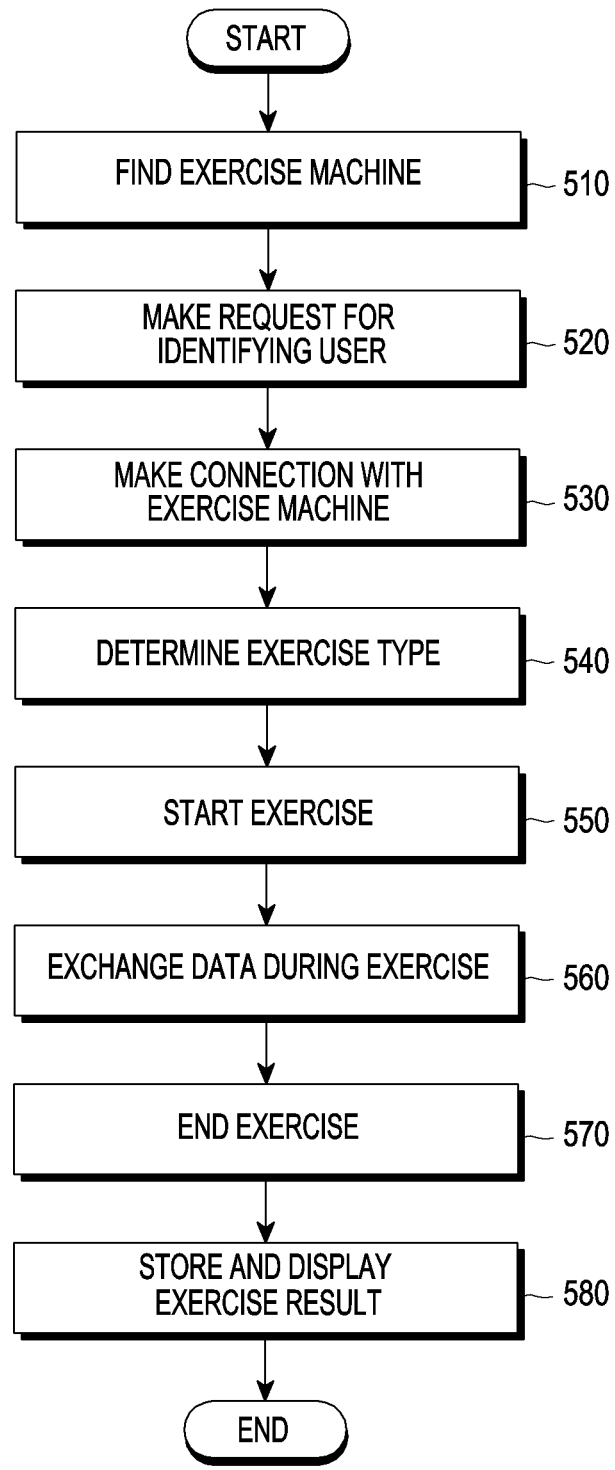
FIG. 5 is a flowchart illustrating a method of linking between an electronic device and an exercise machine according to an embodiment of the disclosure.

FIG. 5 is a flowchart illustrating a method of linking between an electronic device and exercise machine according to an embodiment of the disclosure.

Referring to FIG. 5, in operation 510, the electronic device 300 (for example, the first electronic device 210 or the second electronic device 220 of FIG. 2) may discover exercise machine (for example, the exercise machine 241-1 to 241-M of FIG. 2 or the exercise machine 400 of FIG. 4) disposed in each GYM 240-1 to 240-M. According to various embodiments, the exercise machine 400 may be discovered by the electronic device 300 in such a manner that the user designates specific exercise machine by tagging the exercise machine 400 through proximity communication of Near Field Communication (NFC) or the user may select one of the pieces of exercise machine by searching for exercise machine around the electronic device 300 through a Bluetooth Low Energy (BLE) module. According to various embodiments, the exercise machine 400 may search for the electronic device 300 of the user and make a request for connecting to the found electronic device 300.

When the electronic device 300 has found the exercise machine 400, the electronic device 300 may identify whether the user will do an exercise using the corresponding exercise machine 400 through the display of the electronic device 300 in operation 520. According to various embodiments, a procedure of receiving consent from the user may be omitted.

When the user consents, the electronic device 300 may be connected to the corresponding exercise machine 400 in operation 530. For the connection with the exercise machine 400, BLE may be used to reduce battery consumption of the electronic device 300, and another communication protocol for exchanging data may be used according to various embodiments.

When the connection between the electronic device 300 and the exercise machine 400 is completed, the electronic device 300 may determine a type of the exercise machine 400 and drive a biometric sensor (for example, the first sensor module 380 or the second sensor module 390 of FIG. 3) configured in accordance with the determined type of the exercise machine in operation 540. For example, in the case of a treadmill for aerobic exercise, a sensor for acquiring a heart rate (HR) and oxygen saturation may be driven. In the case of weight-based exercise such as arm curls, a sensor for measuring blood pressure (for example, PPG (for example, the first sensor module 380 of FIG. 3) or ECG (for example, the second sensor module 390 of FIG. 3)) may be driven. Further, the electronic device 300 may prepare reception of data from the corresponding connected exercise machine 400.

When exercise using the connected exercise machine 400 starts in operation 550, the exercise machine 400 may transfer exercise-related information to the connected electronic device 300 and thus data may be exchanged between the exercise machine 400 and the electronic device 300 in operation 560. The exercise machine 400 may transfer exercise information configured in the exercise device 400 by the user to the electronic device 300, and the electronic device 300 may sense information on a user body state and transfer the same to the exercise machine 400. According to various embodiments, when the exercise machine 400 pauses during exercise or restarts the exercise, the corresponding information may be transmitted to the electronic device 300.

In operation 570, the electronic device 300 may stop recording and storing exercise by a user control through a User Interface (UI), or the end of the operation in which the electronic device 300 records and stores exercise may be automatically processed through an exercise end input into the exercise machine 400.

When the exercise ends, the electronic device 300 may terminate the connection with the exercise machine 400, show the user stored data through a display (for example, the display 320), and store required data in a memory (for example, the memory 330) in operation 580. According to various embodiments, data stored in the memory 330 of the electronic device 300 (for example, the second electronic device 220 of FIG. 2) may be synchronized with data of another electronic device (for example, the first electronic device 210 of FIG. 2), and thus more detailed and various exercise results may be provided to the user.

Figure 6A:
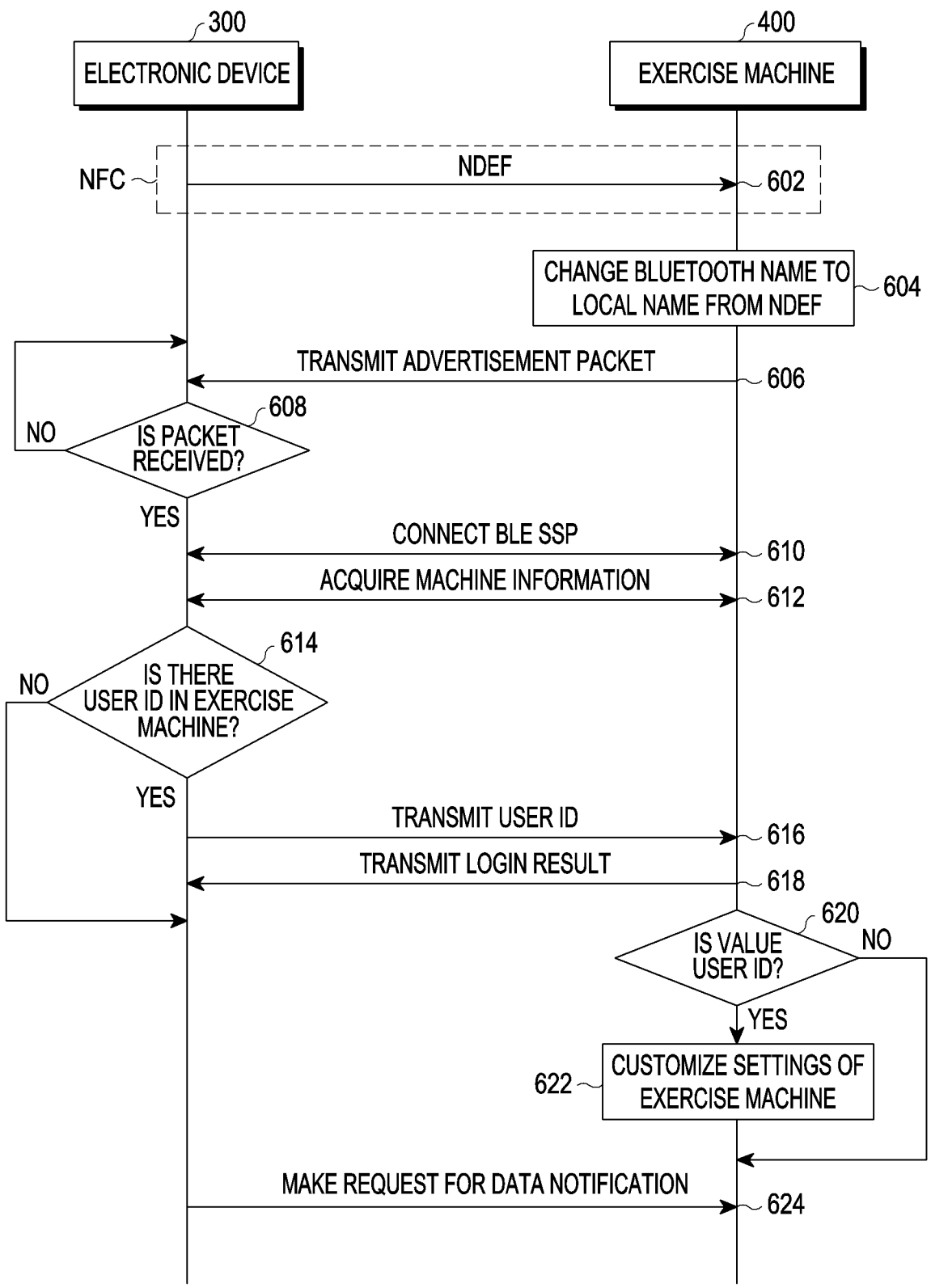
FIG. 6A is a flowchart illustrating a method of making a connection between an electronic device and an exercise machine and exchanging data according to an embodiment of the disclosure.

FIG. 6A is a flowchart illustrating a method of connecting an electronic device and an exercise machine and exchanging data according to an embodiment of the disclosure.

Figure 6B:
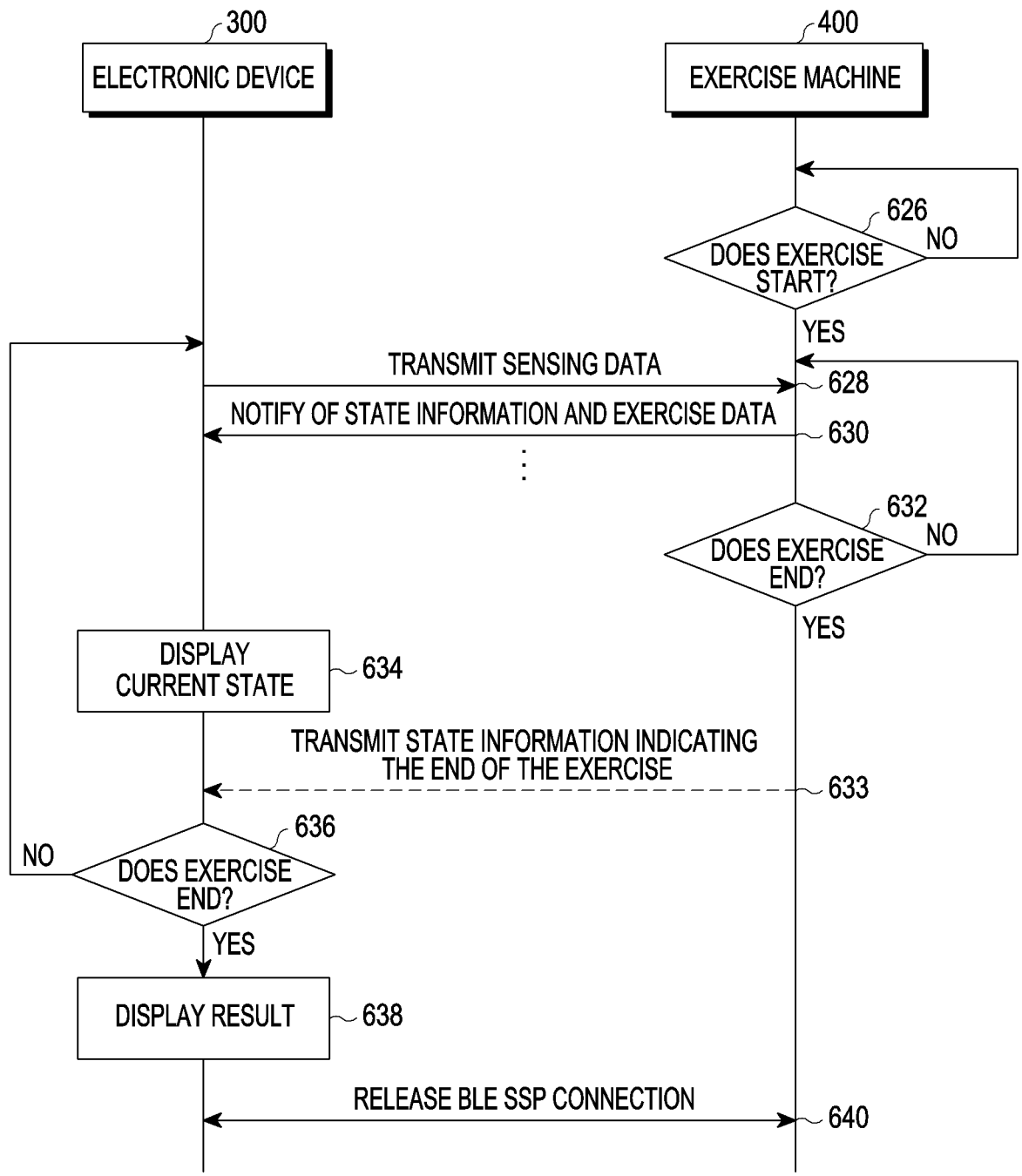
FIG. 6B is a flowchart illustrating a method of making a connection between an electronic device and an exercise machine and exchanging data according to an embodiment of the disclosure.

FIG. 6B is a flowchart illustrating a method of connecting an electronic device and an exercise machine and exchanging data according to an embodiment of the disclosure.

Referring to FIG. 6A, in operation 602, the electronic device 300 (for example, the first electronic device 210 or the second electronic device 220 of FIG. 2) may transmit NFC Data Exchange Format (NDEF) data by tagging a Near Field Communication (NFC) module on the exercise machine 400. According to various embodiments, the electronic device 300 may operate as an NFC tag, and the exercise machine 400 may operate as an NFC reader.

According to various embodiments, the NDEF data may include at least one of a BLE address, a Low Energy (LE) role, a local name, a confirmation value, or a random value. The NDEF data may be used as connection information for data sharing between the electronic device 300 and the exercise machine 400. At least one piece of the NDEF data received by the exercise machine 400 may be stored in a memory (for example, the memory 430 of FIG. 4) of the exercise machine 400. The electronic device 300 may play a central role according to a BLE protocol and the exercise machine 400 may play a peripheral role according to a BLE protocol depending on the LE role included in the NDEF data.

In operation 604, the exercise machine 400 may change a Bluetooth name to a local name on the basis of the received NDEF data. According to various embodiments, the local name may be used to identify the exercise machine 400 by the electronic device 300 when the electronic device 300 is connected to the exercise machine 400 and exchange information therewith.

In operation 606, the exercise machine 400 may transmit an advertisement packet to the electronic device 300. According to various embodiments, the exercise machine 400 may transmit the advertisement packet to the electronic device 300 in a broadcasting manner According to various embodiments, the advertisement packet may include at least one piece of data received from the electronic device 300 through the NDEF data, for example, at least one of a Fitness Machine Service (FTMS) Universally Unique Identifier (UUID), a BLE address, an LE role, a local name, a confirmation value, or a random value. According to various embodiments, the advertisement packet may include information on an exercise machine type corresponding to the exercise machine 400.

When the electronic device 300 receives the advertisement packet in operation 608, the electronic device 300 may make a BLE Secure Simple Pairing (SSP) connection with the exercise machine 400 on the basis of information included in the received advertisement packet (for example, at least one piece of information included in the NDEF data) in operation 610. In operation 612, the electronic device 300 may acquire machine information from the exercise machine 400. According to various embodiments, the electronic device 300 may make a request for machine information to the exercise machine 400 on the basis of the BLE protocol, and the exercise machine 400 may transmit machine information to the electronic device 300 in response to the request for the machine information from the electronic device 300. According to various embodiments, the machine information transmitted by the exercise machine 400 may include at least one of manufacturer information, a model name of the exercise machine, and information on a type of the exercise machine (fitness machine type) information.

In operation 614, the electronic device 300 may identify whether there is user identification information (user identifier (ID)) for the exercise machine 400 on the basis of the information on the exercise machine received from the exercise machine 400.

When there is the user ID corresponding to the exercise machine 400 in the electronic device 300 on the basis of the identification result, the electronic device 300 may transmit the user ID to the exercise machine 400 in operation 616. According to various embodiments, the electronic device 300 may also transmit a password of the user ID when transmitting the user ID.

According to various embodiments, the exercise machine 400 may receive the user ID from the electronic device 300 and log in the electronic device 300 with the received user ID. In operation 618, the exercise machine 400 may transmit the login result to the electronic device 300 after performing the login.

According to various embodiments, a login key (for example, a machine ID) corresponding to the user ID may be transmitted instead of the user ID in operation 616. For example, when the electronic device 300 (for example, the first electronic device 210 or the second electronic device 220) is logged in with the corresponding user ID, the electronic device 300 may receive a machine key of the corresponding user ID from a server (for example, the account management server 250). The electronic device 300 may transmit the login key received from the server to the exercise machine 400. The exercise machine 400 may process the login of the user onto the electronic device 300 by identifying the login key received from the electronic device 300 through the server. According to various embodiments, the server may issue the login key in the form of a hash code and identify the user by means of the login key. Hereinafter, the operation for transmitting the user ID may be replaced with the operation for transmitting the login key in the description of drawings, and the user ID may be interpreted to include the login key. For example, the login of the user onto the electronic device 300 may be processed through authentication of the login key instead of authentication of the user ID in the description of drawings below.

The exercise machine 400 may authenticate the user ID received from the electronic device 300 and when the user ID is a valid user ID on the basis of the authentication result in operation 620, settings for the exercise machine 400 may be customized to corresponding to the user ID in operation 622.

In operation 624, the electronic device 300 may make a request for data notification to the exercise machine 400.

Referring to FIG. 6B, in operation 626, when the exercise starts, the electronic device 300 may acquire sensing data in real time by driving a configured sensor corresponding to the exercise machine 400. In operation 628, the electronic device 300 may transmit the sensing data acquired in real time to the exercise machine 400. In operation 630, the exercise machine 400 may notify the electronic device 300 of state information and exercise data in response to the request for data notification received from the electronic device 300. According to various embodiments, in operation 634, the electronic device 300 may display information related to the current state on the display on the basis of the sensing data acquired by the electronic device 300 or the state information or the exercise data received from the exercise machine 400.

When the exercise ends in operation 632, the exercise machine 400 may transmit state information indicating the end of the exercise to the electronic device 300 in operation 633.

The electronic device 300 may receive the state information indicating the end of the exercise from the exercise machine 400 and determine the end of the exercise in operation 636. According to various embodiments, the electronic device 300 may display the exercise result on the display in accordance with the determination of the end of the exercise in operation 638.

According to the end of the exercise, the electronic device 300 may release the BLE SSP connection with the exercise machine 400 in operation 640.

Figure 7A:
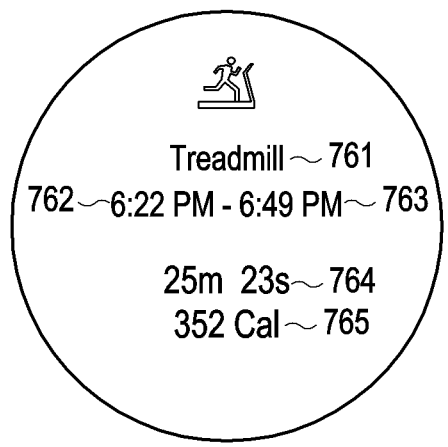
FIG. 7A illustrates a result screen displayed on an electronic device after exercise ends according to an embodiment of the disclosure.

FIG. 7A illustrates a result screen displayed on the electronic device after the exercise ends according to an embodiment of the disclosure.

Figure 7B:
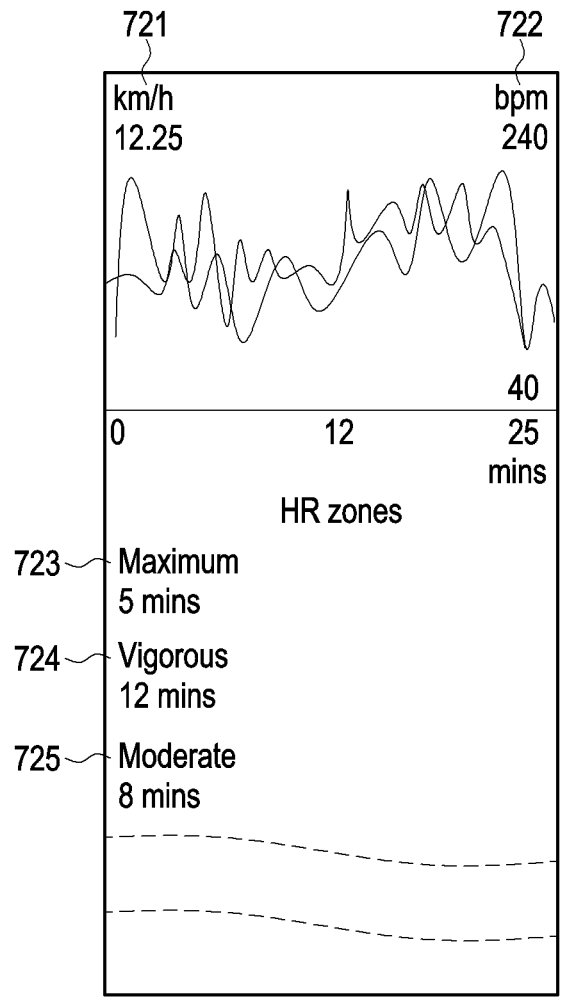
FIG. 7B illustrates a result screen displayed on an electronic device after exercise ends according to an embodiment of the disclosure.

FIG. 7B illustrates a result screen displayed on the electronic device after the exercise ends according to an embodiment of the disclosure.

Figure 7C:
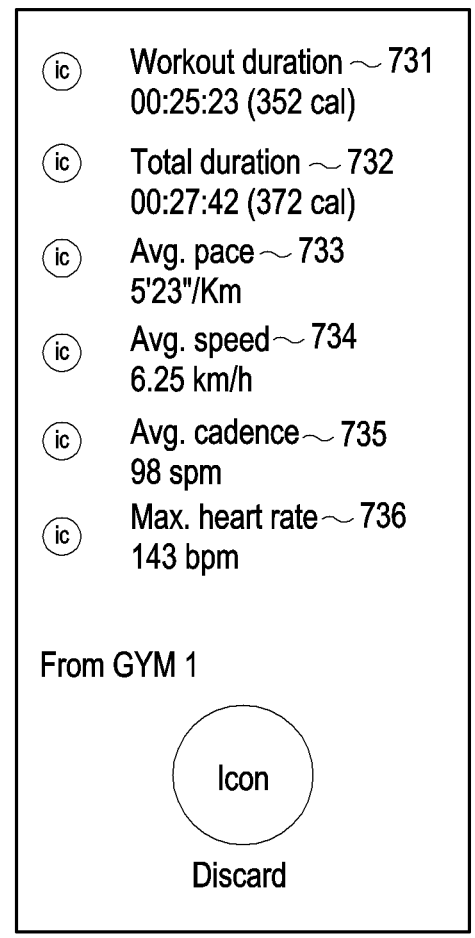
FIG. 7C illustrates a result screen displayed on an electronic device after exercise ends according to an embodiment of the disclosure.

FIG. 7C illustrates a result screen displayed on the electronic device after the exercise ends according to an embodiment of the disclosure.

According to various embodiments, when the exercise is conducted and then ends in the state in which the electronic device 300 and the exercise machine 400 are connected to each other as illustrated in FIGS. 6A and 6B, the exercise result illustrated in FIGS. 7A to 7C may be displayed on the screen.

Referring to FIGS. 7A, 7B, and 7C, the electronic device 300 (for example, the second electronic device 220 (wearable electronic device)) may display information related to the exercise by the user using the exercise machine 400 (for example, a treadmill) on the display. According to various embodiments, the second electronic device 220 may display the information related to the exercise on the display on the basis of information received from the exercise machine 400.

For example, referring to FIG. 7A, the second electronic device 200 may display at least one of a type 761 of the exercise machine, exercise time information (a start time 762, an end time 763, or an elapsed time 764), or information on total calories 765 burned during the corresponding exercise on the display on the basis of information collected or measured through a sensor included in the second electronic device 220 or information received from the exercise machine 400.

According to various embodiments, referring to FIG. 7B, the second electronic device 200 may display at least one of an average speed 721, an average bpm 722, and exercise intensity (for example, maximum 723, vigorous 724, and moderate 725) on the display on the basis of information collected or measured through a sensor included in the second electronic device 220 or information received from the exercise machine 400.

According to various embodiments, referring to FIG. 7C, the second electronic device 200 may display information on an exercise time 731, a total exercise time 732, total calorie information, Avg. pace information 733, Avg. speed information 734, average (Avg.) cadence information 735, and Max. heart rate 736 on the basis of information collected or measured through a sensor included in the second electronic device 220 or information received from the exercise machine 400. When it is determined that the exercise-related information received from the exercise machine 400 is not valid, the second electronic device 220 may additionally display a user interface (for example, "Discard") for receiving a user input to exclude the received exercise information.

Figure 8A:
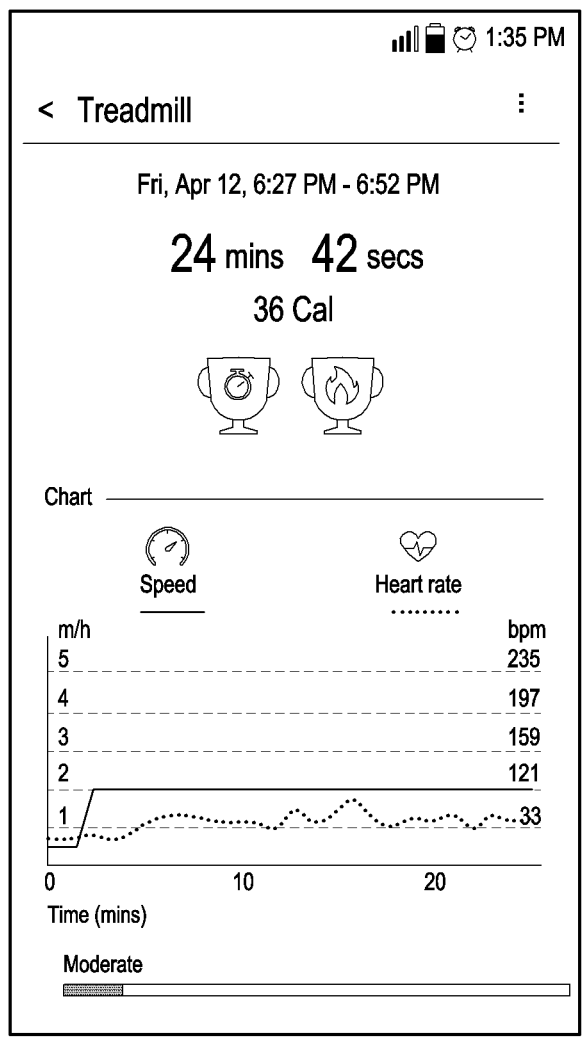
FIG. 8A illustrates a result screen displayed on an electronic device after exercise ends according to an embodiment of the disclosure.

FIG. 8A illustrates a result screen displayed on the electronic device after the exercise ends according to an embodiment of the disclosure.

Figure 8B:
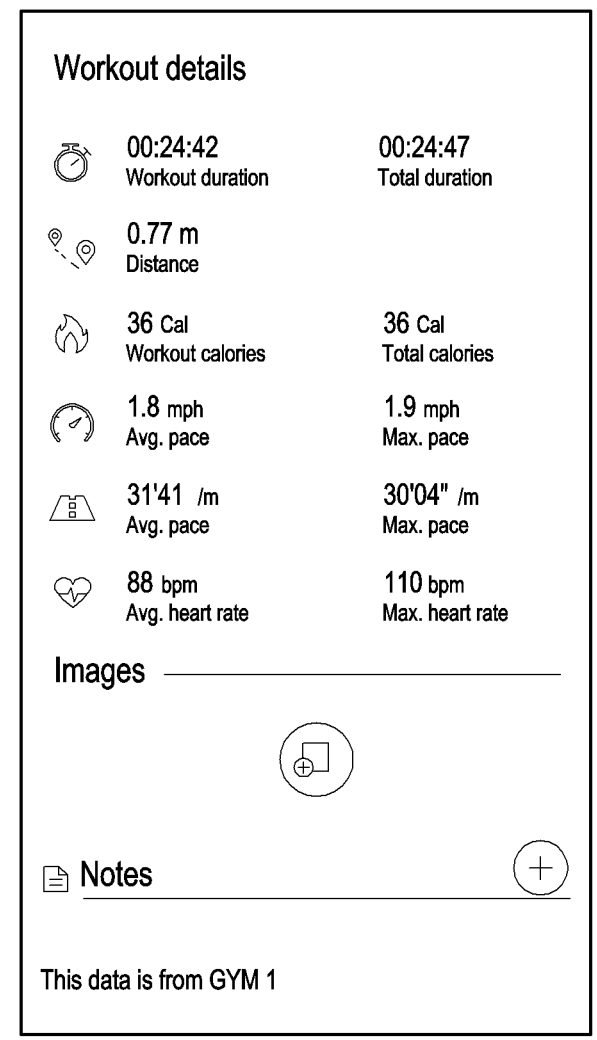
FIG. 8B illustrates a result screen displayed on an electronic device after exercise ends according to an embodiment of the disclosure.

FIG. 8B illustrates a result screen displayed on the electronic device after the exercise ends according to an embodiment of the disclosure.

Referring to FIGS. 8A and 8B, the first electronic device 210 (for example, a smartphone) according to an embodiment may display, on the display, exercise-related information received from the second electronic device 220 or the exercise machine 400 after the exercise ends. According to various embodiments, information displayed on the first electronic device 210 may be similar to or the same as information displayed on the second electronic device 220 illustrated in FIGS. 7A to 7C. According to various embodiments, the information displayed on the first electronic device 210 may include more various or more detailed information than the information displayed on the second electronic device 220 illustrated in FIGS. 7A to 7C.

Figure 9A:
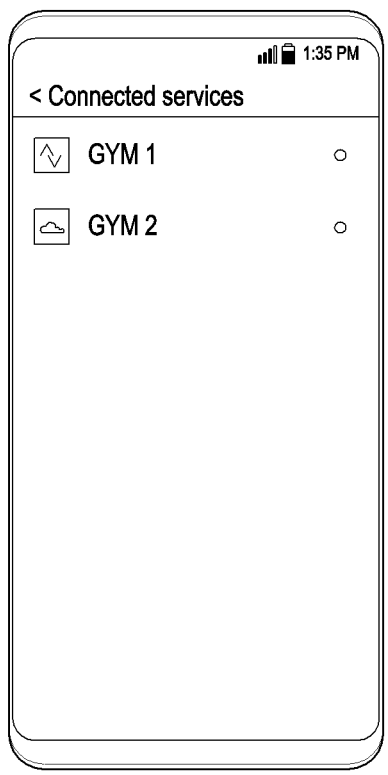
FIG. 9A illustrates a screen for setting a user account in an electronic device according to an embodiment of the disclosure.

FIG. 9A is a screen illustrating the operation for configuring a user account in the electronic device according to an embodiment of the disclosure.

Figure 9B:
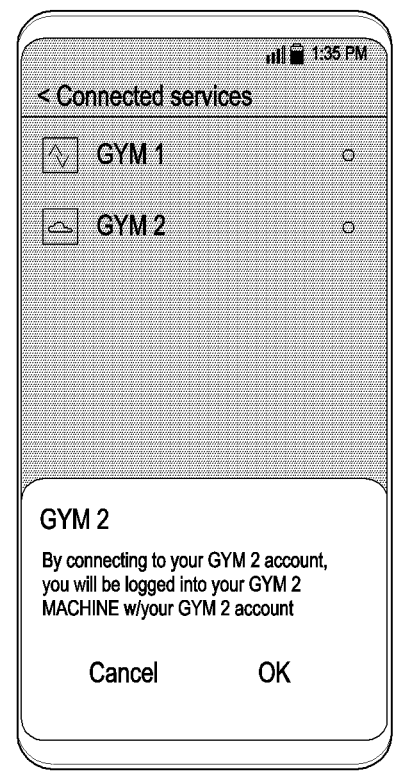
FIG. 9B illustrates a screen for setting a user account in an electronic device according to an embodiment of the disclosure.

FIG. 9B is a screen illustrating the operation for configuring a user account in the electronic device according to an embodiment of the disclosure.

Figure 9C:
FIG. 9C illustrates a screen for setting a user account in an electronic device according to an embodiment of the disclosure.

FIG. 9C is a screen illustrating the operation for configuring a user account in the electronic device according to an embodiment of the disclosure.

Figure 9D:
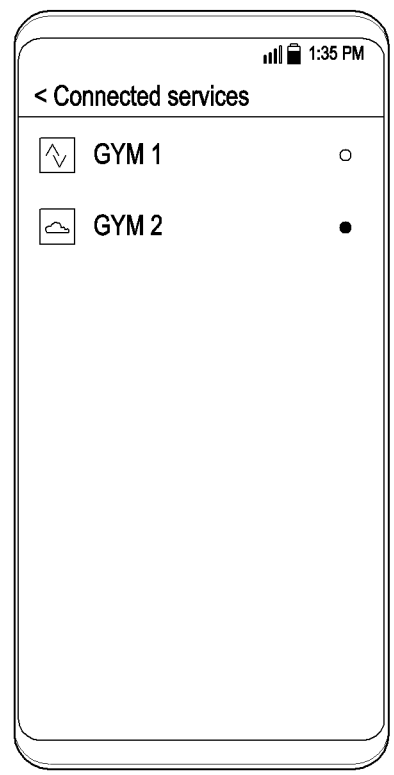
FIG. 9D illustrates a screen for setting a user account in an electronic device according to an embodiment of the disclosure.

FIG. 9D is a screen illustrating the operation for configuring a user account in the electronic device according to an embodiment of the disclosure.

Referring to FIG. 9A, a list of connected GYM service providers (for example, GYM 1 or GYM 2) may be displayed in a first screen for configuring a user account. The user may select a specific GYM service provider (for example, GYM 2) among a plurality of GYM service providers illustrated in FIG. 9A. When the user selects the specific GYM service provider in FIG. 9A, a message indicating registration of an account for the selected GYM service provider may be displayed as illustrated in FIG. 9B.

According to various embodiments, the user account may be registered through an account registration screen of FIG. 9C, and when a login procedure is completed, a login key related to the user account may be issued and stored in the memory 330 of the electronic device 300. According to various embodiments, as illustrated in FIG. 9D, selection for the GYM service provider of which the account is registered may be displayed, which may mean that the login key for the GYM service provider of which the account is registered is issued and stored.

The process for registering or configuring the user account may be performed by the second electronic device 220 or the first electronic device 210.

Figure 10A:
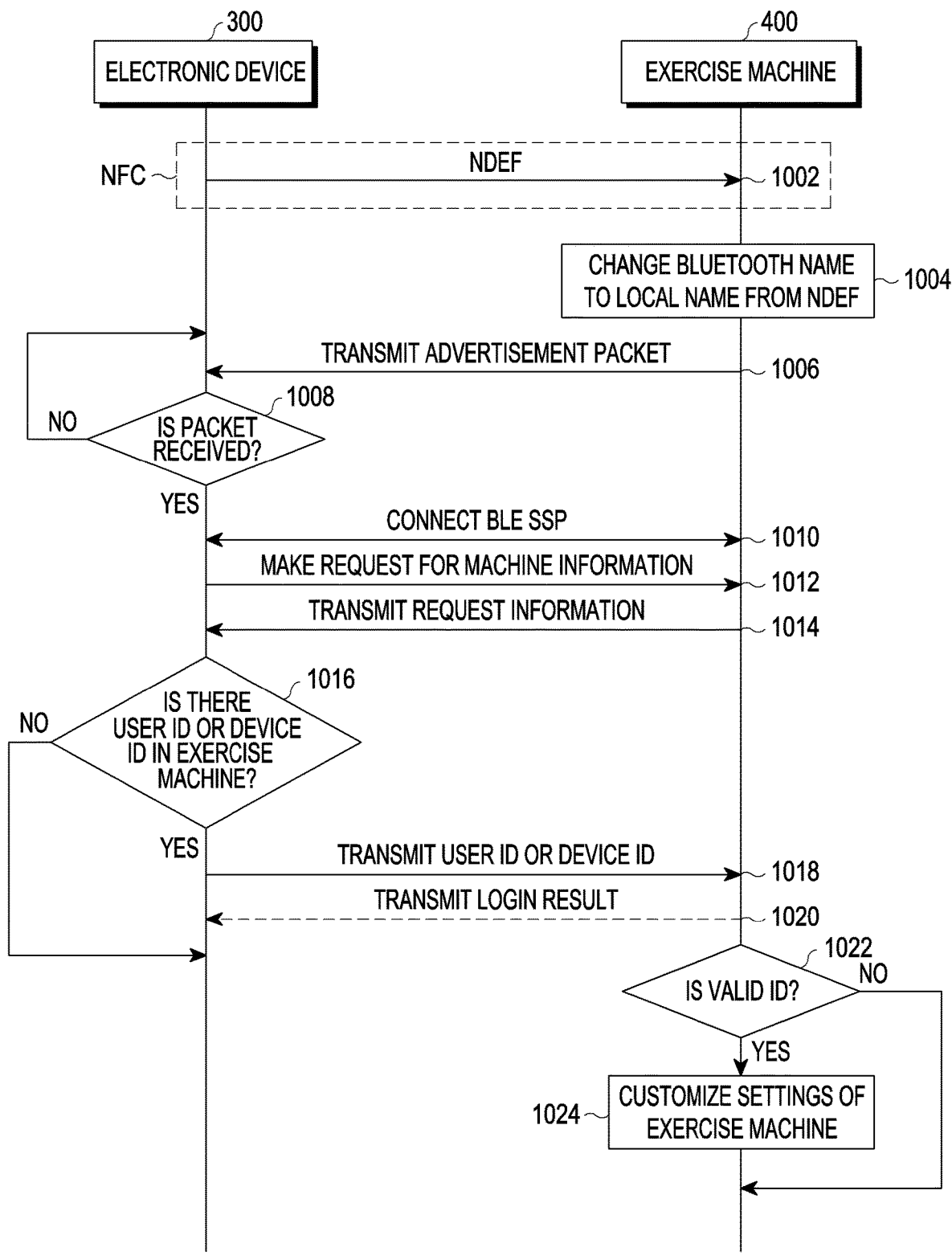
FIG. 10A is a flowchart illustrating a method of making a connection between an electronic device and an exercise machine and exchanging data according to an embodiment of the disclosure.

FIG. 10A is a flowchart illustrating a method of making a connection between an electronic device and an exercise machine and exchanging data according to an embodiment of the disclosure.

Figure 10B:
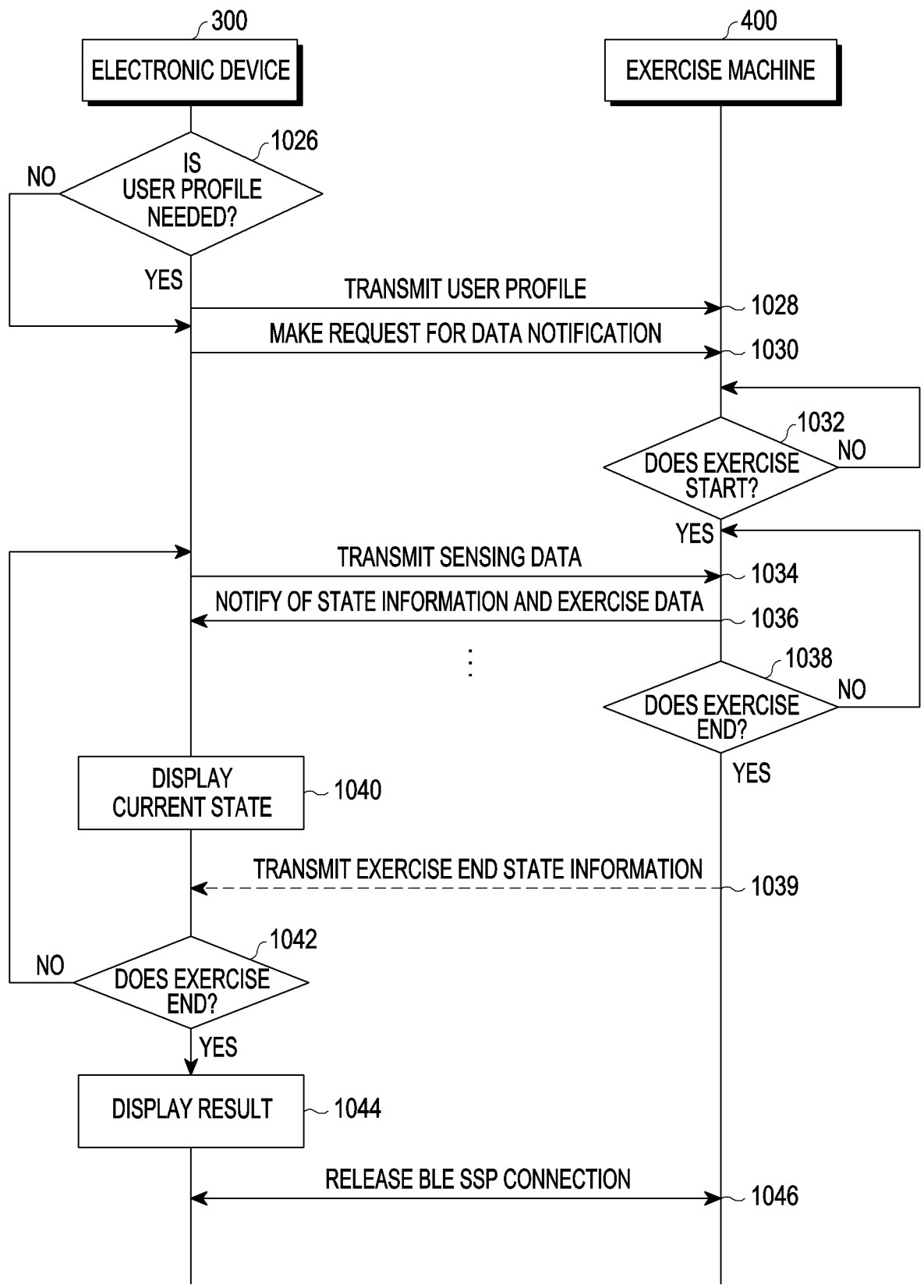
FIG. 10B is a flowchart illustrating a method of making a connection between an electronic device and an exercise machine and exchanging data according to an embodiment of the disclosure.

FIG. 10B is a flowchart illustrating a method of making a connection between an electronic device and an exercise machine and exchanging data according to an embodiment of the disclosure.

According to various embodiments, the operation for additionally transmitting user profile information in the state in which the electronic device 300 and the exercise machine 400 are connected through NFC/BLE is described with reference to FIGS. 10A and 10B.

Referring to FIGS. 10A and 10B, detailed description of the operation similar to or the same as FIGS. 6A and 6B is omitted. For example, in the following description, operations 1002 to 1010 of FIGS. 10A and 10B may be the same as or similar to operations 602 to 610 of FIGS. 6A and 6B, and operations 1030 to 1046 of FIGS. 10A and 10B may be the same as or similar to operations 624 to 640 of FIGS. 6A and 6B.

According to various embodiments, when the exercise machine 400 informs the electronic device 300 (for example, the second electronic device 220) that additional information of a user profile is needed to calculate accurate calories of the currently conducted exercise, the electronic device 300 may identify additional information of the user profile including at least one of a height, weight, sex, and age of the user and transmit at least one piece information of the identified user profile information to the exercise machine 400, so that the exercise machine 400 may understand the user in detail and accurately calculate calories on the basis thereof.

In operation 1002, the electronic device 300 (for example, the first electronic device 210 or the second electronic device 220 of FIG. 2) may transmit NFC Data Exchange Format (NDEF) data by tagging an NFC module on the exercise machine 400. According to various embodiments, the electronic device 300 may operate as an NFC tag, and the exercise machine 400 may operate as an NFC reader.

In operation 1004, the exercise machine 400 may change a Bluetooth name to a local name on the basis of the received NDEF data. According to various embodiments, the local name may be used to identify the electronic device 300 by the exercise machine 400 when the electronic device 300 is connected to the exercise machine 400 and exchange information therewith.

In operation 1006, the exercise machine 400 may transmit an advertisement packet to the electronic device 300. According to various embodiments, the exercise machine 400 may transmit the advertisement packet to the electronic device 300 in a broadcasting manner.

When the electronic device 300 receives the advertisement packet in operation 1008, the electronic device 300 may make a BLE Secure Simple Pairing (SSP) connection with the exercise machine 400 on the basis of information included in the received advertisement packet (for example, at least one piece of information included in the NDEF data) in operation 1010. According to various embodiments, the electronic device 300 may make a request for machine information to the exercise machine 400 on the basis of the BLE protocol in operation 1012, and the exercise machine 400 may transmit the machine information to the electronic device 300 in response to the request for the machine information from the electronic device 300 in operation 1014. According to various embodiments, the machine information transmitted by the exercise machine 400 may include at least one of manufacturer information, a model name of the exercise machine, and information on a type of the exercise machine (fitness machine type) information. According to various embodiments, the machine information transmitted by the exercise machine 400 may further include information on whether an ID (for example, a user ID or a device ID) is needed or information on whether a user profile is needed.

In operation 1016, the electronic device 300 may identify whether there is user identification information (user identifier (ID)) or a device ID (machine ID) for the exercise machine 400 on the basis of information on the exercise machine received from the exercise machine 400.

When there is the user ID or the device ID corresponding to the exercise machine 400 in the electronic device 300 on the basis of the identification result, the electronic device 300 may transmit the user ID or the device ID to the exercise machine 400 in operation 1018. According to various embodiments, the electronic device 300 may also transmit a password of the user ID when transmitting the user ID.

According to various embodiments, a login key (for example, a machine ID) corresponding to the user ID may be transmitted instead of the user ID in operation 1018. For example, when the electronic device 300 (for example, the first electronic device 210 or the second electronic device 220) is logged in with the corresponding user ID, the electronic device 300 may receive a machine key of the corresponding user ID from a server (for example, the account management server 250). The electronic device 300 may transmit the login key received from the server to the exercise machine 400. The exercise machine 400 may process the login of the user onto the electronic device 300 by identifying the login key received from the electronic device 300 through the server. According to various embodiments, the server may issue the login key in the form of a hash code and identify the user by means of the login key.

According to various embodiments, the exercise machine 400 may receive the user ID or the device ID from the electronic device 300 and log in the electronic device 300 with the received user ID or device ID. In operation 1020, the exercise machine 400 may transmit the login result to the electronic device 300 after performing the login.

The exercise machine 400 may authenticate the user ID or the device ID received from the electronic device 300 and when the ID is a valid ID on the basis of the authentication result in operation 1022, settings of the exercise machine 400 (for example, intensity, chair height, or machine settings) may be customized to correspond to the user ID or the device ID in operation 1024.

According to various embodiments, the electronic device 300 may identify information on whether user profile information is needed in the machine information received from the exercise machine 400. When the electronic device 300 determines that the user profile information is needed by the exercise machine 400 in operation 1026, the electronic device 300 may transmit the user profile to the exercise machine 400 in operation 1028. According to various embodiments, when receiving the machine information from the exercise machine 400 in operation 1014, the electronic device 300 may receive information on whether the user ID is needed, the device ID is needed, or the user profile is needed. For example, it may be determined whether the user profile is needed through information on whether the user profile is needed in the machine information, and when the electronic device 300 has a user profile which can be shared, the electronic device 300 may automatically transmit the user profile to the exercise machine 400 regardless of the need of the user profile. According to various embodiments, in both the cases, advance permission of the user for sharing may be required, and only default profile information (for example, male/female information) configured in default may be transmitted when permission of the user for sharing is not obtained. In operation 1030, the electronic device 300 may make a request for data notification to the exercise machine 400.

In operation 1032, when the exercise starts, the electronic device 300 may acquire sensing data in real time by driving a configured sensor corresponding to the exercise machine 400. In operation 1034, the electronic device 300 may transmit the sensing data acquired in real time to the exercise machine 400. In operation 1036, the exercise machine 400 may notify the electronic device 300 of state information and exercise data in response to the request for data notification received from the electronic device 300. According to various embodiments, in operation 1040, the electronic device 300 may display information related to the current state on the display on the basis of the sensing data acquired by the electronic device 300 or the state information or the exercise data received from the exercise machine 400.

When the exercise ends in operation 1038, the exercise machine 400 may transmit state information indicating the end of the exercise to the electronic device 300 in operation 1039.

The electronic device 300 may receive the state information indicating the end of the exercise from the exercise machine 400 and determine the end of the exercise in operation 1042. According to various embodiments, the electronic device 300 may display the exercise result on the display in accordance with the determination of the end of the exercise in operation 1044.

According to the end of the exercise, the electronic device 300 may release the BLE SSP connection with the exercise machine 400 in operation 1046.

According to various embodiments, when the connection between the electronic device 300 (for example, the second electronic device 220) and the exercise machine 400 is attempted two or more times for the reason of the connection therebetween being disconnected or the electronic device 300 being terminated by mistake during the exercise using the exercise device 400, the electronic device may merge exercise results and process the exercises as one exercise instead of storing respective exercises, and display the merged result on the display.

Figure 11:
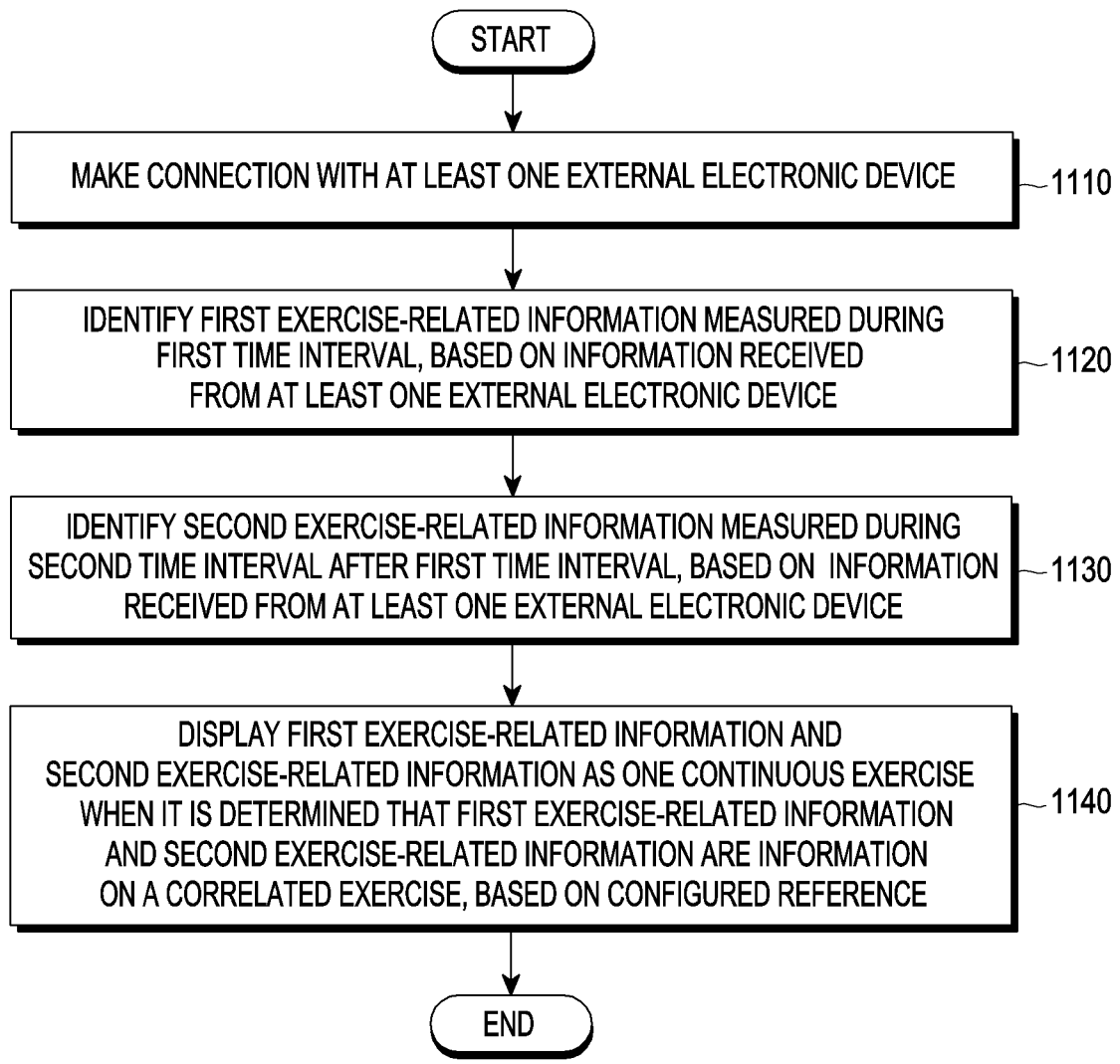
FIG. 11 is a flowchart illustrating an operation for merging exercise-related information by an electronic device according to an embodiment of the disclosure.

FIG. 11 is a flowchart illustrating the operation for merging exercise-related information by the electronic device according to an embodiment of the disclosure.

Referring to FIG. 11, in operation 1110, the electronic device 300 may be connected to at least one external electronic device (for example, the exercise machine 400). According to various embodiments, the electronic device 300 may be connected to at least one exercise machine 400 through a first communication module 370 to transmit connection information for sharing data, and may be connected to the at least one external electronic device through a second communication module 372 on the basis of the connection information for sharing data. The electronic device 300 may transmit and receive exercise-related information to and from the at least one exercise machine 400 through the second communication module 372. According to various embodiments, the connection information for sharing the data may include at least one of a Bluetooth Low Energy (BLE) address, a local name, or a user account.

In operation 1120, the electronic device 300 may identify first exercise-related information measured during a first time interval on the basis of information received from the at least one exercise machine 400.

In operation 1130, the electronic device 300 may identify second exercise-related information measured during a second time interval after the first time interval on the basis of information received from the at least one exercise machine 400.

When it is determined that the first exercise-related information and the second exercise-related information are information on exercises having correlation therebetween on the basis of a configured reference, the electronic device 300 may display the first exercise-related information and the second exercise-related information as one continuous exercise in operation 1140. According to various embodiments, the configured reference may include at least one of a start time or an end time of the first time interval or the second time interval, a type of the exercise machine corresponding to the first time interval or the second time interval, identification information of the exercise machine, exercise time information, location information, or environment information. Various embodiments of the configured reference will be described in detail with reference to FIGS. 18A to 27.

Figure 12:
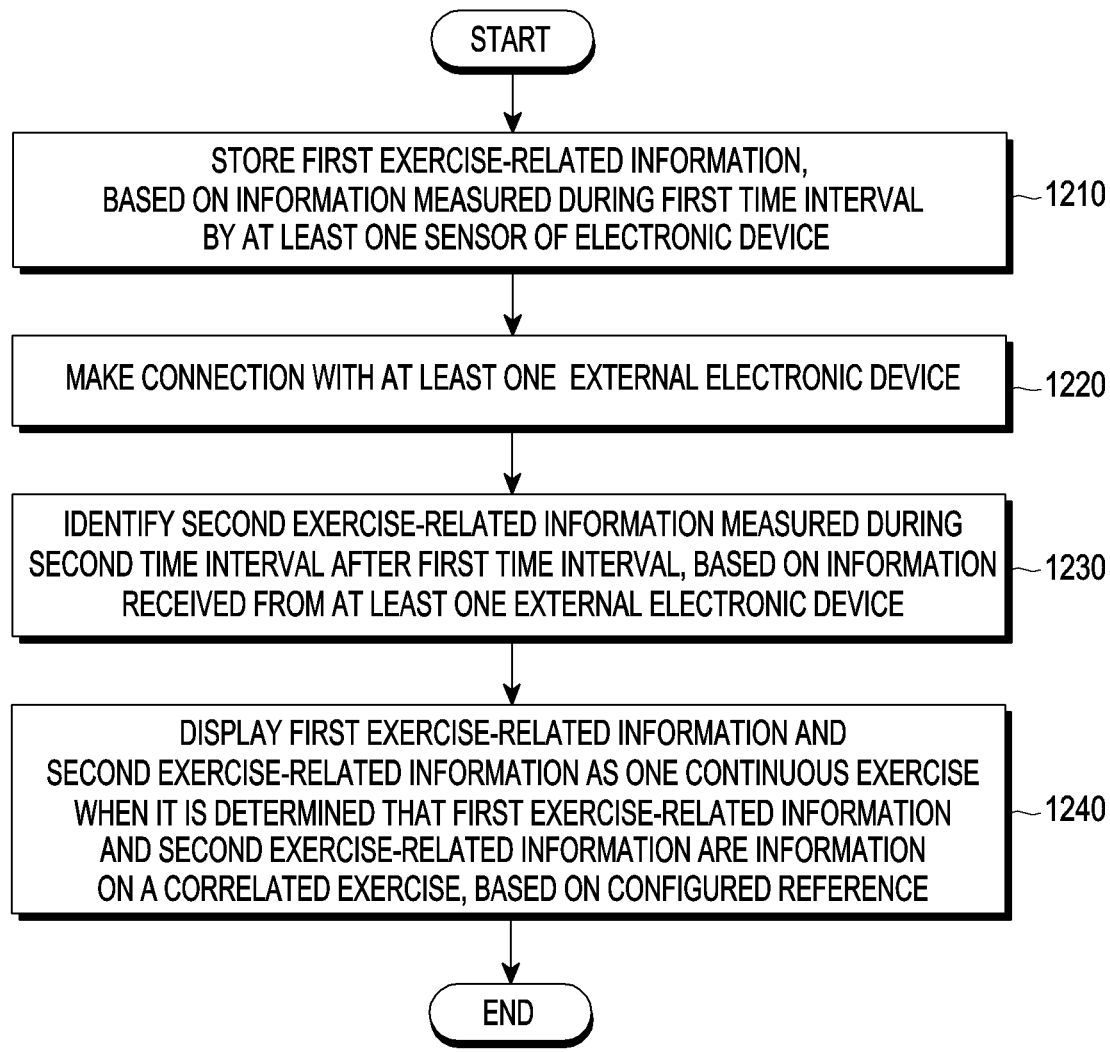
FIG. 12 is a flowchart illustrating an operation for merging exercise-related information by an electronic device according to an embodiment of the disclosure.

FIG. 12 is a flowchart illustrating an operation for merging exercise-related information by an electronic device according to an embodiment of the disclosure.

Referring to FIG. 12, in operation 1210, the electronic device 300 may store first exercise-related information in a memory (for example, the memory 330 of FIG. 3) on the basis of information measured during a first time interval by at least one sensor of the electronic device.

In operation 1220, the electronic device 300 may be connected to at least one external electronic device (for example, the exercise machine 400). According to various embodiments, the electronic device 300 may be connected to at least one exercise machine 400 through a first communication module 370 to transmit connection information for sharing data, and may be connected to the at least one external electronic device through a second communication module 372 on the basis of the connection information for sharing data. The electronic device 300 may transmit and receive exercise-related information to and from the at least one exercise machine 400 through the second communication module 372. According to various embodiments, the connection information for sharing the data may include at least one of a Bluetooth Low Energy (BLE) address, a local name, or a user account.

In operation 1230, the electronic device 200 may identify second exercise-related information measured during the second time interval after the first time interval on the basis of information received from the at least one external electronic device.

When it is determined that the first exercise-related information and the second exercise-related information are information on exercises having correlation therebetween on the basis of a configured reference, the electronic device 300 may display the first exercise-related information and the second exercise-related information as one continuous exercise in operation 1240. According to various embodiments, the configured reference may include at least one of a start time or an end time of the first time interval or the second time interval, a type of the exercise machine corresponding to the first time interval or the second time interval, identification information of the exercise machine, exercise time information, location information, or environment information. Various embodiments of the configured reference will be described in detail with reference to FIGS. 18A to 27.

Figure 13:
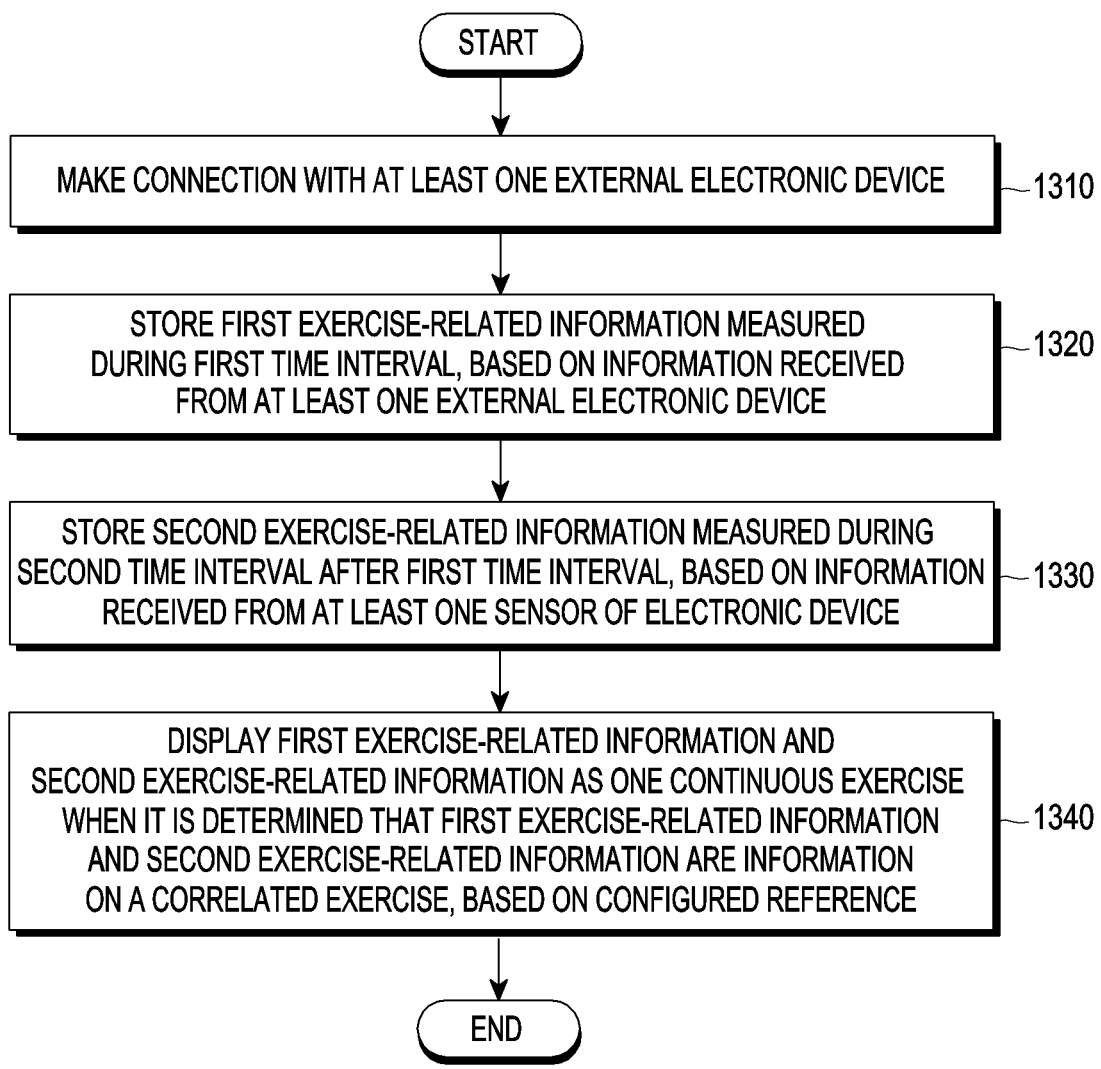
FIG. 13 is a flowchart illustrating an operation for merging exercise-related information by an electronic device according to an embodiment of the disclosure.

FIG. 13 is a flowchart illustrating the operation for merging exercise-related information by the electronic device according to an embodiment of the disclosure.

Referring to FIG. 13, in operation 1310, the electronic device 300 may be connected to at least one external electronic device (for example, the exercise machine 400). According to various embodiments, the electronic device 300 may be connected to at least one exercise machine 400 through a first communication module 370 to transmit connection information for sharing data, and may be connected to the at least one external electronic device through a second communication module 372 on the basis of the connection information for sharing data. The electronic device 300 may transmit and receive exercise-related information to and from the at least one exercise machine 400 through the second communication module 372. According to various embodiments, the connection information for sharing the data may include at least one of a Bluetooth Low Energy (BLE) address, a local name, or a user account.

In operation 1320, the electronic device 300 may store first exercise-related information measured during a first time interval in a memory (for example, the memory 330 of FIG. 3) on the basis of information received from the at least one external electronic device.

In operation 1330, the electronic device 300 may store second exercise-related information in a memory (for example, the memory 330 of FIG. 3) on the basis of information measured by at least one sensor of the electronic device during a second time interval after the first time interval.

When it is determined that the first exercise-related information and the second exercise-related information are information on exercises having correlation therebetween on the basis of a configured reference, the electronic device 300 may display the first exercise-related information and the second exercise-related information as one continuous exercise in operation 1340. According to various embodiments, the configured reference may include at least one of a start time or an end time of the first time interval or the second time interval, a type of the exercise machine corresponding to the first time interval or the second time interval, identification information of the exercise machine, exercise time information, location information, or environment information. Various embodiments of the configured reference will be described in detail with reference to FIGS. 18A to 27.

Hereinafter, detailed examples in which a plurality of pieces of exercise-related information is merged to one continuous exercise will be described in detail with reference to FIGS. 14 to 28. According to various embodiments, an exercise session may be the unit of exercise configured in each piece of exercise machine 400 in the following description. For example, when the user desires to do an exercise using the particular exercise machine 400, the user may configure at least one of an exercise time or an exercise mode through an input button located at the corresponding exercise machine 400 and input an exercise start. At this time, one exercise unit until the exercise ends after the exercise starts according to a user input may be referred to as an exercise session.

Figure 14:
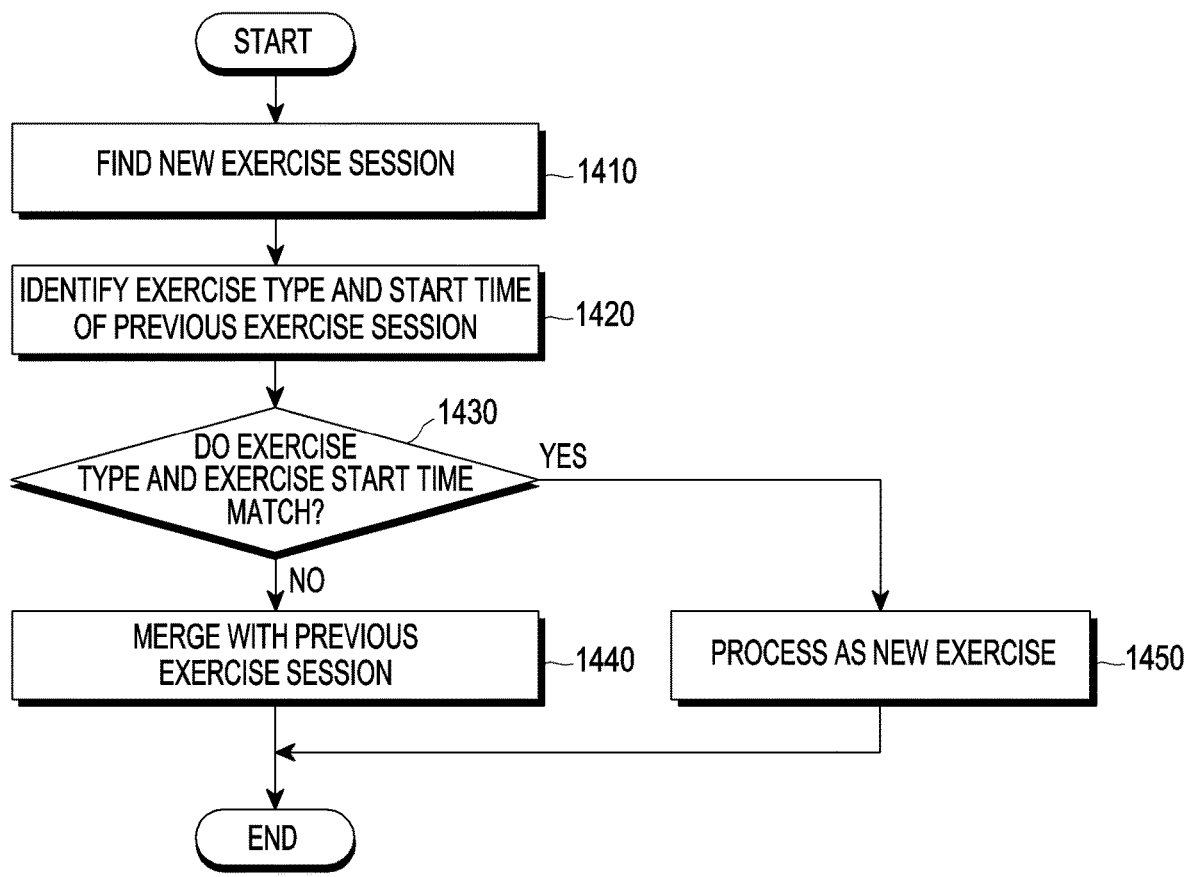
FIG. 14 is a flowchart illustrating an operation for merging exercise-related information by an electronic device according to an embodiment of the disclosure.

FIG. 14 is a flowchart illustrating an operation for merging exercise-related information by an electronic device according to an embodiment of the disclosure.

Referring to FIG. 14, when the electronic device 300 (for example, the first electronic device 210 or the second electronic device 220) identifies the start of a new exercise session in operation 1410, the electronic device 300 may identify time information of at least one of an actual exercise time (elapsed time) or an exercise start time transmitted from the exercise machine 400, an exercise machine type, and a unique machine number (for example, a BT address) in operation 1420.

According to various embodiments, the electronic device 300 may determine whether the exercise is the same as the previous exercise session on the basis of the identified information in operation 1430. For example, when the exercise type and the exercise start time match on the basis of the identified information, the electronic device 300 may determine that the new exercise is the same as the previous exercise. The electronic device 300 may process the two exercises as one exercise on the basis of information related to the two exercises and store the exercise or display the same on the display in operation 1440. According to various embodiments, when the electronic device 300 (for example, the first electronic device 210 or the second electronic device 220) determines that the new exercise session is different from the previous exercise session, the electronic device 300 may store the new exercise session to be different from the previous exercise session or display the same on the display in operation 1450.

Figure 15:
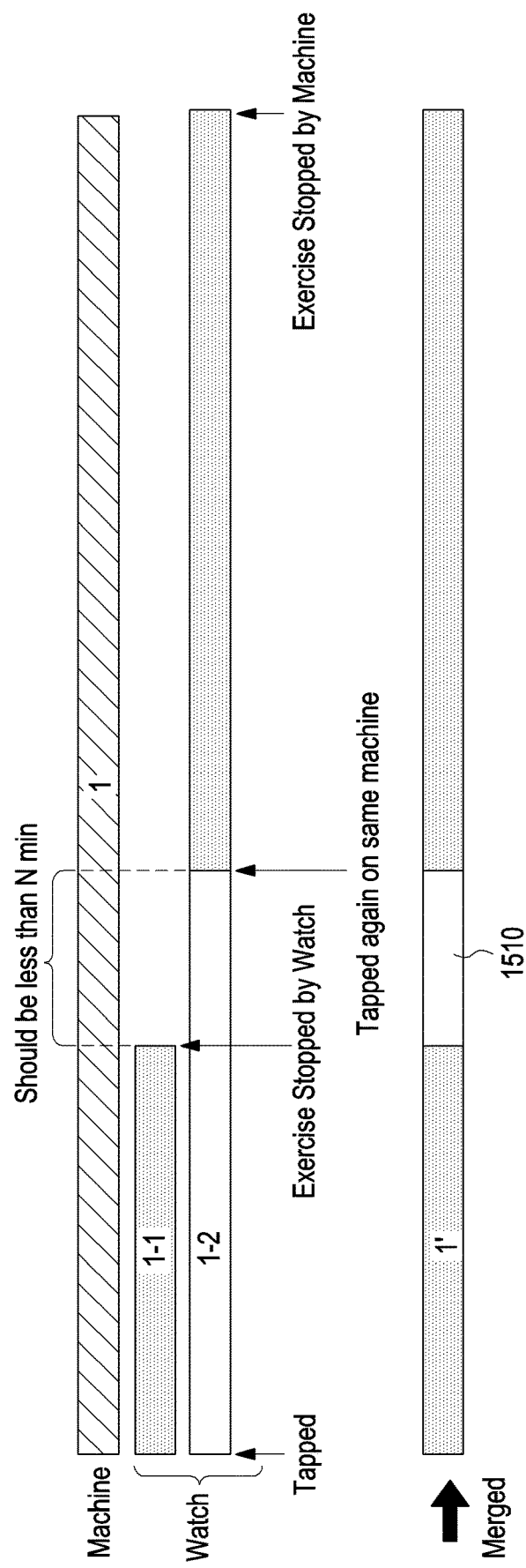
FIG. 15 illustrates an example of an operation for merging exercise-related information by an electronic device according to an embodiment of the disclosure.

For example, as illustrated in FIG. 15, when the electronic device 300 (for example, the second electronic device 220) stores exercise record 1-1 and then stores exercise record 1-2 in the same piece of exercise machine 400 after a predetermined time on the basis of exercise-related information received from the exercise machine 400, the electronic device 300 may analyze the stored data 1-1 and 1-2, detect whether the exercises are the same as each other, and merge the two data to generate data 1'.

FIG. 15 illustrates an example of an operation for merging exercise-related information by an electronic device according to an embodiment of the disclosure.

Referring to FIG. 15, when two pieces of data are merged, if there is an average value of the previous exercise (average value of exercise 1-1) and an average value of all exercises or an average value when the new exercise starts (average value when exercise 1-2 starts), data in a time interval 1510 in which measurement is stopped may be inferred using the average value and expressed in a graph, or may be inferred using a continuously measured HR value.

According to various embodiments, even though transmission of data is stopped during a time interval 1510 in which measurement is stopped between two time intervals 1-1 and 1-2 merged in FIG. 15, data in the time interval 1510 in which measurement is stopped may be inferred and provided using information that the electronic device 300 or the exercise machine 400 already knows.

For example, according to various embodiments, information that is already known by the electronic device 300 or the exercise machine 400 may include at least one of calories of the last data in time interval 1-1, calories of the first data in time interval 1-2, an interval between the last elapsed time in time interval 1-1 and the elapsed time of the first data of time interval 1-2 (for example, a time interval 1510 in which measurement is stopped), and a continuously measured HR.

For example, according to various embodiments, information that may be known by the electronic device 300 or the exercise machine 400 may include at least one of avg. power, avg. cadence, and avg. speed in time interval 1-1, avg. power, avg. cadence, and avg. speed when time interval 1-2 starts, and avg. power, avg. cadence, and avg. speed in interval 1.

According to various embodiments, through an algorithm for filling in the time interval 1510 in which measurement is stopped when two pieces of data merge, an average speed or pedaling cadence in the time interval in which measurement is stopped may be calculated using at least one of a difference between distance information and an elapsed time last received from the previous exercise session and distance information and an elapsed time first received from the new exercise session, a previously measured stride length, and a wheel size. According to various embodiments, the time interval 1510 in which measurement is stopped may be simply filled with the speed or the pedaling cadence, or the speed or the pedaling cadence in the corresponding interval may be more precisely estimated by reflecting a change in the HR in the value in the corresponding interval to control the value.

Figure 16A:
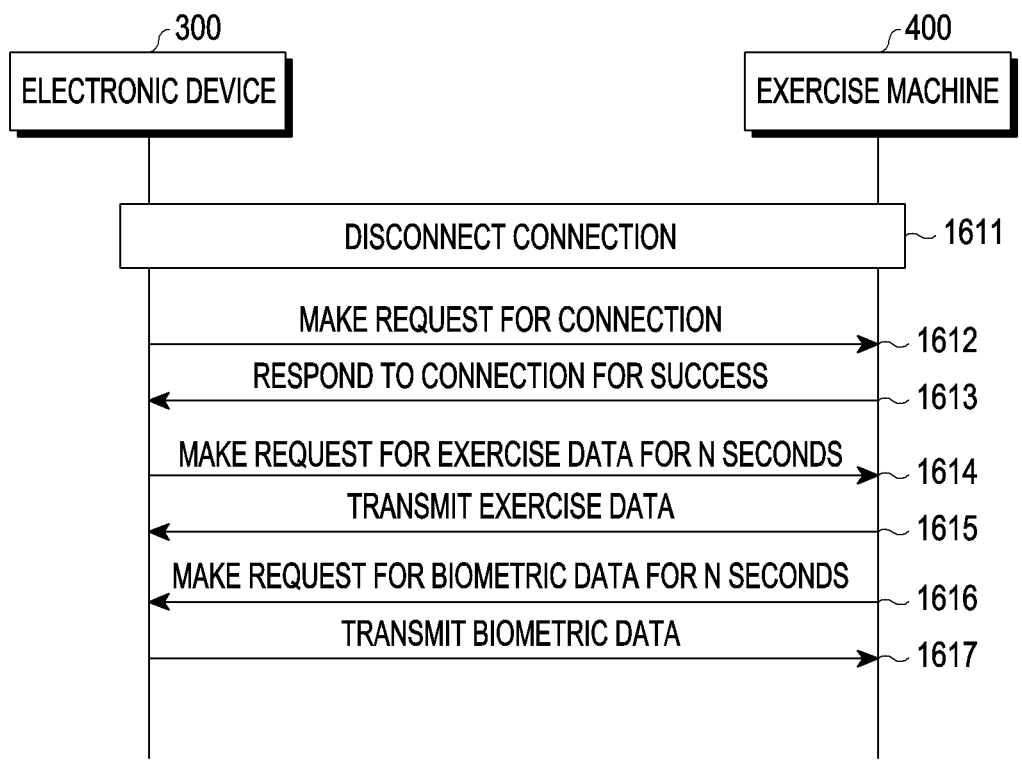
FIG. 16A is a flowchart illustrating a method of exchanging data when an electronic device is reconnected to an exercise machine according to an embodiment of the disclosure.

FIG. 16A is a flowchart illustrating a data exchange method when an electronic device is reconnected to an exercise machine according to an embodiment of the disclosure.

Figure 16B:
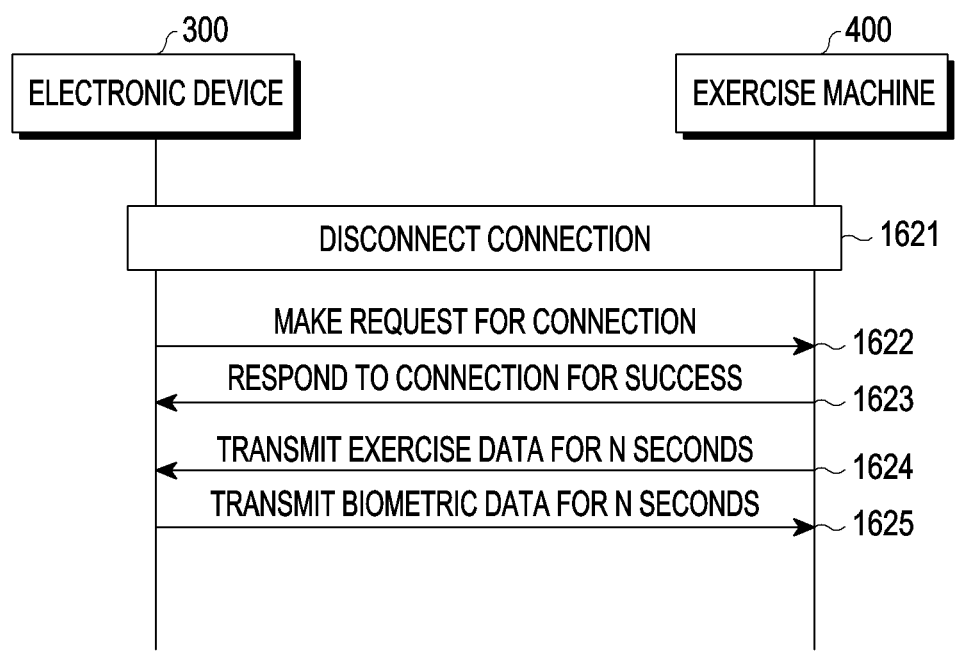
FIG. 16B is a flowchart illustrating a method of exchanging data when an electronic device is reconnected to an exercise machine according to an embodiment of the disclosure.

FIG. 16B is a flowchart illustrating a data exchange method when an electronic device is reconnected to an exercise machine according to an embodiment of the disclosure.

FIGS. 16A and 16B illustrate a method of reconstructing lost data through a data exchange protocol designated between the electronic device 300 (for example, the second electronic device 220) and the exercise machine 400.

Referring to FIGS. 16A and 16B, data lost for a time (N minutes) during which the previous connection between the electronic device 300 and the exercise machine 400 is disconnected may be reconstructed using a designated protocol for exchanging previous data between the electronic device 300 and the exercise machine 400. For example, a device that requires data may first make a request for data in a specific time such as 1 to N seconds/N to M seconds, and a device that receives the request may transmit the data in the corresponding period or may collect data generated before the connection and immediately transmit the data at the moment the connection is made.

Referring to FIG. 16A, when the connection is disconnected for a specific time in operation 1611, the electronic device 300 may make a request for the connection to the exercise machine 400 in operation 1612.

In operation 1613, the exercise machine 400 may respond to connection success.

In operation 1614, the electronic device 300 may make a request for exercise data for N seconds to the exercise machine 400.

In operation 1615, the exercise machine 400 may transmit exercise data to the electronic device 300.

In operation 1616, the exercise machine 400 may make a request for biometric data (for example, HR data) for N seconds to the electronic device 300.

In operation 1617, the electronic device 300 may transmit the requested biometric data to the electronic device 300.

Referring to FIG. 16B, when the connection is disconnected for a specific time in operation 1621, the electronic device 300 may make a request for the connection to the exercise machine 400 in operation 1622.

In operation 1623, the exercise machine 400 may respond to connection success.

In operation 1624, the exercise machine 400 may transmit exercise data to the electronic device 300. In operation 1625, the electronic device 300 may transmit biometric data (for example, HR data) to the exercise machine 400. According to various embodiments, since the electronic device 300 and the exercise machine 400 can know the time at which the connection is disconnected, data before the time at which the connection is disconnected may be transmitted at a time point of the reconnection. According to various embodiments, the order of operations 1624 and 1625 may be changed or simultaneously performed.

Figure 16C:
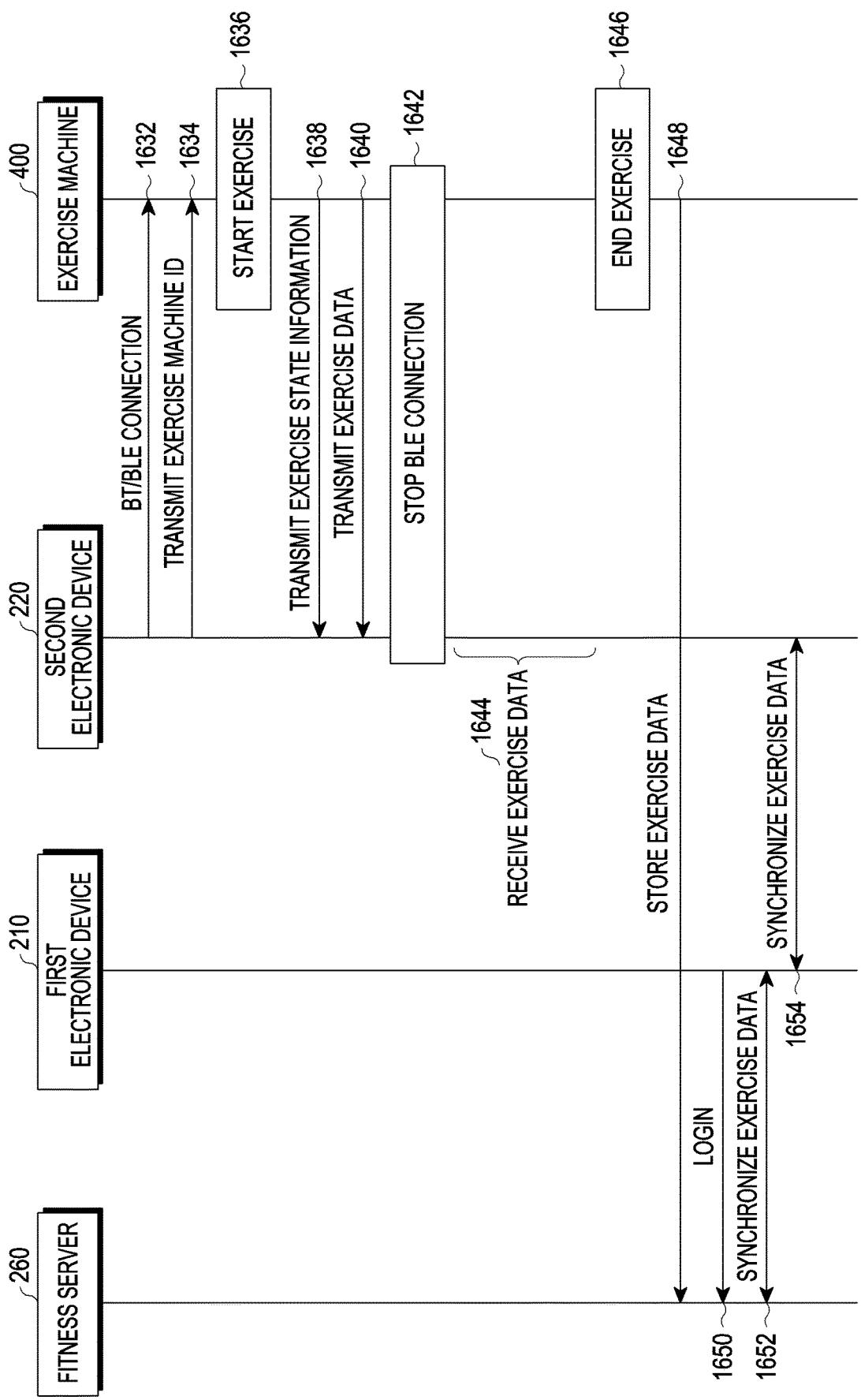
FIG. 16C is a flowchart illustrating a data reconstruction operation through a fitness server by an electronic device according to an embodiment of the disclosure.

FIG. 16C is a flowchart illustrating a data reconstruction operation through a fitness server by an electronic device according to an embodiment of the disclosure.

FIG. 16C illustrates a method of reconstructing missing data through the fitness server 260.

According to various embodiments, when the electronic device tags the exercise machine 400 during the exercise, the electronic device may reconstruct missing data by loading data on the exercise before the tagging from the fitness server 260 on the basis of an ID for access to the exercise machine 400 and performing synchronization even after the exercise ends. According to various embodiments, a time point at which the electronic device links with the fitness server may be after a time point at which exercise data is uploaded to the fitness server after the exercise ends.

Referring to FIG. 16C, in operation 1632, the second electronic device 220 (for example, a wearable electronic device) may be connected to the exercise machine 400 through BT/BLE communication.

In operation 1634, the second electronic device 220 may perform a login operation by transmitting an exercise machine ID to the connected exercise machine 400.

When the exercise starts through the exercise machine 400 in operation 1636, the exercise machine 400 may transmit exercise state information to the second electronic device 220 in operation 1638. According to various embodiments, the exercise machine 400 may transmit exercise data according to the exercise to the second electronic device 220 in operation 1640.

According to various embodiments, the second electronic device 220 may release the connection with the exercise machine 400 in operation 1642. For example, in the state in which the connection between the second electronic device 220 and the exercise machine 400 is released, the user may drive the exercise machine 400 to continuously do the exercise. In this case, since the connection with the exercise machine 400 is disconnected during the exercise, the second electronic device 220 cannot receive exercise data from the exercise machine 400 any more in operation 1644.

According to the use of the exercise machine 400 ending, driving of the exercise machine 400 may be stopped in operation 1646, and the exercise machine 400 may transmit exercise data to the fitness server 260 to store the exercise data in operation 1648. According to various embodiments, when the user continuously does the exercise even after the connection is disconnected and then ends the exercise, the exercise machine 400 may store exercise data in a user's account used for logging in the fitness server 260.

After the exercise ends, the first electronic device 210 (or the second electronic device 220) may log in the fitness server 260 in operation 1650 and then receive exercise data from the fitness server 260 in operation 1652.

According to various embodiments, in operation 1654, the first electronic device 210 may be synchronized with the second electronic device 220. For example, the first electronic device 210 and the second electronic device 220 may compare stored exercise data and reconstruct missing data.

Figure 17A:
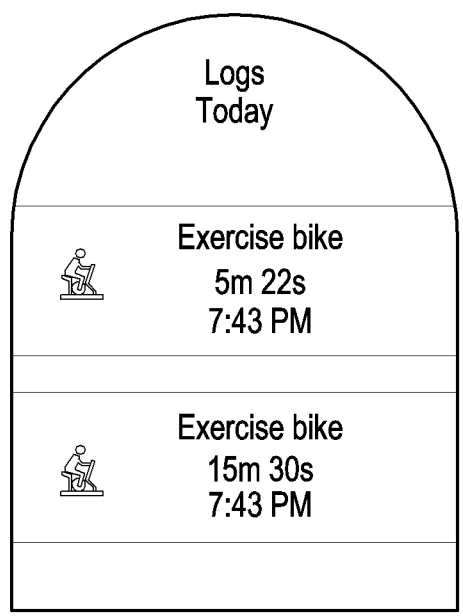
FIG. 17A illustrates a non-merged result screen of exercises of an electronic device according to an embodiment of the disclosure.

FIG. 17A illustrates a non-merged result screen of exercises of an electronic device according to an embodiment of the disclosure.

Figure 17B:
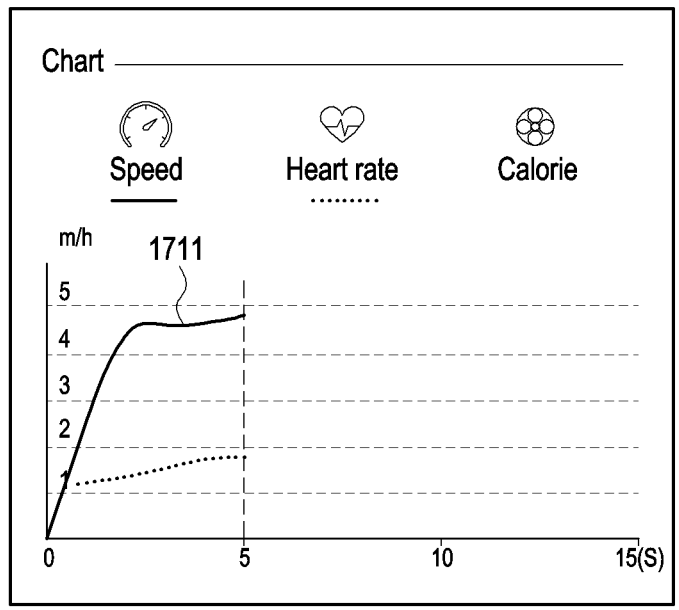
FIG. 17B illustrates a non-merged result screen of exercises of an electronic device according to an embodiment of the disclosure.

FIG. 17B illustrates a non-merged result screen of exercises of an electronic device according to an embodiment of the disclosure.

Figure 17C:
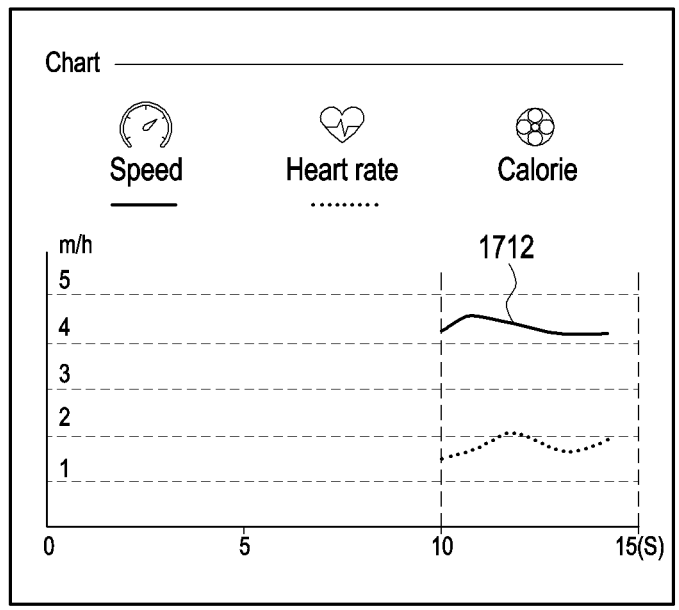
FIG. 17C illustrates a non-merged result screen of exercises of an electronic device according to an embodiment of the disclosure.

FIG. 17C illustrates a non-merged result screen of exercises of an electronic device according to an embodiment of the disclosure.

Figure 18A:
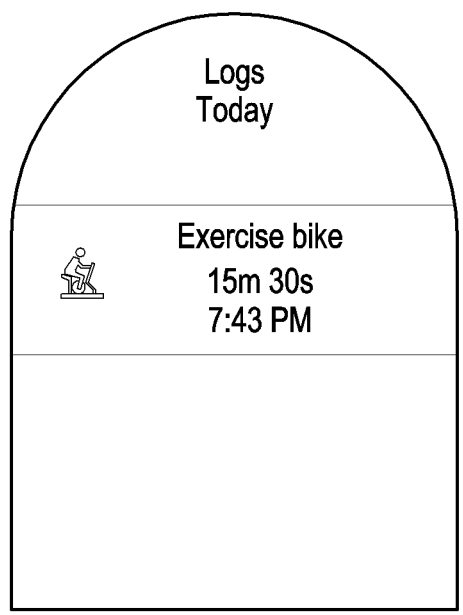
FIG. 18A illustrates a result screen of exercises of an electronic device merged from FIGS. 17A, 17B, and 17C according to an embodiment of the disclosure
Figure 18B:
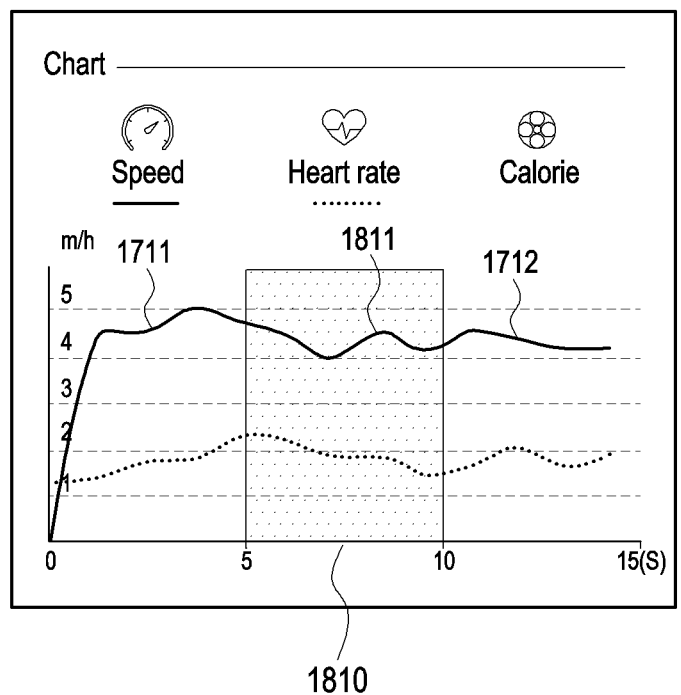
FIG. 18B illustrates a result screen of exercises of an electronic device merged from FIGS. 17A, 17B, and 17C according to an embodiment of the disclosure.

FIG. 18A illustrates a result screen of exercises of the electronic device merged from FIGS. 17A, 17B, and 17C according to an embodiment of the disclosure and FIG. 18B illustrates a result screen of exercises of the electronic device merged from FIGS. 17A, 17B, and 17C according to an embodiment of the disclosure.

Referring to FIG. 17A, the electronic device 300 may continuously display the same type of exercise such as exercise bike on the display. Two exercise results may have different elapsed times but the same start time.

Referring to FIG. 17B, a resultant graph 1711 for the indoor bike exercise that is measured first and indicates upper data among two indoor bike exercise data illustrated in FIG. 17A is illustrated, and FIG. 17C illustrates a resultant graph 1712 for the indoor bike exercise that is measured later and indicates lower data among two indoor bike exercise data illustrated in FIG. 17A. The two data are the same type of data, which indicates one exercise done by the user, but exercise results thereof are separately displayed.

Referring to FIG. 18A, the two exercise data separately displayed for the same type of exercise illustrated in FIG. 17A are merged and displayed as one exercise. According to various embodiments, referring to FIG. 18B, after the two exercise data are merged, a predicted group 1811 may be used for a time interval 1810 during which measurement is stopped.

Figure 19:
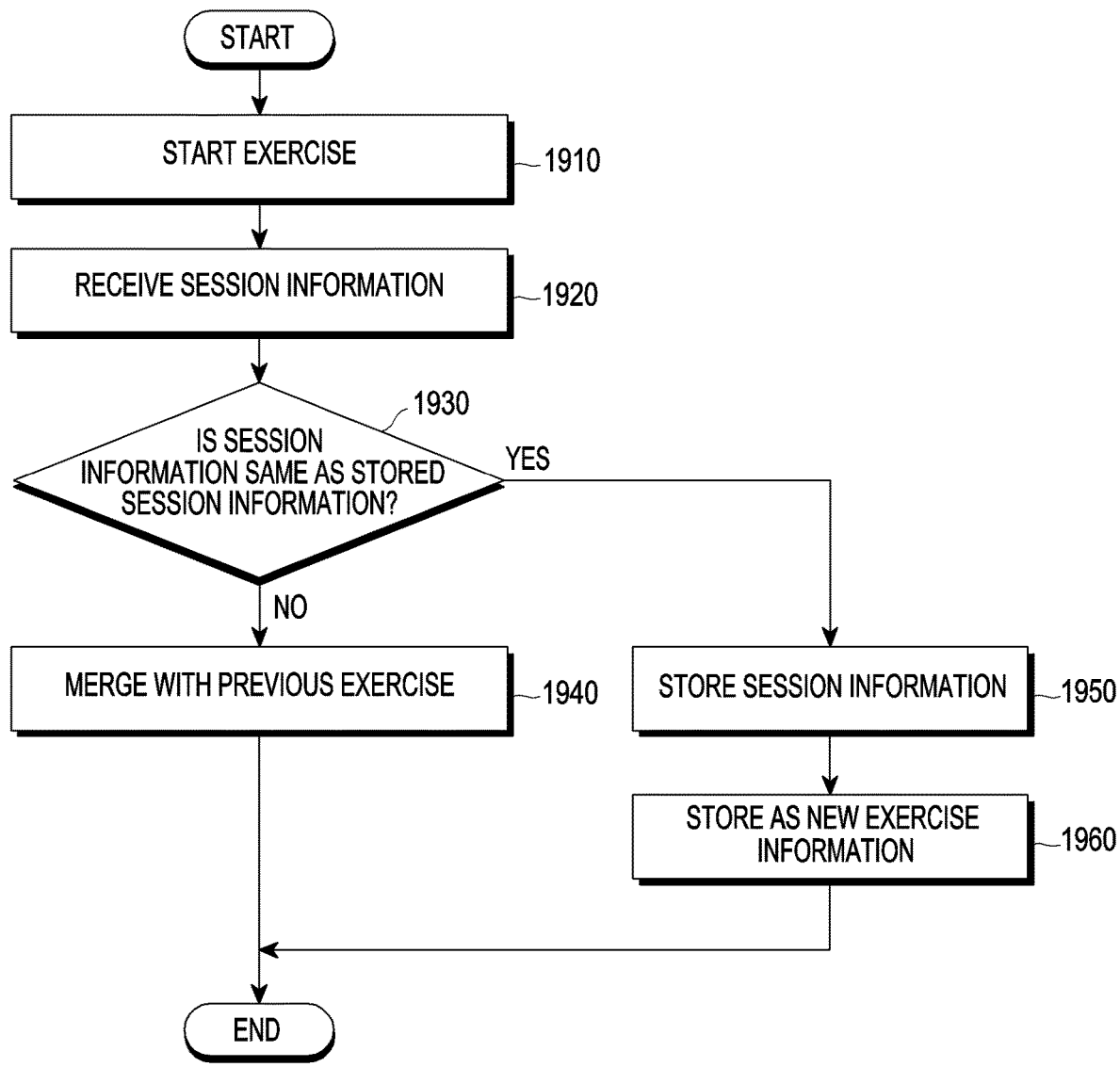
FIG. 19 is a flowchart illustrating an operation for merging exercise-related information by an electronic device according to an embodiment of the disclosure.

FIG. 19 is a flowchart illustrating an operation for merging exercise-related information by an electronic device according to an embodiment of the disclosure.

Referring to FIG. 19, it may be determined that the exercises have different start times by inferring the start times on the basis of the exercise time of the exercise machine 400 and the exercises may be merged by receiving additional exercise session information from the exercise machine 400.

According to various embodiments, when the electronic device 300 (for example, the first electronic device 210 or the second electronic device 200) receives exercise information from the exercise machine 400 through the connection with the exercise machine using short-range communication, if the connected exercise machine 400 is being used for the exercise, the exercise machine 400 may receive information on an exercise session (session ID) and when the previously stored exercise has the same or similar information (for example, the same session information (for example, session ID)), merge the exercise. According to various embodiments, the electronic device 300 may acquire exercise session information from the exercise machine 400. According to various embodiments, when starting a new exercise, the electronic device 300 (for example, the second electronic device 200) may transmit new exercise information to the exercise machine 400 and read again the exercise session information from the exercise machine 400 to use the same if necessary.

When the exercise starts in operation 1910, the electronic device 300 may receive exercise session information from the exercise machine 400 in operation 1920.

The electronic device 300 may determine whether the exercise session information received from the exercise machine 400 is the same as exercise session information stored in the electronic device 300 in operation 1930 and when the received exercise session information is the same as the stored exercise session information, merge the exercise with the previous exercise in operation 1940.

The electronic device 300 may determine whether the exercise session information received from the exercise machine 400 is the same as exercise session information stored in the electronic device 300 in operation 1930 and when the received exercise session information is not the same as the stored exercise session information, store new exercise session information in operation 1950.

In operation 1960, the electronic device 300 may store information corresponding to the stored exercise session information as new exercise information.

Figure 20:
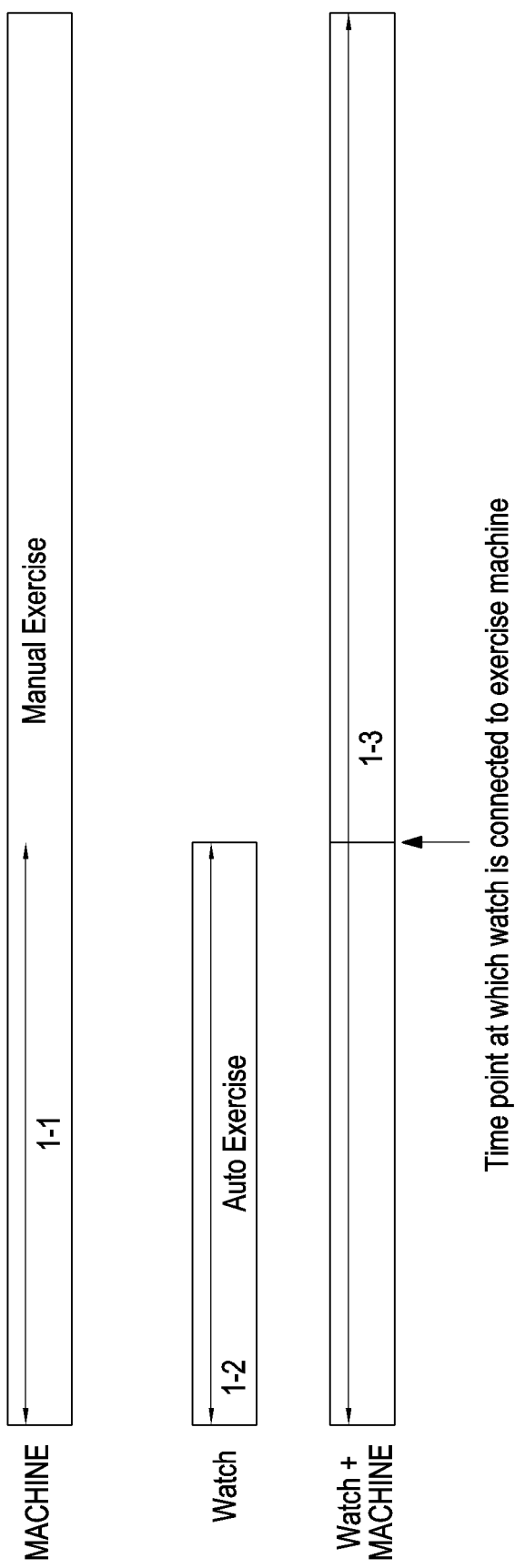
FIG. 20 illustrates an example of an operation for merging exercise-related information by an electronic device according to an embodiment of the disclosure.

FIG. 20 illustrates an example of an operation for merging exercise-related information by an electronic device according to an embodiment of the disclosure.

Referring to FIG. 20, when an exercise time of an automatic exercise does not overlap an exercise time of a manual exercise, the electronic device 30 may merge automatic exercise data with manual exercise data.

When the user starts the exercise in the state in which the connection with the exercise machine 400 is not made, the electronic device 300 (for example, the second electronic device 220) may sense various pieces of data in the state in which the automatic exercise is recognized. Since the exercise machine 400 and the electronic device 300 are not connected to each other, they may conduct exercises 1-1 and 1-2, respectively. According to various embodiments, when the exercises are processed to be separately conducted and the connection between the exercise machine 400 and the electronic device 300 is made during the exercise using the exercise machine 400 as illustrated in FIG. 19, the electronic device 300 may store two exercises.

According to various embodiments, when the exercise machine 400 is connected to the electronic device 300, the electronic device 300 may determine exercise times and when it is determined that the previous automatic exercise 1-2 is the same as the exercise 1-1 through the exercise machine 400, merge the exercises into one exercise 1-3.

Figure 21:
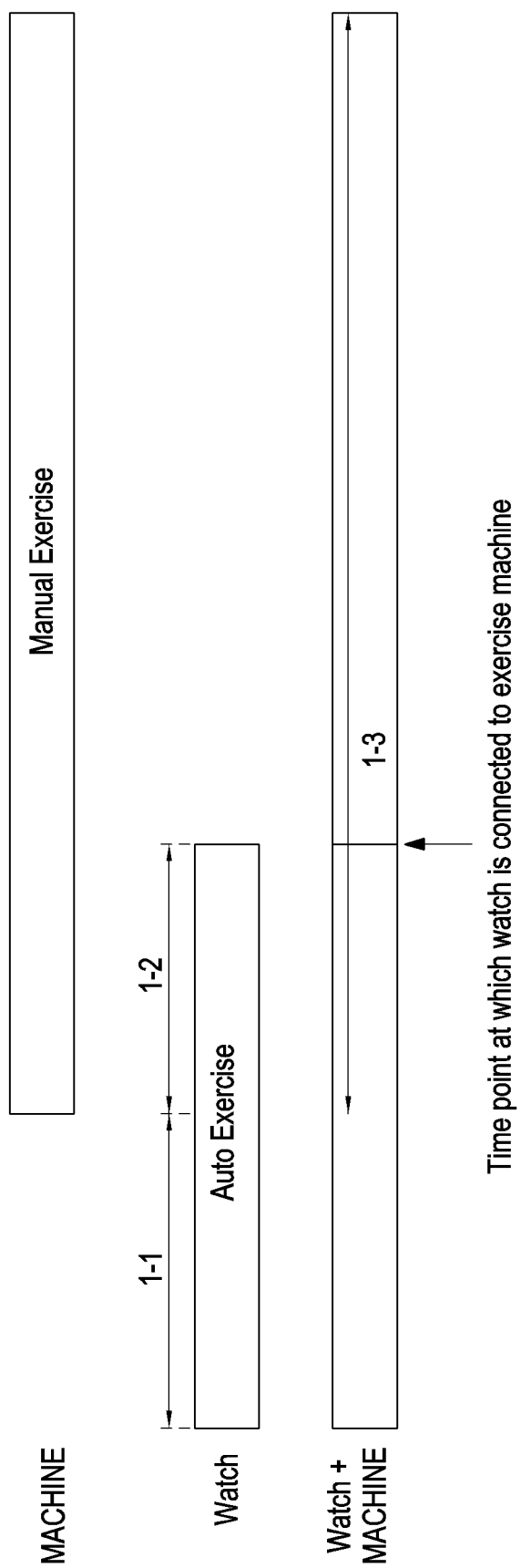
FIG. 21 illustrates an example of an operation for merging exercise-related information by an electronic device according to an embodiment of the disclosure.

FIG. 21 illustrates an example of an operation for merging exercise-related information by an electronic device according to an embodiment of the disclosure.

Referring to FIG. 21, when exercise times of the automatic exercise and the manual exercise overlap each other, the electronic device 300 may merge automatic exercise data with manual exercise data.

According to various embodiments, when the user lightly runs on a track within a GYM, continuously starts an exercise using the exercise machine 400, and makes a connection with the exercise machine 400 after N minutes, exercise-related information may be stored in the state in which exercise times thereof partially overlap. According to various embodiments, when a merging method is used therefor, the electronic device 300 may control an automatically recognized exercise period and may store data through merger with exercise using the exercise machine 400 in some exercise intervals (interval 1-2) that are recognized as automatic exercise.

Figure 22:
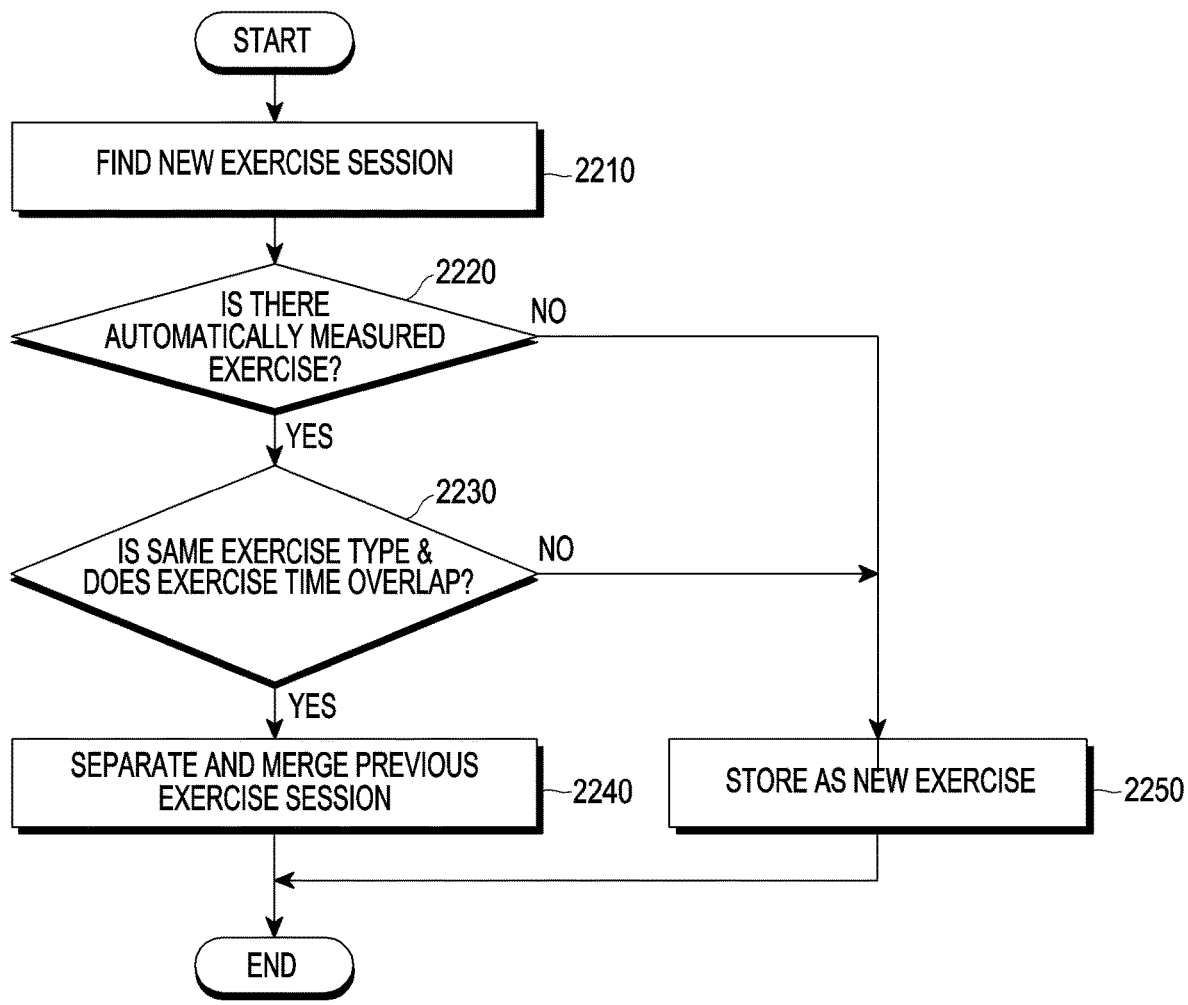
FIG. 22 is a flowchart illustrating an operation for merging exercise-related information by an electronic device according to an embodiment of the disclosure.

FIG. 22 is a flowchart illustrating an operation for merging exercise-related information by an electronic device according to an embodiment of the disclosure.

Referring to FIG. 22, when the electronic device 300 finds a new exercise session in operation 2210, the electronic device 300 may determine whether there is an automatically measured exercise in operation 2220.

When there is the automatically measured exercise on the basis of the determination result, the electronic device 300 may determine whether the exercises are the same type exercises and whether exercise times thereof overlap in operation 2230.

When the exercises are the same type exercises and the exercise times overlap on the basis of the determination result, the electronic device 300 may separate the exercise from a previous exercise session and merge them in operation 2240.

When the exercises are not the same type exercises and the exercise times do not overlap on the basis of the determination result, the electronic device 300 may store the exercise corresponding to the newly found exercise session as a new exercise and display the same on the display in operation 2250.

Figure 23:
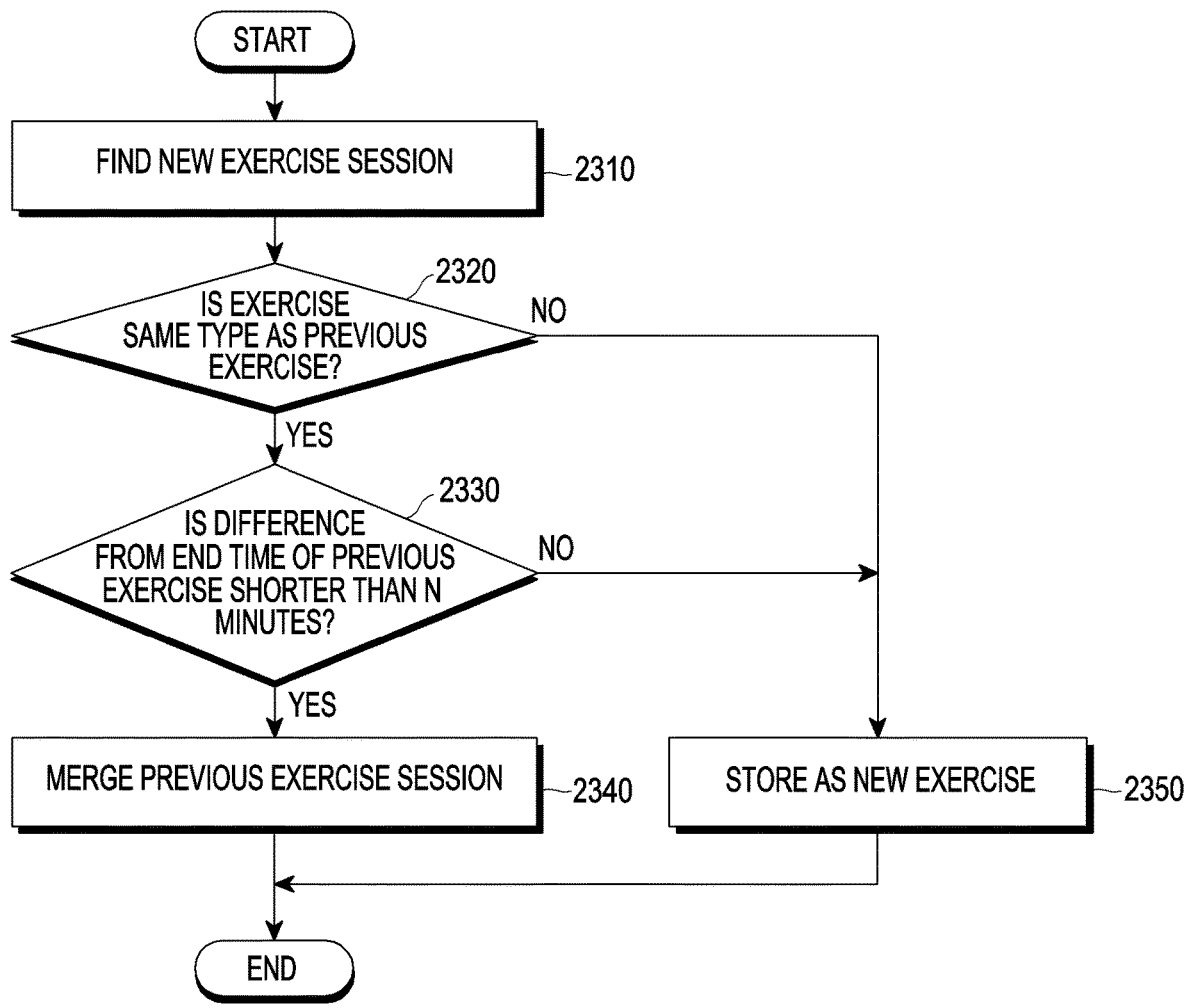
FIG. 23 is a flowchart illustrating an operation for merging exercise-related information by an electronic device according to an embodiment of the disclosure.

FIG. 23 is a flowchart illustrating the operation for merging exercise-related information by the electronic device according to an embodiment of the disclosure.

Referring to FIG. 23, the electronic device 300 (for example, the second electronic device 220) may merge exercise data received from the same type of a plurality of pieces of exercise machine 400.

According to various embodiments, the user may make a connection with a first piece of exercise machine to do an exercise and end the exercise due to malfunction of the machine or for another reason. Thereafter, the user may move to a second piece of exercise machine of the same type located near the first exercise machine and make a connection between the electronic device 300 and the second exercise machine to do an exercise. In this case, the electronic device 300 may recognize exercise conducted through a new connection as another exercise, but may merge the exercises to one exercise according to various embodiments.

When the electronic device 300 finds a new exercise session in operation 2310, the electronic device 300 may determine whether the exercise is the same type as the previous exercise in operation 2320.

When it is determined that the exercise is the same type on the basis of the determination result, the electronic device 300 may determine whether a difference from an end time of the previous exercise is shorter than N minutes in operation 2330. When it is determined that the difference is shorter than N minutes on the basis of the determination result, the electronic device 300 may merge the exercise with the previous exercise session in operation 2340.

When it is determined that the exercise is not the same type ("No" of operation 2320) or that the difference from the end time of the previous exercise is shorter than N minutes ("No" of operation 2330) on the basis of the determination result, the electronic device 300 may store the exercise corresponding to the found new exercise session as new exercise and display the new exercise in operation 2350.

Figure 24A:
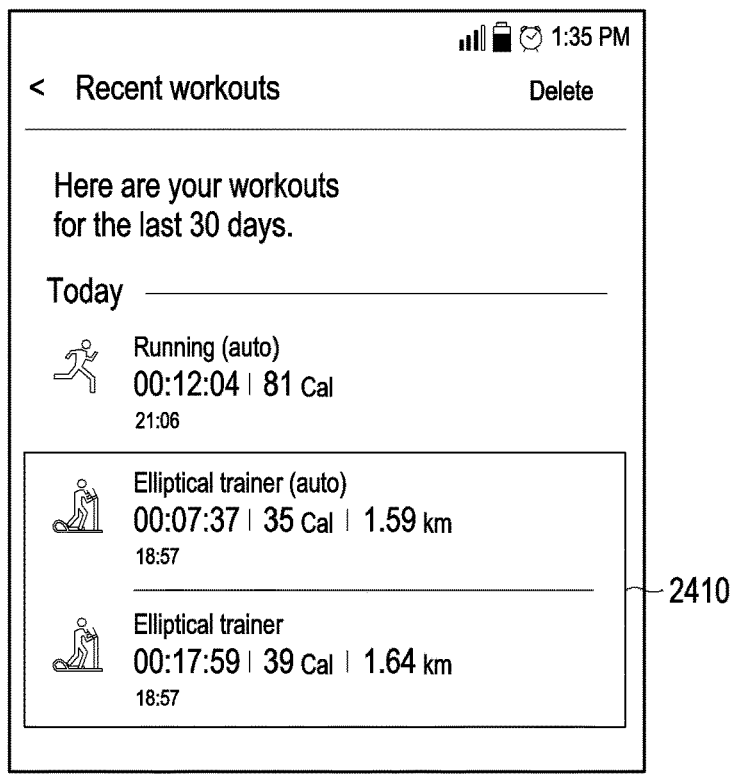
FIG. 24A illustrates a result screen of exercises before merger in an electronic device according to an embodiment of the disclosure.

FIG. 24A illustrates a result screen of exercises before merger in an electronic device according to an embodiment of the disclosure.

Figure 24B:
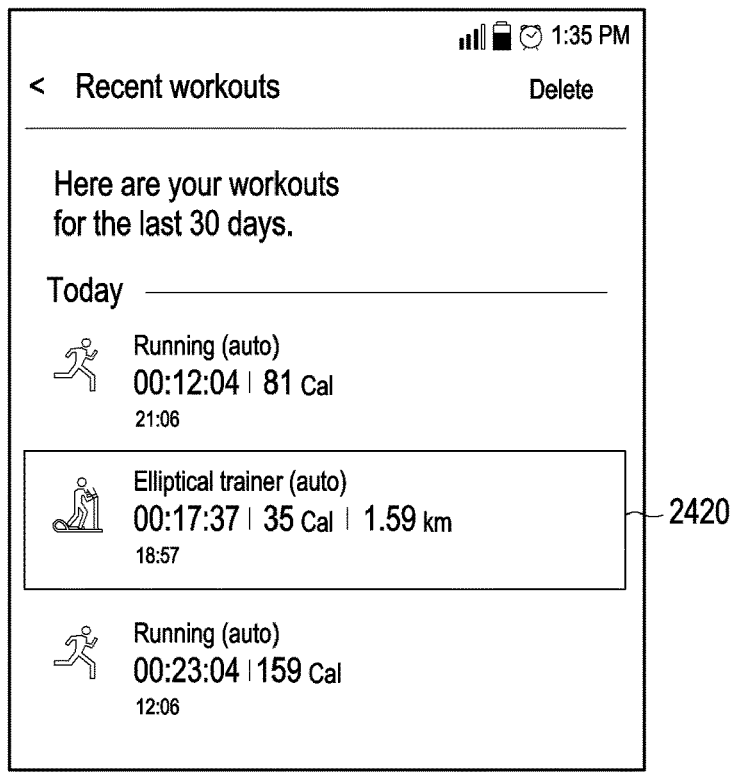
FIG. 24B illustrates a result screen of merged exercises in an electronic device according to an embodiment of the disclosure.

FIG. 24B illustrates a result screen of merged exercises in an electronic device according to an embodiment of the disclosure.

Figure 25A:
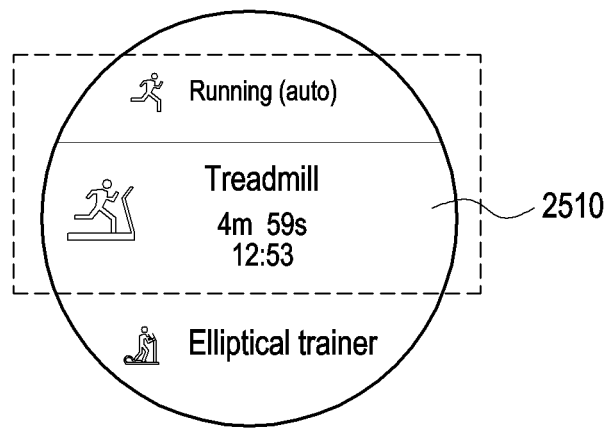
FIG. 25A illustrates a result screen of exercises before merger in an electronic device according to an embodiment of the disclosure.

FIG. 25A illustrates a result screen of exercises before merger in an electronic device according to an embodiment of the disclosure.

Figure 25B:
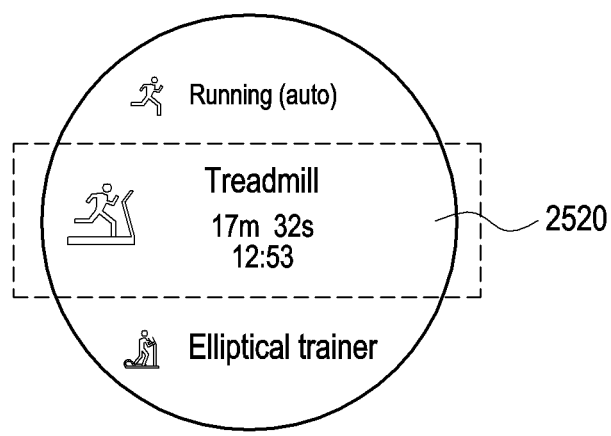
FIG. 25B illustrates a result screen of merged exercises in an electronic device according to an embodiment of the disclosure.

FIG. 25B illustrates a result screen of merged exercises in an electronic device according to an embodiment of the disclosure.

Referring to FIGS. 24A and 24B, according to various embodiments, when a connection with the exercise machine is not made, stored automatic exercise and manual exercise are displayed as separate exercises as indicated by reference numeral 2410 in a viewpoint of the electronic device 300 (for example, the first electronic device 210), but the exercises are the same exercise in a viewpoint of the user, so it may be more useful to display the exercises as one exercise as indicated by reference numeral 2420.

Referring to FIGS. 25A and 25B, according to various embodiments, when a connection with the exercise machine is not made, stored automatic exercise and manual exercise are displayed as separate exercises as indicated by reference numeral 2510 in a viewpoint of the electronic device 300 (for example, the first electronic device 210), but the exercises are the same exercise in a viewpoint of the user, so it may be more useful to display the exercises as one exercise as indicated by reference numeral 2520.

Figure 26:
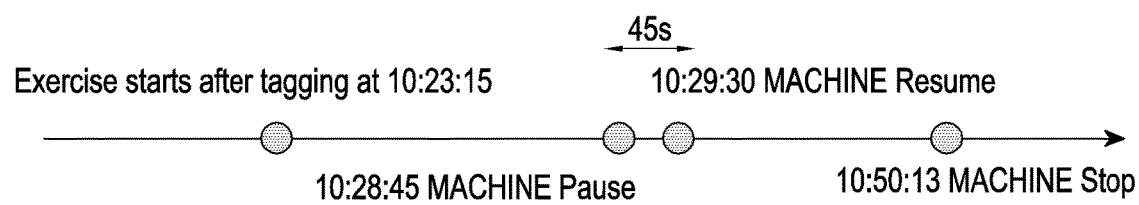
FIG. 26 illustrates an example of an operation for processing a pause section by an electronic device according to an embodiment of the disclosure.

FIG. 26 illustrates an example of an operation for processing a pause section of exercise in an electronic device according to an embodiment of the disclosure.

Referring to FIG. 26, the electronic device 300 may merge data when the exercise machine 400 includes the pause section.

According to various embodiments, the electronic device 300 (for example, the second electronic device 220) may also store an entire exercise time including a rest during exercise rather processing only a real exercise time. However, the exercise machine 400 transmits data except for the pause section in which the exercise is stopped, and thus the electronic device 300 may need to process the pause section.

According to various embodiments, referring to FIG. 26, the electronic device 300 may start exercise by tagging on the exercise machine 400 at 10:23:15. After pausing at 10:28:45, the exercise machine 400 may resume exercise at 10:29:30 after 45 seconds and finally end the exercise at 10:50:13.

According to various embodiments, the electronic device 300 may predict and use 10:29:30 that is a start time of second exercise after a pause on the basis of a time required for data first received at 10:23:15 after tagging and calculate 45 seconds which is a pause time on the basis of a time of 10:50:13 at which the last data is received and a real exercise time of 1573s. According to various embodiments, the electronic device 300 may store a pause/resume period in a memory on the basis of information received from the exercise machine 400 and predict and show a start time on the basis of an end time with reference to the pause/resume period.

Figure 27:
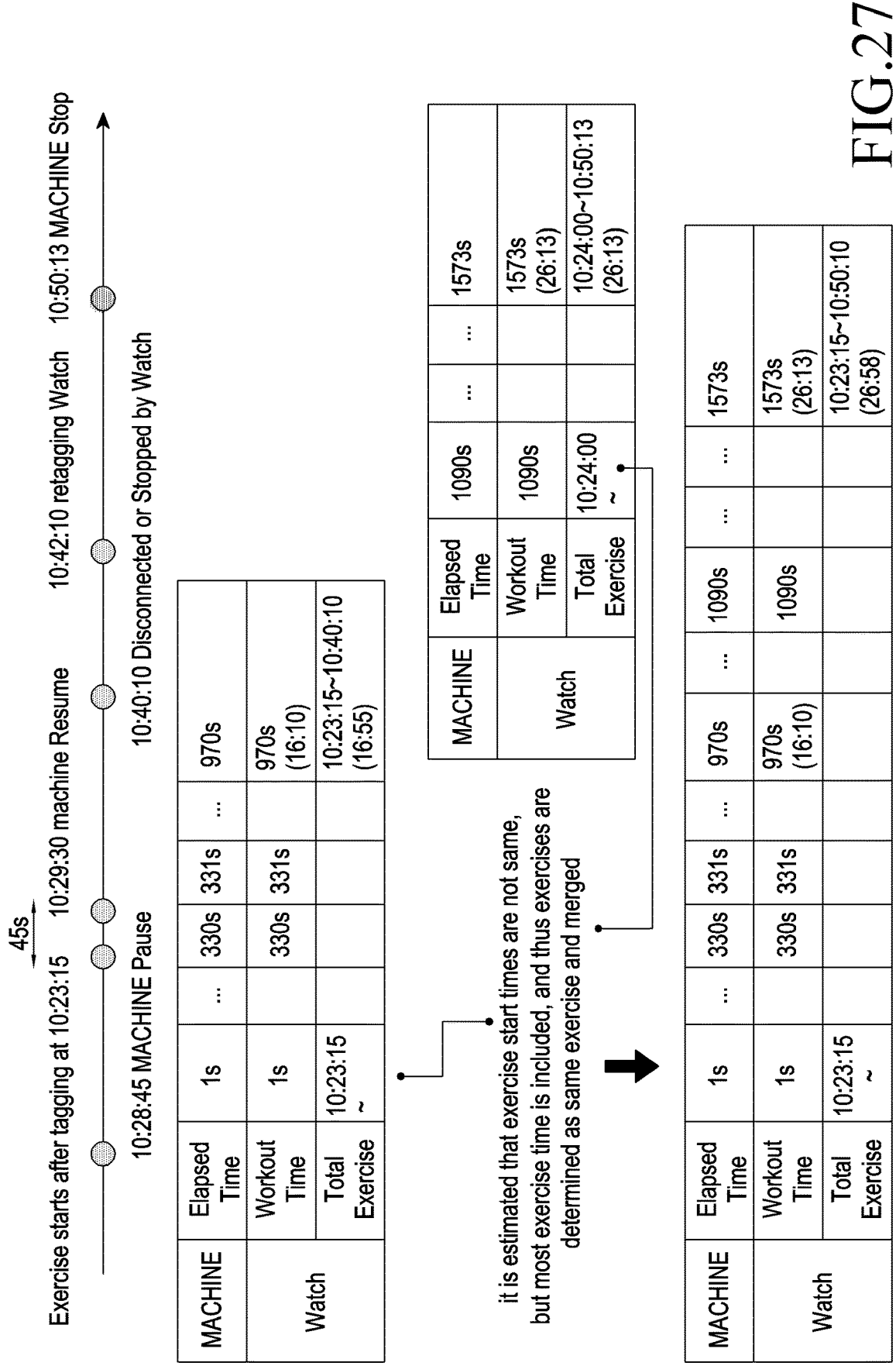
FIG. 27 illustrates an example of an operation for processing a pause section by an electronic device according to an embodiment of the disclosure.

FIG. 27 illustrates an example of an operation for processing a pause section by an electronic device according to an embodiment of the disclosure.

Referring to FIG. 27, since an exercise time of data which the electronic device 300 receives from the exercise machine 400 does not include a pause section, the electronic device 300 needs to consider the pause section when merging exercise sessions. As illustrated in FIG. 27, when an exercise session initially recognized by the electronic device 300 includes a pause time (for example, an interval of 45 seconds between 10:28:45 and 10:29:30), an inferable exercise start time may be different from a real exercise start time when a new exercise session to be merged starts (10:42:10). According to various embodiments, when an exercise start time of a new exercise session is inferred, if an exercise time overlaps an exercise time of the previous exercise for a predetermined time or longer, the exercise may be determined to be the same as the previous exercise and merged with the previous exercise.

Referring to FIG. 27, an exercise start time determined from an initially recognized exercise session is 10:23:15, and an exercise start time inferred for a new exercise session is 10:24:00. Although the initially recognized exercise session and the new exercise session are the same exercise session, it may be determined that the exercise start times are different from each other since a pause section is included in the initially recognized exercise session. According to various embodiments, as illustrated in FIG. 27, even though the exercise start times inferred from the two exercise sessions are different from each other, most exercise times of the two exercise sessions overlap each other, and thus the exercise sessions may be determined as the same one exercise session and merged. According to various embodiments, the electronic device 300 may merge the two exercise sessions and display exercise start time and end time including the actual pause section as 10:23:15~10:50:13.

Figure 28:
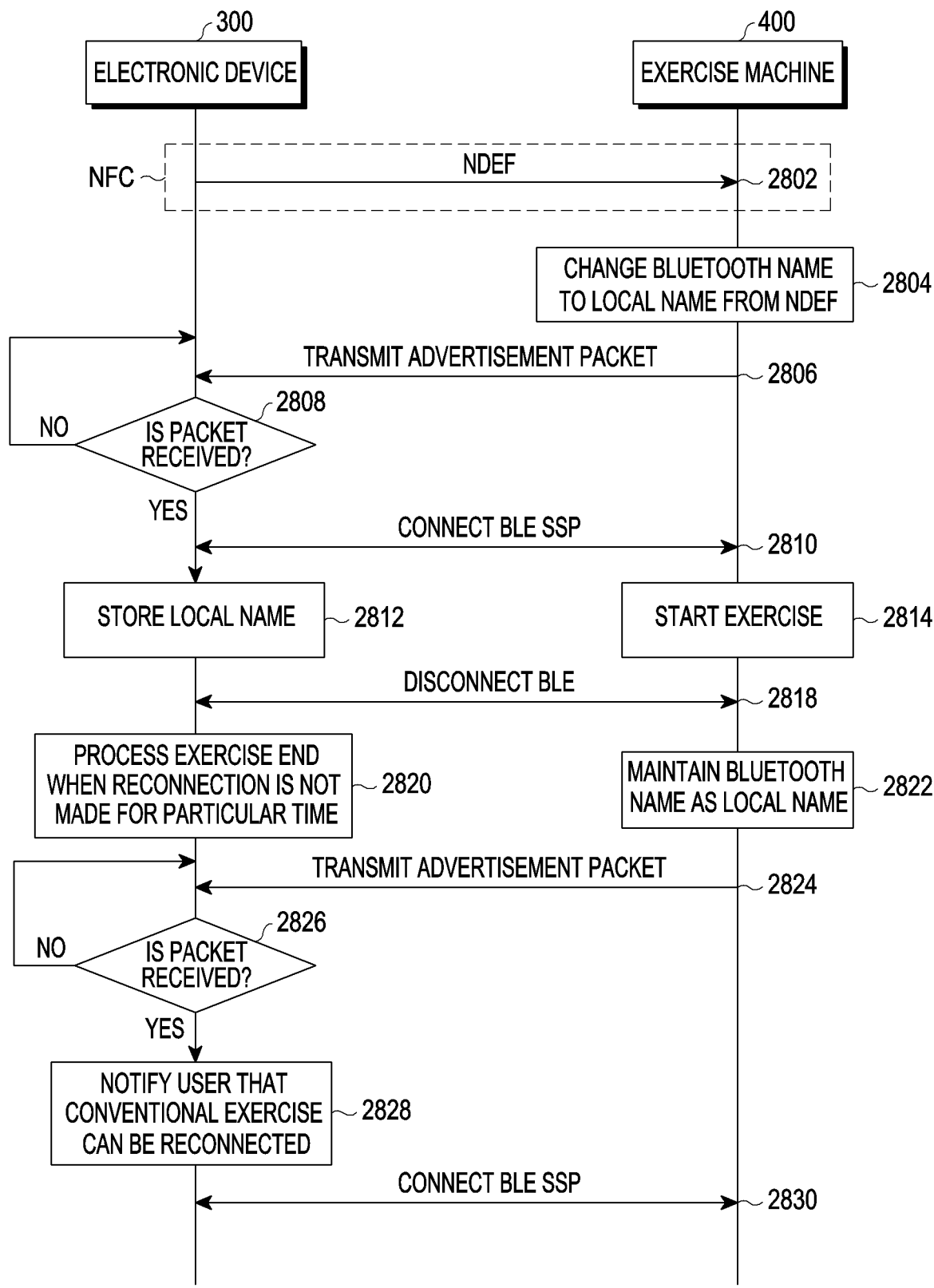
FIG. 28 is a flowchart illustrating a method of making a reconnection between an electronic device and an exercise machine according to an embodiment of the disclosure.

FIG. 28 is a flowchart illustrating a method of making a reconnection between an electronic device and an exercise machine according to an embodiment of the disclosure.

Referring to FIG. 28, when initially tagging on the exercise machine 400, the electronic device 300 (for example, the second electronic device 220) may generate a local name and transmit the same to the exercise machine 400. The exercise machine 400 should transmit an advertisement packet to the local name, and the electronic device 300 may scan for the exercise machine 400 to be connected on the basis of the generated local name and make a connection thereto.

According to various embodiments, the electronic device 300 may store a local name corresponding to the exercise machine 400 to be connected. Thereafter, when the connection with the exercise machine 400 is disconnected, if an advertisement signal of the same local name is scanned through a periodic scan, the electronic device 300 may inform the user that the reconnection with the exercise machine 400 of the related art is possible and make the reconnection. In FIG. 28 below, a detailed description of the operation that is the same as or similar to that of FIGS. 6A and 6B is omitted. For example, in the following description, operations 2802 to 2810 of FIG. 28 may be the same as or similar to operations 602 to 610 of FIGS. 6A and 6B.

In operation 2802, the electronic device 300 (for example, the first electronic device 210 or the second electronic device 220 of FIG. 2) may transmit NFC Data Exchange Format (NDEF) data by tagging an NFC module on the exercise machine 400. According to various embodiments, the electronic device 300 may operate as an NFC tag, and the exercise machine 400 may operate as an NFC reader.

In operation 2804, the exercise machine 400 may change a Bluetooth name to a local name on the basis of the received NDEF data. According to various embodiments, the local name may be used to identify the electronic device 300 by the exercise machine 400 when the electronic device 300 is connected to the exercise machine 400 and exchange information therewith.

In operation 2806, the exercise machine 400 may transmit an advertisement packet to the electronic device 300. According to various embodiments, the exercise machine 400 may transmit the advertisement packet to the electronic device 300 in a broadcasting manner.

When the electronic device 300 receives the advertisement packet in operation 2808, the electronic device 300 may make a BLE Secure Simple Pairing (SSP) connection with the exercise machine 400 on the basis of information included in the received advertisement packet (for example, at least one piece of information included in the NDEF data) in operation 2810.

In operation 2812, the electronic device 300 may store a local name used for the connection with the exercise machine 400 in the memory.

According to various embodiments, when the exercise starts in operation 2814 and the BLE connection between the electronic device 300 and the exercise machine 400 is stopped and communication is disconnected in operation 2818, the electronic device 300 may attempt the BLE reconnection with the exercise machine 400 for a predetermined time in operation 2820 and when the reconnection fails for the predetermined time, ends the corresponding exercise.

According to various embodiments, in operation 2822, even though the BLE connection with the electronic device 300 is disconnected, the exercise machine 400 may maintain a name of the BLE connection with the electronic device 300 as the local name. In an initial connection, the exercise machine 400 may attempt the connection with the electronic device 300 by transmitting an advertisement packet in operation 2824 like in operation 2806. According to various embodiments, the advertisement packet transmitted by the exercise machine 400 may include the local name. When the electronic device 300 receiving the advertisement packet identifies the local name included in the advertisement packet in operation 2826, the electronic device 300 may inform the user that reconnection of the exercise of the related art is possible through the screen in operation 2828.

When the user accepts the reconnection of the exercise of the related art on the basis of the informing result, the electronic device 300 may make a BLE SSP connection with the exercise machine 400 in operation 2830.

Figure 29:
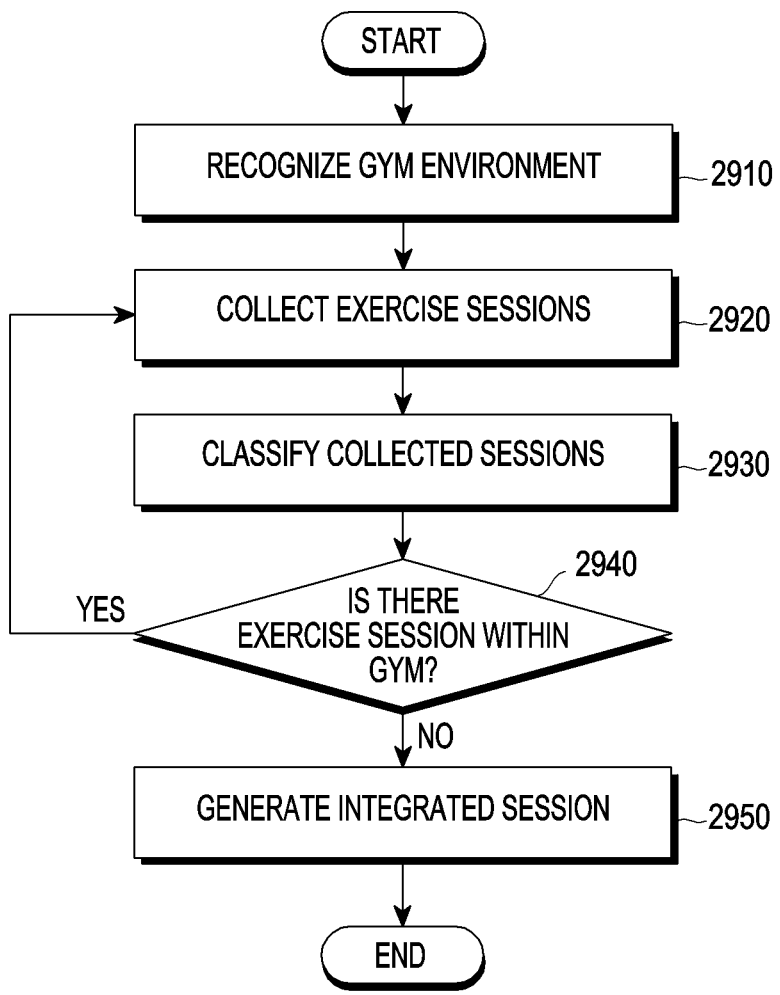
FIG. 29 is a flowchart illustrating an operation for integrating exercise sessions by an electronic device according to an embodiment of the disclosure.

FIG. 29 is a flowchart illustrating an operation for integrating exercise sessions by an electronic device according to an embodiment of the disclosure.

FIG. 30 illustrates an individual exercise result screen of an electronic device according to an embodiment of the disclosure.

Figure 31:
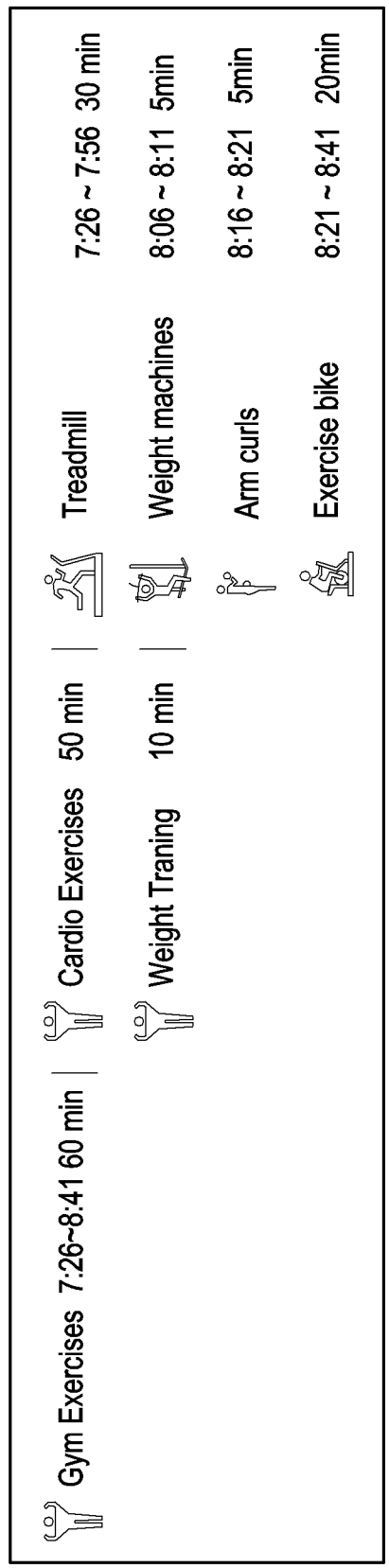
FIG. 31 illustrates a result screen of exercises indicating integrated exercise sessions in an electronic device according to an embodiment of the disclosure.

FIG. 31 illustrates an exercise result screen in which exercise sessions are integrated by an electronic device according to an embodiment of the disclosure.

Referring to FIG. 29, according to various embodiments, the exercise in the GYM may be conducted using various machine rather than a machine. When storage of the exercise record is made in units of exercise machine and thus considered individually for each exercise machine despite the exercises being in the same GYM, it may be difficult to identify connectivity between exercises. According to various embodiments, when the user exercises within the same GYM, the electronic device 300 may integrate and display exercises within the GYM on the basis of context for the corresponding exercise result, thereby providing a better UI to the user.

In operation 2910, the electronic device 300 may recognize a GYM environment. Recognition of the GYM environment may be determined through entry into a specific GYM building or through an attendance check of the corresponding GYM. According to various embodiments, the electronic device 300 may determine whether the exercise is conducted within the GYM on the basis of location information. According to various embodiments, the electronic device 300 may determine whether there are many exercise machines 400 around the electronic device 300 to identify whether the electronic device 300 is located inside the GYM. According to various embodiments, when there are many signals broadcasted from the exercise machine 400 (for example, the number of signals is larger than or equal to a predetermined number), the electronic device 300 may determine that the electronic device 300 is inside the GYM.

In operation 2920, the electronic device 300 may be tagged on each exercise machine 400 for an exercise and collect exercise information for each exercise session during the exercise. In operation 2930, the electronic device 300 may classify the collected exercise sessions according to an exercise type. According to various embodiments, when the electronic device 300 recognizes an environment inside the GYM, the electronic device 300 may collect exercise sessions generated in the environment and classify the collected exercises according to a predetermined category. For example, the exercises may be classified into aerobic exercise and anaerobic exercise or classified into exercise of the upper part of the body and exercise of the lower part of the body according to the exercise part.

The electronic device 300 may determine whether the user stays in the GYM or leaves the GYM in operation 2940. When the user stays in the GYM, the electronic device 300 may continuously collect exercise information for each exercise session. When the user leaves the GYM, the electronic device 300 may generate an integrated exercise session and display the result on the display in operation 2950. For example, when the electronic device 300 recognizes that the user is not in the GYM environment, the electronic device 300 may generate an exercise session that may synthetically show the exercises within the GYM and provide the result of each exercise session.

Referring to FIG. 30, when the user exercises on a treadmill for 30 minutes, takes a rest for 10 minutes, exercises with a weight machine for 5 minutes, takes a rest for 5 minutes, exercises with arm curls for 5 minutes, and rides an exercise bike for 20 minutes, four different exercises may be shown.

According to various embodiments, when the algorithm of FIG. 29 is applied, it is possible to provide a better user experience (UX) to the user by displaying information indicating that the user has stayed in a specific GYM for 75 minutes and has done exercises corresponding to four exercise sessions as illustrated in FIG. 31. Referring to FIG. 31, exercise sessions collected within the GYM may be classified according to predetermined categories. For example, information indicating that the user does aerobic exercise (cardio exercise) for 50 minutes and weight training for 10 minutes may be displayed on the display.

Figure 32A:
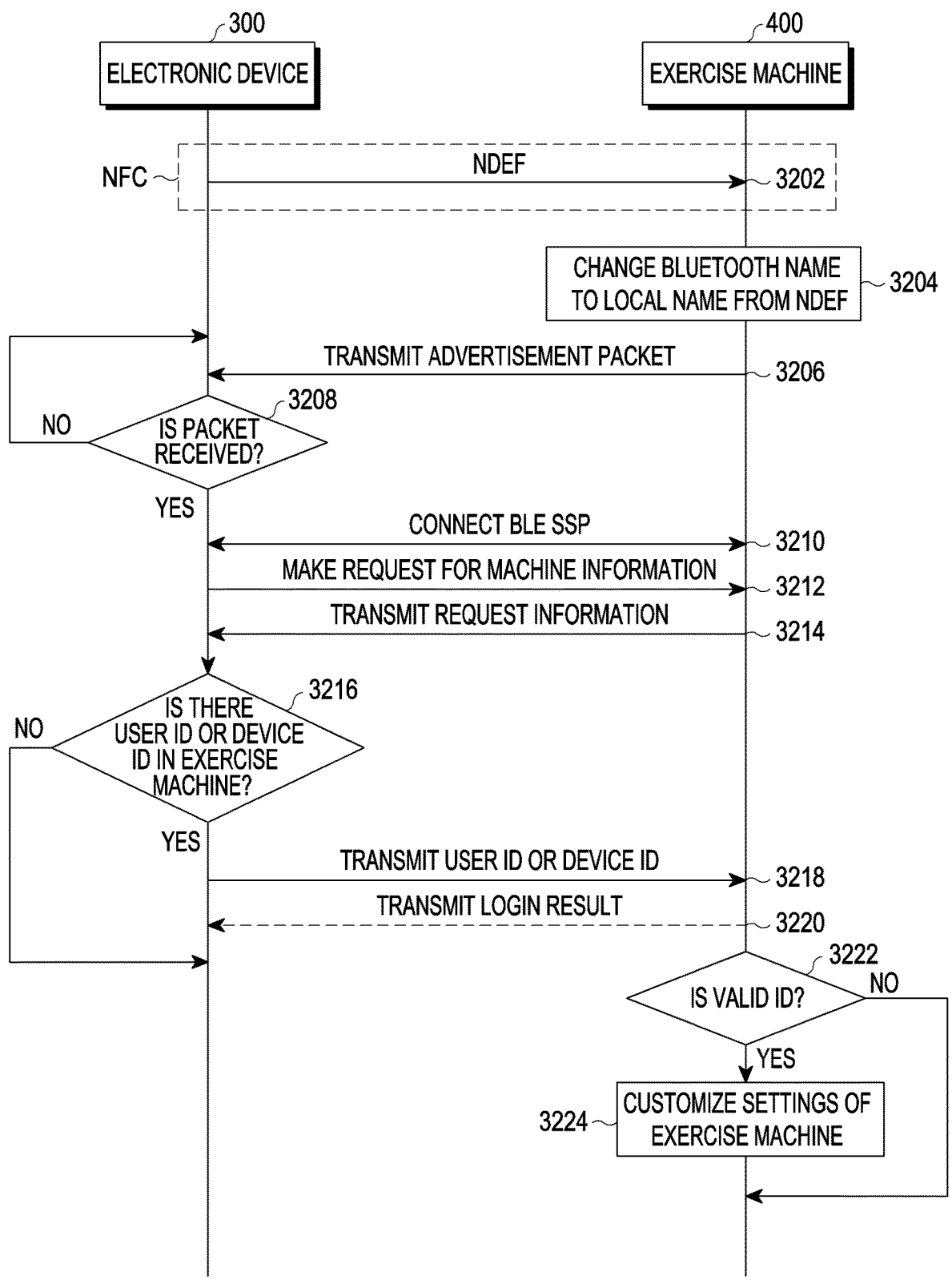
FIG. 32A is a flowchart illustrating a method of making a connection between an electronic device and an exercise machine and exchanging data according to an embodiment of the disclosure.

FIG. 32A is a flowchart illustrating a method of making a connection between the electronic device and the exercise machine and exchanging data according to an embodiment of the disclosure.

Figure 32B:
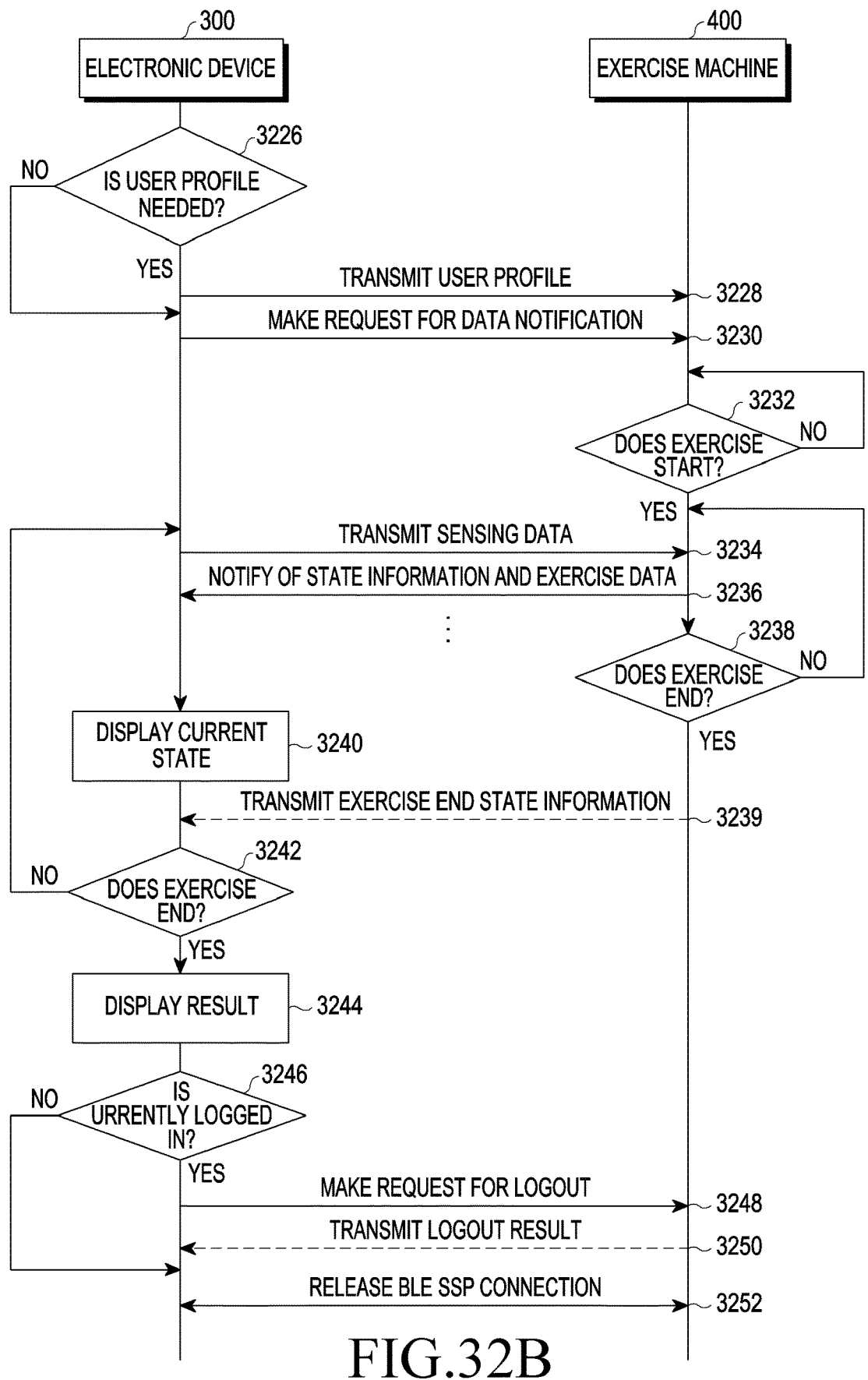
FIG. 32B is a flowchart illustrating a method of making a connection between an electronic device and an exercise machine and exchanging data according to an embodiment of the disclosure.

FIG. 32B is a flowchart illustrating a method of making a connection between the electronic device and the exercise machine and exchanging data according to an embodiment of the disclosure.

According to various embodiments, an operation in which the electronic device 300 makes a request for logging out of the exercise machine 400 after an exercise ends in the state in which the electronic device 300 is connected to the exercise machine 400 through NFC/BLE is described with reference to FIGS. 32A and 32B.

Referring to FIG. 32A, in operation 3202, the electronic device 300 (for example, the first electronic device 210 or the second electronic device 220 of FIG. 2) may transmit NFC Data Exchange Format (NDEF) data by tagging an NFC module on the exercise machine 400. According to various embodiments, the electronic device 300 may operate as an NFC tag, and the exercise machine 400 may operate as an NFC reader.

According to various embodiments, the NDEF data may include at least one of a BLE address, a Low Energy (LE) role, a local name, a confirmation value, or a random value.

In operation 3204, the exercise machine 400 may change a Bluetooth name to a local name on the basis of the received NDEF data. According to various embodiments, the local name may be used to identify the electronic device 300 by the exercise machine 400 when the electronic device 300 is connected to the exercise machine 400 and exchange information therewith.

In operation 3206, the exercise machine 400 may transmit an advertisement packet to the electronic device 300. According to various embodiments, the exercise machine 400 may transmit the advertisement packet to the electronic device 300 in a broadcasting manner According to various embodiments, the advertisement packet may include at least one piece of data received from the electronic device 300 through the NDEF data, for example, at least one of a Fitness Machine Service (FTMS) Universally Unique Identifier (UUID), a BLE address, an LE role, a local name, a confirmation value, or a random value. According to various embodiments, the advertisement packet may include information on an exercise machine type corresponding to the exercise machine 400.

When the electronic device 300 receives the advertisement packet in operation 3208, the electronic device 300 may make a BLE Secure Simple Pairing (SSP) connection with the exercise machine 400 on the basis of information included in the received advertisement packet (for example, at least one piece of information included in the NDEF data) in operation 3210. According to various embodiments, the electronic device 300 may make a request for machine information to the exercise machine 400 on the basis of the BLE protocol in operation 3212, and the exercise machine 400 may transmit the machine information to the electronic device 300 in response to the request for the machine information from the electronic device 300 in operation 3214. According to various embodiments, the machine information transmitted by the exercise machine 400 may include at least one of manufacturer information, a model name of the exercise machine, and information on a type of the exercise machine (fitness machine type) information. According to various embodiments, the machine information transmitted by the exercise machine 400 may further include information on whether an ID is needed or a user profile is needed.

In operation 3216, the electronic device 300 may identify whether there is user identification information (user identifier (ID)) or a device ID (machine ID) for the exercise machine 400 on the basis of information on the exercise machine received from the exercise machine 400.

When there is the user ID or the device ID corresponding to the exercise machine 400 in the electronic device 300 on the basis of the identification result, the electronic device 300 may transmit the user ID or the device ID to the exercise machine 400 in operation 3218.

According to various embodiments, the exercise machine 400 may receive the user ID or the device ID from the electronic device 300 and log in the electronic device 300 with the received user ID or device ID. In operation 3220, the exercise machine 400 may transmit the login result to the electronic device 300 after performing the login. According to various embodiments, a login key (for example, a machine ID) corresponding to the user ID may be transmitted instead of the user ID in operation 3218. For example, when the electronic device 300 (for example, the first electronic device 210 or the second electronic device 220) is logged in with the corresponding user ID, the electronic device 300 may receive a machine key of the corresponding user ID from a server (for example, the account management server 250). The electronic device 300 may transmit the login key received from the server to the exercise machine 400. The exercise machine 400 may process the login of the user onto the electronic device 300 by identifying the login key received from the electronic device 300 through the server. According to various embodiments, the server may issue the login key in the form of a hash code and identify the user by means of the login key.

The exercise machine 400 may authenticate the user ID or the device ID received from the electronic device 300 and when the user ID or the device ID is a valid ID on the basis of the authentication result in operation 3222, settings for the exercise machine 400 may be customized to correspond to the user ID or the device ID in operation 3224.

Referring to FIG. 32B, according to various embodiments, the electronic device 300 may identify information on whether user profile information is needed within machine information received from the exercise machine 400 and when it is determined that the exercise machine 400 needs the user profile information in operation 3226, the electronic device 300 may transmit the user profile to the exercise machine 4000 in operation 3228.

In operation 3230, the electronic device 300 may make a request for data notification to the exercise machine 400.

In operation 3232, when the exercise starts, the electronic device 300 may acquire sensing data in real time by driving a configured sensor corresponding to the exercise machine 400. In operation 3234, the electronic device 300 may transmit the sensing data acquired in real time to the exercise machine 400. In operation 3236, the exercise machine 400 may notify the electronic device 300 of state information and exercise data in response to the request for data notification received from the electronic device 300. According to various embodiments, in operation 3240, the electronic device 300 may display information related to the current state on the display on the basis of the sensing data acquired by the electronic device 300 or the state information or the exercise data received from the exercise machine 400.

When the exercise ends in operation 3238, the exercise machine 400 may transmit state information indicating the end of the exercise to the electronic device 300 in operation 3239.

The electronic device 300 may receive the state information indicating the end of the exercise from the exercise machine 400 and determine the end of the exercise in operation 3242. According to various embodiments, the electronic device 300 may display the exercise result on the display in accordance with the determination of the end of the exercise in operation 3244.

According to various embodiments, even though the exercise using the exercise machine 400 ends and the electronic device 300 identifies the end of the exercise, the current login state may be continuously maintained. According to various embodiments, in the state in which the electronic device 300 is logged in, another user may attempt to login but cannot complete the login. When the user ends the exercise, the electronic device 300 may be logged out and then disconnected from the exercise machine 400.

According to various embodiments, when the electronic device 300 determines that a login state is currently maintained even though the exercise ends in operation 3246, the electronic device 300 may make a request for logging out to the exercise machine 400 in operation 3248. In operation 3250, the exercise machine 400 may transmit a logout result to the electronic device 300.

As the exercise ends and the logout between the electronic device 300 and the exercise machine 400 is processed, the electronic device 300 may release the BLE SSP connection with the exercise machine 400 in operation 3252.

Figure 33:
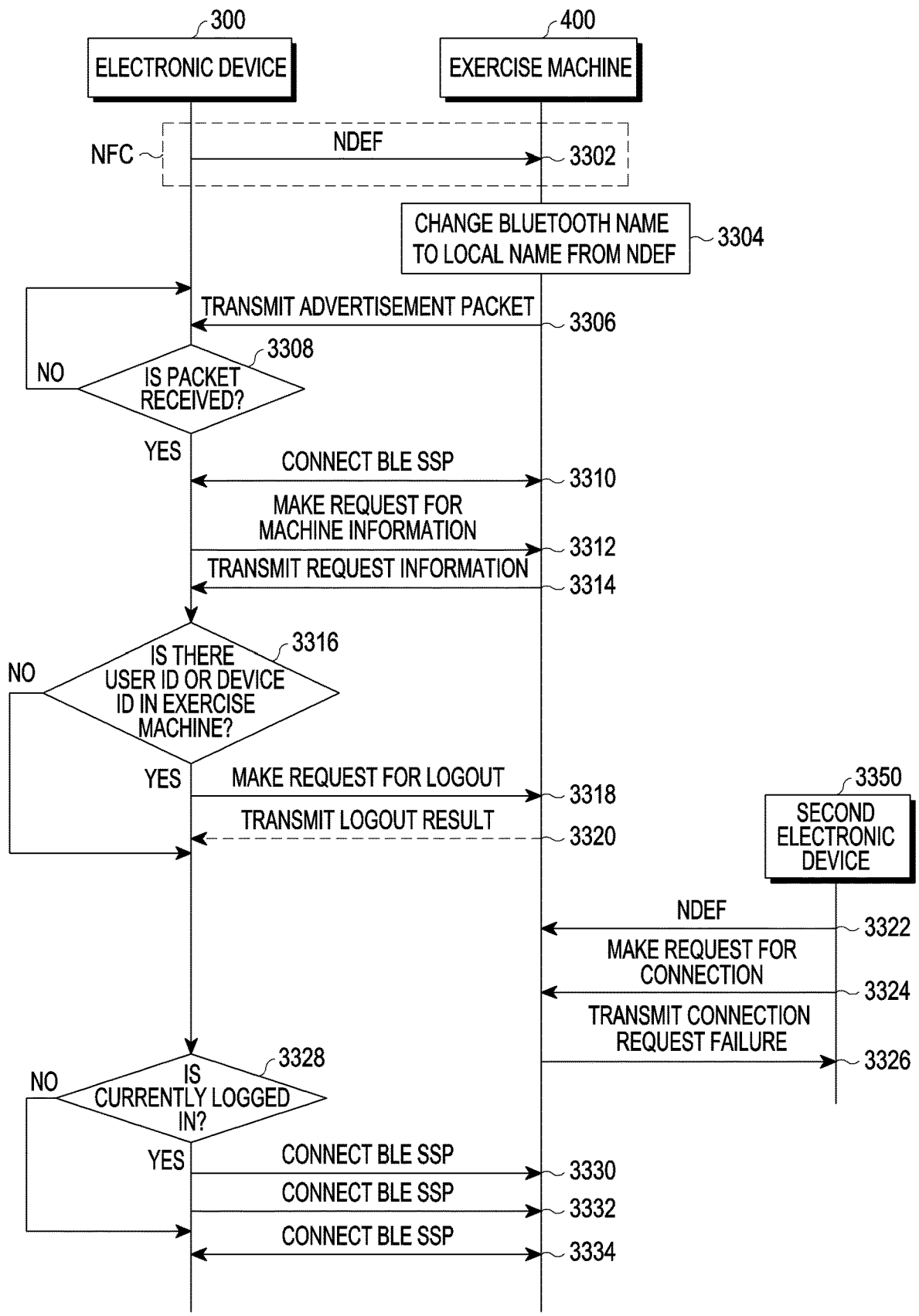
FIG. 33 is a flowchart illustrating a method of the connection between an electronic device and an exercise machine according to an embodiment of the disclosure.

FIG. 33 is a flowchart illustrating a method of the connection between the electronic device and the exercise machine according to an embodiment of the disclosure.

Referring to FIG. 33, an operation method when the login with a second user ID of a second electronic device (for example, a second wearable electronic device) is attempted in the state in which the exercise machine is currently connected with a first user ID of an electronic device (for example, a first wearable electronic device) is described.

In operation 3302, the electronic device 300 (for example, the second electronic device 220 of FIG. 2) may transmit NFC Data Exchange Format (NDEF) data by tagging an NFC module on the exercise machine 400. According to various embodiments, the electronic device 300 may operate as an NFC tag, and the exercise machine 400 may operate as an NFC reader.

According to various embodiments, the NDEF data may include at least one of a BLE address, a Low Energy (LE) role, a local name, a confirmation value, or a random value.

In operation 3304, the exercise machine 400 may change a Bluetooth name to a local name on the basis of the received NDEF data. According to various embodiments, the local name may be used to identify the electronic device 300 by the exercise machine 400 when the electronic device 300 is connected to the exercise machine 400 and exchange information therewith.

In operation 3306, the exercise machine 400 may transmit an advertisement packet to the electronic device 300. According to various embodiments, the exercise machine 400 may transmit the advertisement packet to the electronic device 300 in a broadcasting manner According to various embodiments, the advertisement packet may include at least one piece of data received from the electronic device 300 through the NDEF data, for example, at least one of a Fitness Machine Service (FTMS) Universally Unique Identifier (UUID), a BLE address, an LE role, a local name, a confirmation value, or a random value. According to various embodiments, the advertisement packet may include information on an exercise machine type corresponding to the exercise machine 400.

When the electronic device 300 receives the advertisement packet in operation 3308, the electronic device 300 may make a BLE Secure Simple Pairing (SSP) connection with the exercise machine 400 on the basis of information included in the received advertisement packet (for example, at least one piece of information included in the NDEF data) in operation 3310. According to various embodiments, the electronic device 300 may make a request for machine information to the exercise machine 400 on the basis of the BLE protocol in operation 3312, and the exercise machine 400 may transmit the machine information to the electronic device 300 in response to the request for the machine information from the electronic device 300 in operation 3314. According to various embodiments, the machine information transmitted by the exercise machine 400 may include at least one of manufacturer information, a model name of the exercise machine, and information on a type of the exercise machine (fitness machine type) information. According to various embodiments, the machine information transmitted by the exercise machine 400 may further include information on whether an ID is needed or a user profile is needed.

In operation 3316, the electronic device 300 may identify whether there is user identification information (user identifier (ID)) or a device ID (machine ID) for the exercise machine 400 on the basis of information on the exercise machine received from the exercise machine 400.

When there is the user ID or the device ID corresponding to the exercise machine 400 in the electronic device 300 on the basis of the identification result, the electronic device 300 may transmit the user ID or the device ID to the exercise machine 400 in operation 3318.

According to various embodiments, the exercise machine 400 may receive the user ID or the device ID from the electronic device 300 and log in the electronic device 300 with the received user ID or device ID. In operation 3320, the exercise machine 400 may transmit the login result to the electronic device 300 after performing the login.

According to various embodiments, in the state in which the electronic device 300 is logged in, another user may attempt to login but cannot complete the login. When the user ends the exercise, the electronic device 300 may be logged out and then disconnected from the exercise machine 400. As illustrated in FIG. 33, in the case in which a second electronic device 3350 (for example, a wearable electronic device) attempts a connection with the same exercise machine 400 in the state in which a login session of the electronic device 300 is maintained, if another user attempts a connection, the connection may fail while the connection or login of the electronic device 300 is maintained because a user ID or a device ID is different.

According to various embodiments, in operation 3322, the second electronic device 3350 may transmit NFC Data Exchange Format (NDEF) data by tagging an NFC module on the exercise machine 400. According to various embodiments, the second electronic device 3350 may operate as an NFC tag, and the exercise machine 400 may operate as an NFC reader.

According to various embodiments, the second electronic device 3350 may make a request for access to the exercise machine 400 in operation 3324, and the exercise machine 400 may reject the request for access from the second electronic device 3350 since the login of the electronic device 300 is maintained, and transmit an access request failure message to the second electronic device 3350 in operation 3326. According to various embodiments, the electronic device 300 and the exercise machine 400 may exchange data after one-to-one connection.

According to various embodiments, when it is determined that the current login state is maintained even though the exercise ends in operation 3328, the electronic device 300 may make a request for logging out to the exercise machine 400 in operation 3330. In operation 3332, the exercise machine 400 may transmit a logout result to the electronic device 300.

As the exercise ends and the logout between the electronic device 300 and the exercise machine 400 is processed, the electronic device 300 may release the BLE SSP connection with the exercise machine 400 in operation 3334.

According to various embodiments, when the electronic device 300 is logged out, the second electronic device 3350 may perform login by tagging on the exercise machine 400.

Figure 34:
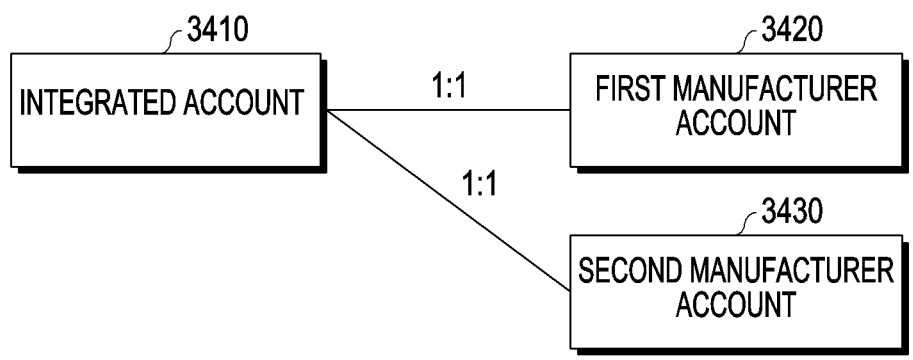
FIG. 34 illustrates the mapping relation between an integrated account and each manufacturer account according to an embodiment of the disclosure.

FIG. 34 illustrates the mapping relation between an integrated account and each manufacturer account according to an embodiment of the disclosure.

Referring to FIG. 34, the relation between an integrated account 3410 and each fitness manufacturer account is illustrated. For example, the integrated account 3410 has one-to-one relation with each manufacturer account (for example, a first manufacturer account 3420 or a second manufacturer account 3430).

Figure 35:
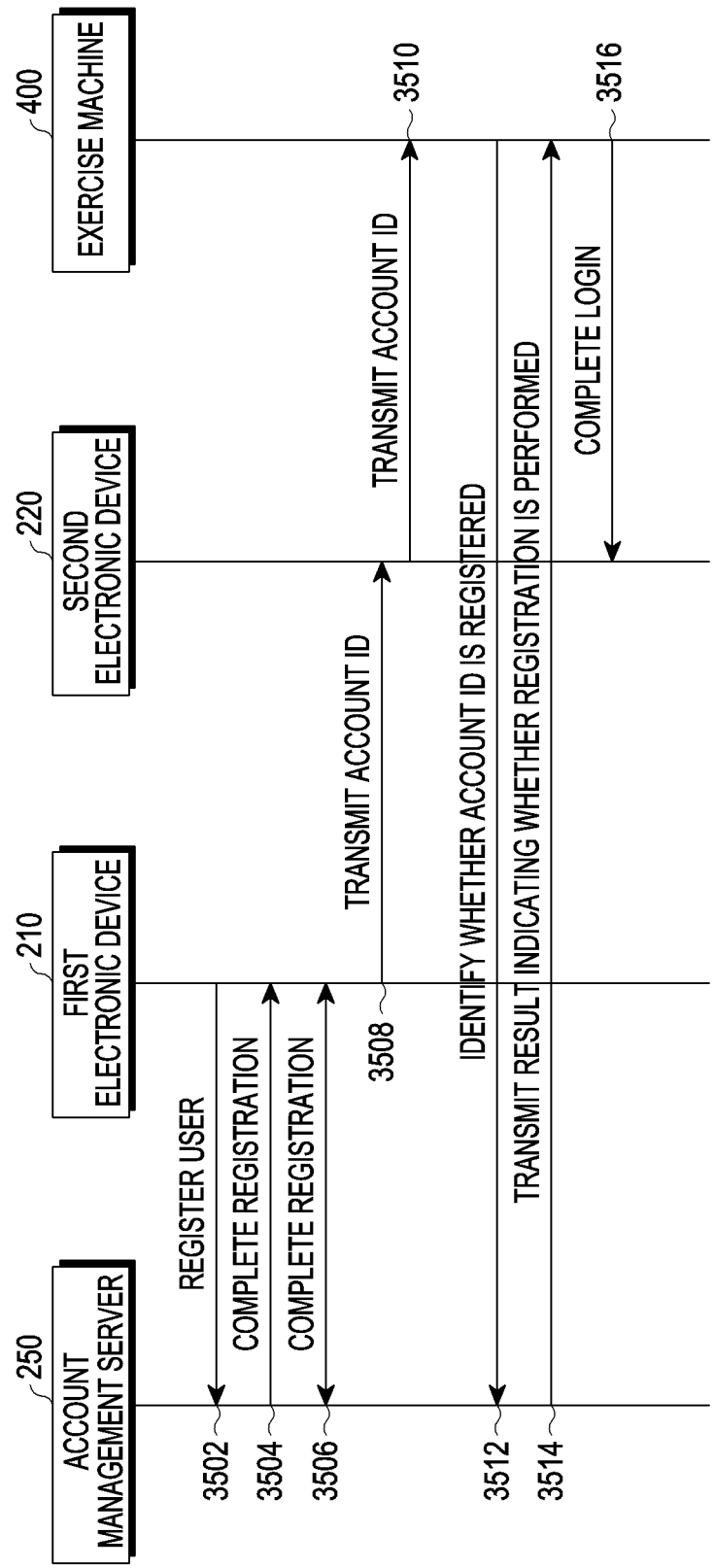
FIG. 35 is a flowchart illustrating a login operation through an account management server by an electronic device according to an embodiment of the disclosure.

FIG. 35 is a flowchart illustrating a login operation through an account management server by an electronic device according to an embodiment of the disclosure.

Referring to FIG. 35, in operation 3502, the first electronic device 210 may register a user in the account management server 250. According to various embodiments, the account management server 250 may be a server of each fitness manufacturer or may be an integrated account server which can be used by anyone regardless of a manufacturer.

When the user registration is completed in operation 3504, the first electronic device 210 may perform login on the basis of registered information in operation 3506 and transmit a login result account ID to the second electronic device 220 in operation 3508. According to various embodiments, in operation 3508, a login key (for example, a device ID (machine ID)) corresponding to the account ID may be transmitted instead of the account ID. For example, when the electronic device 300 (for example, the first electronic device 210 or the second electronic device 220) is logged in with the corresponding user ID, the electronic device 300 may receive a machine key of the corresponding user ID from a server (for example, the account management server 250). The electronic device 300 may transmit the login key received from the server to the exercise machine 400. The exercise machine 400 may process the login of the user onto the electronic device 300 by identifying the login key received from the electronic device 300 through the server. According to various embodiments, the server may issue the login key in the form of a hash code and identify the user by means of the login key.

According to various embodiments, in operation 3510, the second electronic device 220 may transmit the account ID or the login key to the exercise machine 400 to log in to the exercise machine 400.

According to various embodiments, the exercise machine 400 may identify whether the corresponding account ID is registered in the account management server 250 in operation 3512, and the account management server 250 may transmit the registration result to the exercise machine 400 in response to the request for identification in operation 3514. When the registration result is registered, the second electronic device 220 may log in to the exercise machine 400 in operation 3516.

According to various embodiments, the account ID may be an identifier for identifying the user. According to various embodiments, the account ID may be a token, and the token may be issued through an integrated account server that integratively manages respective accounts of the account management server 250.

Figure 36:
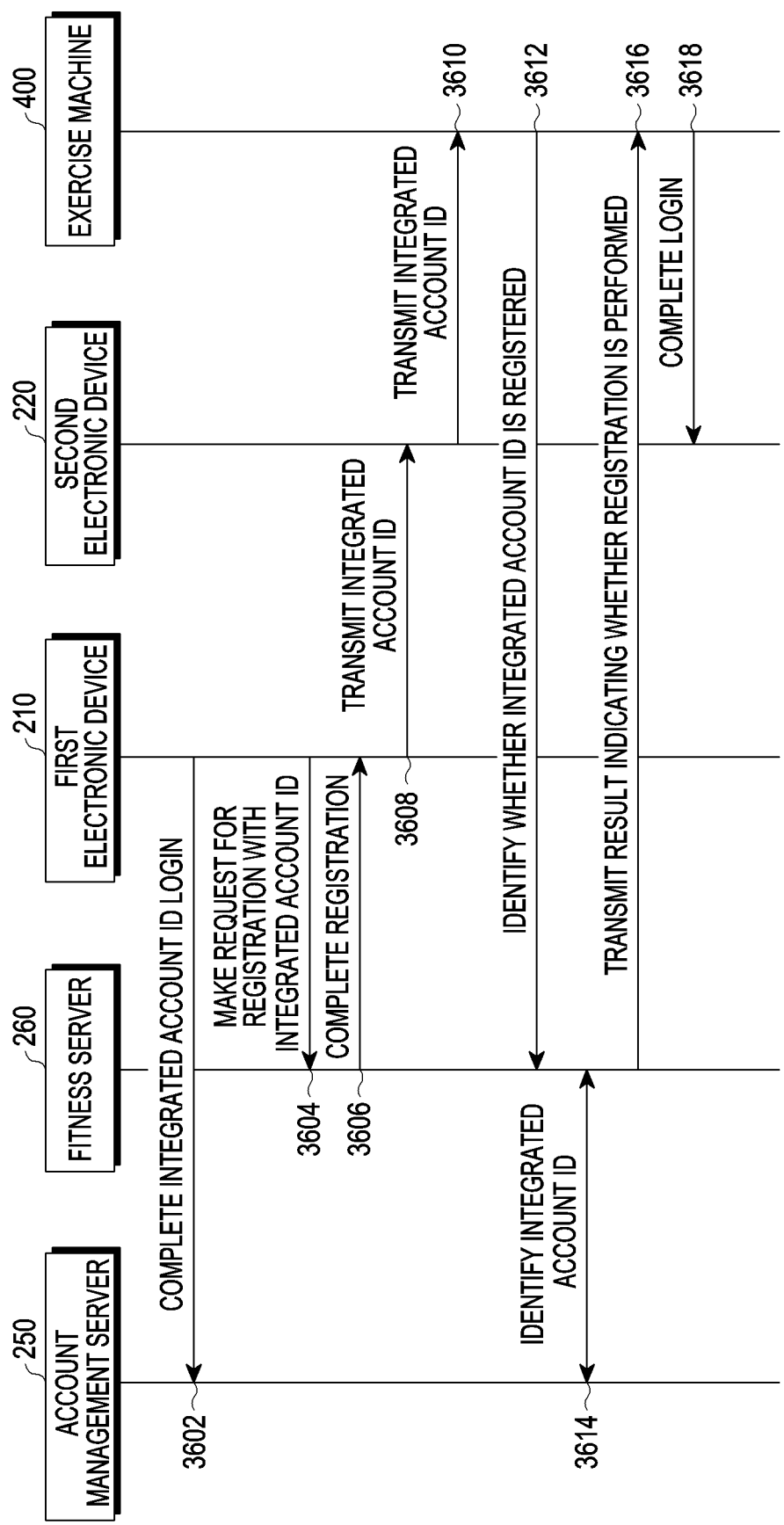
FIG. 36 is a flowchart illustrating a login operation through an account management server by an electronic device according to an embodiment of the disclosure.

FIG. 36 is a flowchart illustrating a login operation through an account management server by an electronic device according to an embodiment of the disclosure.

Referring to FIG. 36, in operation 3602, the first electronic device 210 may log in the account management server 250 that integratively manages accounts with an integrated account ID.

According to various embodiments, in operation 3604, the first electronic device 210 may make a request for registering the integrated account ID in the account of the fitness manufacturer as an integrated account to the fitness server 260 corresponding to each fitness manufacturer. The integrated account may be linked to the fitness manufacturer account according to registration of the integrated account.

According to various embodiments, when the login process is performed and the account link is successful, registration is completed and the fitness server 260 may inform the first electronic device 210 of the registration completion result in operation 3606.

The first electronic device 210 may transmit the integrated account ID to the second electronic device 220 in operation 3608, and the second electronic device 220 may transmit the integrated account ID to the exercise machine 400 in operation 3610. According to various embodiments, in operation 3608, a login key (for example, a device ID (machine ID)) corresponding to the integrated account ID may be transmitted instead of the integrated account ID. For example, when the electronic device 300 (for example, the first electronic device 210 or the second electronic device 220) performs login with the corresponding integrated account ID, the electronic device 300 may receive the login key (machine ID) for the corresponding user ID from a server (for example, the account management server 250 or the fitness server 260). The electronic device 300 may transmit the login key received from the server to the exercise machine 400. The exercise machine 400 may process the login of the user onto the electronic device 300 by identifying the login key received from the electronic device 300 through the server. According to various embodiments, the server may issue the login key in the form of a hash code and identify the user by means of the login key.

In order to identify whether the integrated account ID received from the second electronic device 220 is registered, the exercise machine 400 may make a request for identifying whether the integrated account ID is registered to the fitness server 260 in operation 3612. In operation 3614, the fitness server 260 may identify whether the integrated account ID is registered through the account management server 250 according to the request for identifying whether the integrated account ID is registered from the exercise machine 400.

According to various embodiments, in operation 3616, the fitness server 260 may transmit the result of identifying whether the integrated account ID is registered to the exercise machine 400. In operation 3618, the exercise machine 400 may identify from the fitness server 260 that the integrated account ID received from the second electronic device 220 is normally registered and process login completion.

Figure 37:
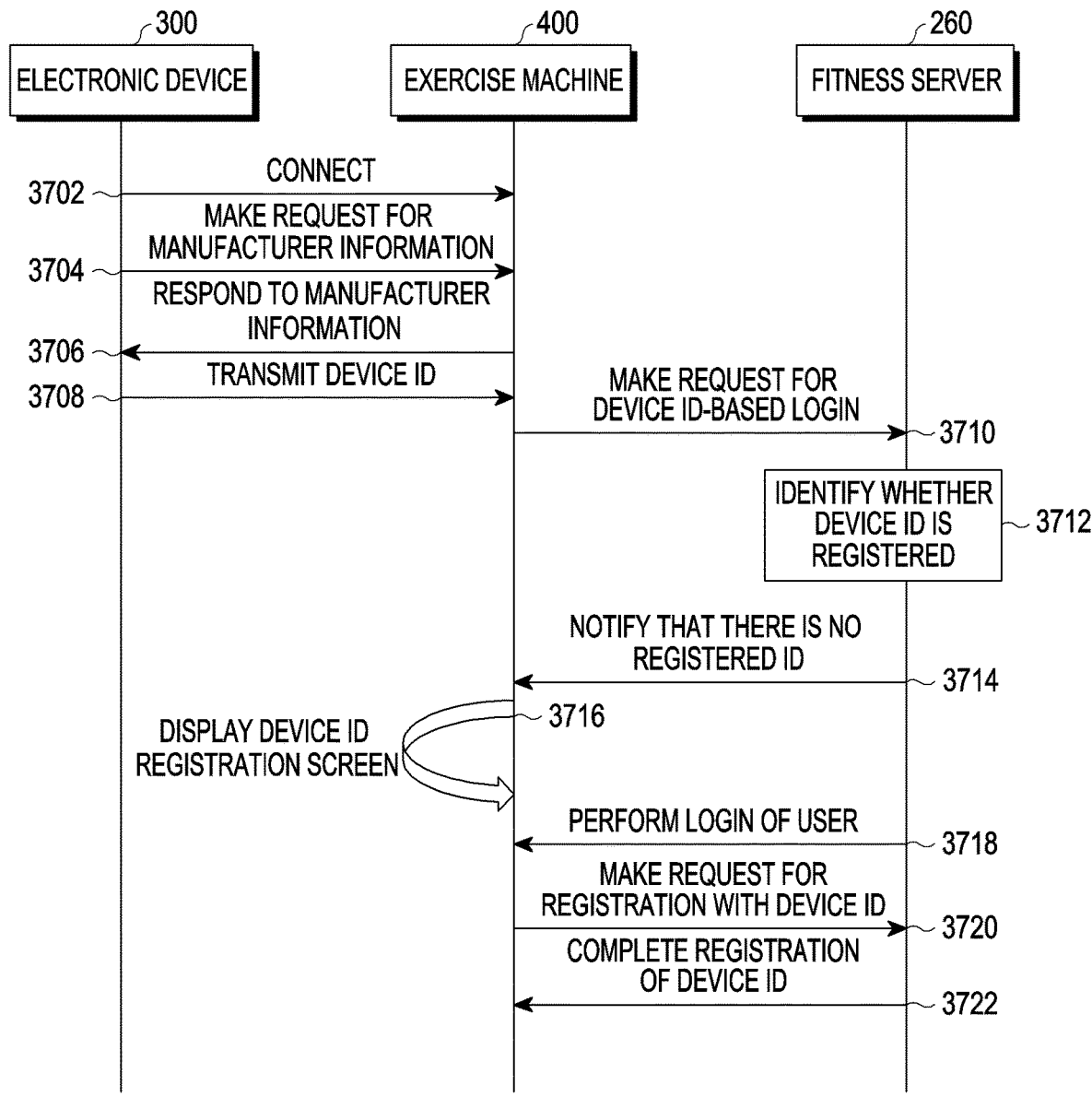
FIG. 37 is a flowchart illustrating a device identification (ID) registration operation of an electronic device according to an embodiment of the disclosure.

FIG. 37 is a flowchart illustrating a device ID registration operation of an electronic device according to an embodiment of the disclosure.

Referring to FIG. 37, the electronic device 300 (for example, the first electronic device 210 or the second electronic device 220) may log in to the exercise machine 400 on the basis of a unique device ID generated by the electronic device 300.

When the electronic device 300 is connected to the exercise machine 400 in operation 3702, the electronic device 300 may make a request for manufacturer information of the exercise machine 400 to the exercise machine 400 in operation 3704.

In operation 3706, the electronic device 300 may receive manufacturer information from the exercise machine 400, and the electronic device 300 may generate the device ID on the basis of the manufacturer information received from the exercise machine 400 and unique identification information of the electronic device 300. According to various embodiments, the device ID may be generated for each manufacturer or generated regardless of a manufacturer. In operation 3708, the electronic device 300 may transmit the generated device ID to the exercise machine 400.

In operation 3710, the exercise machine 400 may make a request for performing login with the device ID received from the electronic device 300 to the fitness server 260.

In operation 3712, the fitness server 260 may identify whether the device ID received from the exercise machine 400 is registered.

When there is no registered ID on the basis of the identification result, the fitness server 260 may inform the exercise machine 400 that there is no registered ID in operation 1714. For example, when the device ID corresponds to information that is not stored in the fitness server 260, a device ID registration screen may be displayed through a console of the exercise machine located in the GYM to inform the user of the fact in operation 3716 and the user may be informed that the login through the electronic device 300 is possible through registration of the corresponding electronic device 300 in a user account.

The user may perform user login onto the fitness server 260 with his/her own account through the exercise machine 400 in operation 3718 and make a request for registering a device ID of the electronic device 300 in operation 3720. In operation 3722, the fitness server 260 may register the device ID according to the request for registering the device ID and inform the exercise machine 400 of the registration completion. Thereafter, the user may perform user login on the fitness server 260 through the device ID of the electronic device 300.

Figure 38:
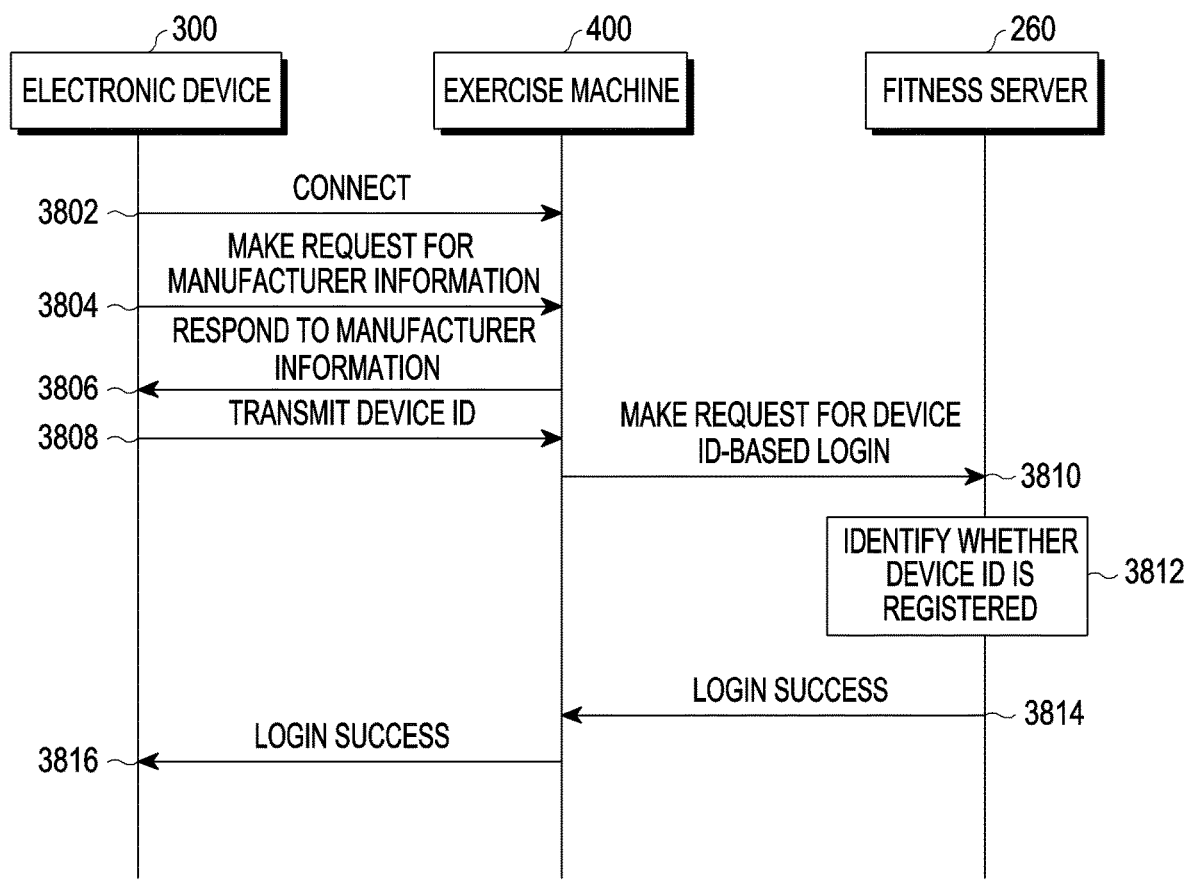
FIG. 38 is a flowchart illustrating an ID-based login operation of an electronic device according to embodiment of the disclosure.

FIG. 38 is a flowchart illustrating an ID-based login operation of an electronic device according to an embodiment of the disclosure.

Referring to FIG. 38, the electronic device 300 (for example, the first electronic device 210 or the second electronic device 220) may log in to the exercise machine 400 on the basis of a unique device ID generated by the electronic device 300.

When the electronic device 300 is connected to the exercise machine 400 in operation 3802, the electronic device 300 may make a request for manufacturer information of the exercise machine 400 in operation 3804.

In operation 3806, the electronic device 300 may receive manufacturer information from the exercise machine 400, and the electronic device 300 may generate the device ID on the basis of the manufacturer information received from the exercise machine 400 and unique identification information of the electronic device 300. According to various embodiments, the device ID may be generated for each manufacturer or generated regardless of a manufacturer. In operation 3808, the electronic device 300 may transmit the generated device ID to the exercise machine 400.

In operation 3810, the exercise machine 400 may make a request for performing login with the device ID received from the electronic device 300 to the fitness server 260.

In operation 3812, the fitness server 260 may identify whether the device ID received from the exercise machine 400 is registered.

When the device ID received from the exercise machine 400 is a registered ID on the basis of the identification result, the fitness server 260 may process the login and inform the exercise machine 400 of the login success result in operation 3814. In operation 3816, the exercise machine 400 may receive the login success result from the fitness server 260 and inform the electronic device 300 of the login success result.

Figure 39:
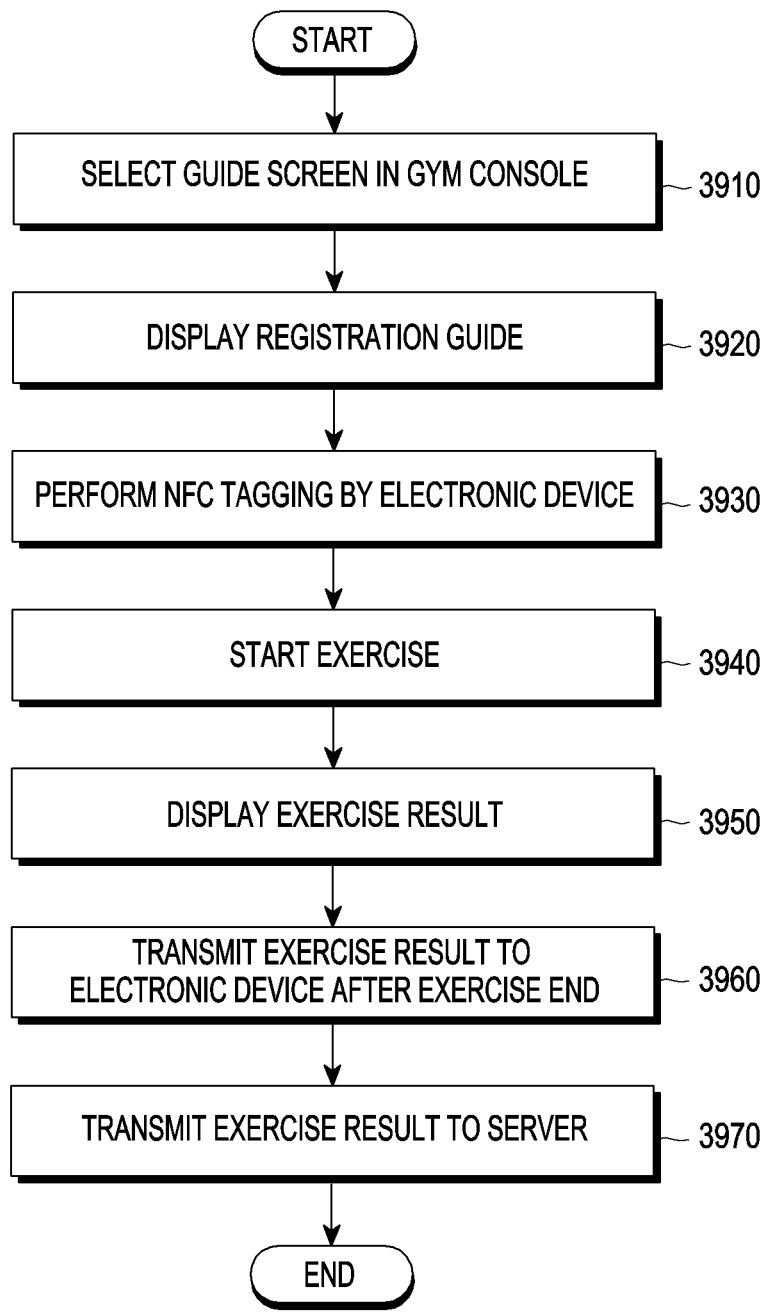
FIG. 39 is a flowchart illustrating a login operation through a console of an electronic device according to an embodiment of the disclosure.

FIG. 39 is a flowchart illustrating a login operation through a console of an electronic device according to an embodiment of the disclosure.

Referring to FIG. 39, it is possible to induce a user linked to the exercise machine to perform anonymous login.

The electronic device 300 may anonymously log in to the exercise machine 400 and may be linked thereto for an exercise. The electronic device 300 may determine that the currently used exercise machine 400 is anonymously linked and transmit corresponding information to the fitness server 260. Thereafter, it is possible to transmit the corresponding information to the electronic device 300 (for example, the first electronic device 210 or the second electronic device 220) for the user who anonymously logged in on the basis of information stored in the fitness server 260 and induce the login. According to various embodiments, a method of inducing the login may be performed through the console of the exercise machine 400 or performed through transmission of login linking connection information using an SMS or IM message channel.

Referring to FIG. 39, when the user selects a guide screen in a GYM console in operation 3910, a registration guide may be displayed on the display in operation 3920. The user may NFC-tag the electronic device 300 on the exercise machine 400 in operation 3930 and start an exercise in operation 3940.

The exercise machine 400 may display an exercise result on the display in operation 3950 and transmit the exercise result to the electronic device 300 after the exercise ends in operation 3960. In operation 3970, the electronic device 300 may transmit the exercise result to the fitness server 260.

Figure 40:
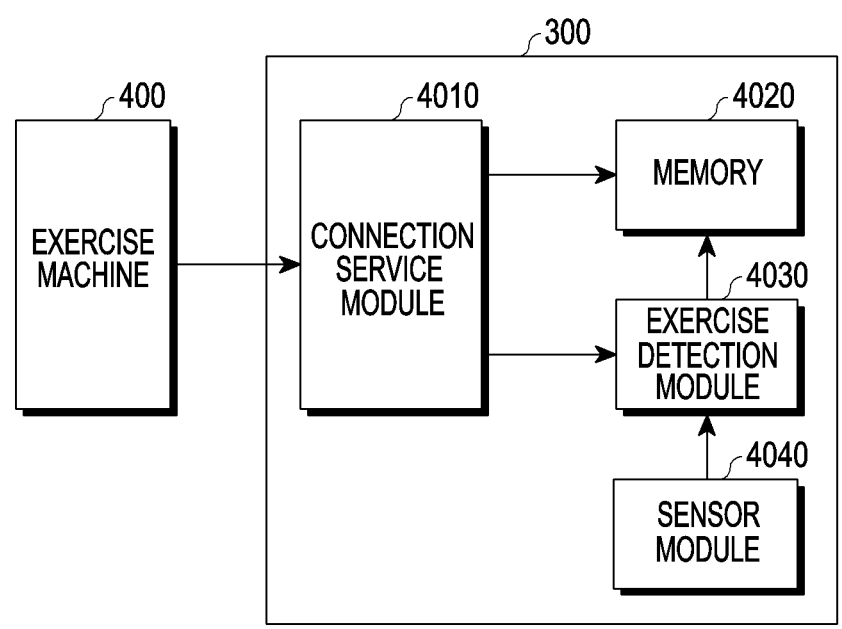
FIG. 40 illustrates a method of processing data on the basis of context information by an electronic device according to an embodiment of the disclosure.

FIG. 40 illustrates a method of processing data on the basis of context information by an electronic device according to an embodiment of the disclosure.

According to various embodiments, when the user does an exercise using the exercise machine 400 and stops the exercise in the state in which the exercise machine 400 is operating, the electronic device 300 (for example, the second electronic device 220) may classify the state as an interval in which no exercise is done on the basis of measured heart rate data. According to various embodiments, the exercise machine 400 and the electronic device 300 may verify data on each other on the basis of data which can be mutually measured by each other.

Referring to FIG. 40, the exercise machine 400 may transmit exercise information to the electronic device 300 in real time. A connection service module 4010 of the electronic device 300 may extract an exercise type, a state of the exercise machine, and exercise data through data received from the exercise machine 400, provide the same to an exercise determination module 4020, and provide the exercise type to an exercise detection module 4030.

According to various embodiments, information measured by a sensor module 4040 may be transmitted to the exercise detection module 4030. The exercise detection module 4030 may transmit data (for example, an HR, a speed, and a slope) measured on the basis of exercise type information received from the connection service module 4010 and sensing information received from the sensor module 4040 to the exercise determination module 4020. The exercise determination module 4020 may collect the information received from the connection service module 4010 and the exercise detection module 4030 and determine whether the user normally exercises through the exercise machine 400 at present.

According to various embodiments, in the case of the exercise machine 400 that directly operates according to a setting value such as a treadmill or a stepper, if the actual user does exercise, a setting value (speed or cadence) provided by the treadmill is accurate. However, when the user comes down from the exercise machine for other business for a moment while maintaining the setting or stops in an area of the exercise machine 400 that does not operate, a value measured by the electronic device 300 (for example, the second electronic device 220) worn on the user may be more accurate than a value transmitted from the exercise machine 400. Accordingly, when the user is exercising through a link with the exercise machine 400, both a value acquired through the exercise machine 400 and a value measured by the electronic device 300 may be identified and thus an exercise state of the user may be more accurately stored.

According to various embodiments, it may be identified whether an action corresponding to an exercise type of the current exercise continues through the electronic device 300, and when it is determined that the corresponding exercise does not continue for a predetermined period, the electronic device 300 may determine that the value received from the exercise machine 400 is not valid and exclude the value from a final exercise record. According to various embodiments, continuance of the corresponding exercise may be determined through detection of a pattern or movement or using pattern mismatching between biometric information such as a heart rate or blood pressure and information of the machine.

Since an acceptable level of the exercise varies depending on individual capability or a condition on the day, it is important to detect the current body condition and exercise according thereto. According to various embodiments, when a sensor suitable for the exercise type is driven and it is determined that the current exercise is not sufficient compared to the current body condition, it is possible to coach the user for increasing a speed or a weight through the display of the electronic device 300. When a heart rate is too fast, it is possible to provide a guide to control an exercise level. Further, the electronic device 300 may recommend a next exercise by analyzing the exercise result.

Each of the elements described in this document may consist of one or more components, and the names of the corresponding elements may vary depending on the type of electronic device. The electronic device according to various embodiments of the disclosure may include at least one of the aforementioned elements. Some elements may be omitted or other additional elements may be further included in the electronic device. Also, some of the hardware components according to various embodiments may be combined into one entity, which may perform functions identical to those of the relevant components before the combination.

The term "module" used in the disclosure may refer to, for example, a unit including a combination of one or more of hardware, software, and firmware. The "module" may be interchangeable with a term, such as unit, logic, logical block, component, or circuit. The "module" may be a minimum unit of an integrally configured article or a part thereof. The "module" may be a minimum unit performing one or more functions or a part thereof. The "module" may be mechanically or electronically implemented. For example, the "module" may include at least one of an Application-Specific Integrated Circuit (ASIC) chip, a Field-Programmable Gate Arrays (FPGAs), and a programmable-logic device for performing operations which have been already known or are to be developed in the future.

At least some of the devices (for example, modules or functions thereof) or the method (for example, operations) according to various embodiments may be implemented by an instruction stored in a computer-readable storage medium in a programming module form. When the instruction is executed by a processor (for example, the processor 120), one or more processors may perform a function corresponding to the instruction. A computer-readable storage medium may be, for example, the memory 130.

The program may be included in the computer readable storage medium such as a hard disk, a floppy disk, magnetic media (for example, a magnetic tape), optical media (for example, a Compact Disc Read Only Memory (CD-ROM) and a Digital Versatile Disc (DVD)), magneto-optical media (for example, a floptical disk), a hardware device (for example, a Read Only Memory (ROM), a Random Access Memory (RAM), a flash memory), and the like. In addition, the program instructions may include high class language codes, which can be executed in a computer by using an interpreter, as well as machine codes made by a compiler. The hardware device may operate as one or more software modules to perform the operation according to various embodiments, and vice versa.

A module or a program module according to various embodiments may include one or more of the aforementioned elements, omit some thereof, or further include additional other elements. The operations performed by the module, the program module, or other elements according to various embodiments may be performed by a sequential, parallel, repetitive, or heuristic method. Further, some operations may be executed according to another order or may be omitted, or other operations may be added.

While the disclosure has been shown and described with reference to various embodiments thereof, it will be understood by those skilled in the art that various changes in form and details may be made therein without departing from the spirt and the scope of the disclosure as defined by the appended claims and their equivalents.

What is claimed is:

1. An electronic device comprising:
at least one communication circuitry;
a display;
a processor operatively connected to the at least one communication circuitry and the display; and
a memory operatively connected to the processor,
wherein the memory is configured to store instructions, that when executed,
cause the processor to:
   make a connection with at least one external electronic device through the at least one communication circuitry,
   identify first exercise-related information of a first user measured during a first time interval, based on information received from the at least one external electronic device,
   identify second exercise-related information of the first user measured during a second time interval after the first time interval, based on information received from the at least one external electronic device,
   in response to a determination that the identified first exercise-related information and the identified second exercise-related information are information on a correlated exercise, based on a configured reference, merge the identified first exercise-related information and the identified second exercise-related information as one continuous exercise and display the merged first and second exercise-related information as the one continuous exercise through the display, and
   in response to a determination that the identified first exercise-related information and the identified second exercise-related information are not information on the correlated exercise, based on the configured reference, display the identified first exercise-related information and the identified second exercise-related information separately through the display,
   wherein the configured reference comprises at least one of a type of an exercise machine, location information, or environment information corresponding to each of the first and second time intervals, and
   wherein the at least one external electronic device is an exercise machine comprising at least one short-range communication circuitry.

2. The electronic device of claim 1, wherein the merged first and second exercise-related information displayed as the one continuous exercise is transmitted to a second electronic device through the at least one communication circuitry.

3. The electronic device of claim 1, wherein the instructions, when executed, further cause the processor to:

make the connection with the at least one external electronic device through a first communication circuitry and transmit connection information for sharing data,
make the connection with the at least one external electronic device through a second communication circuitry, based on the connection information for sharing data, and
transmit and receive exercise-related information to and from the at least one external electronic device through the second communication circuitry.

4. The electronic device of claim 3, wherein the connection information for sharing data comprises at least one of a bluetooth low energy (BLE) address, a local name, or a user account.

5. The electronic device of claim 1, wherein the instructions, when executed, further cause the processor to:
transmit user account information to the at least one external electronic device through the at least one communication circuitry, and
receive a login result from the at least one external electronic device.

6. The electronic device of claim 1, further comprising:
at least one sensor,
wherein the instructions, when executed, further cause the processor to:
receive information related to an exercise type from the at least one external electronic device when the connection with the at least one external electronic device is made through the at least one communication circuitry, and
drive a preset sensor among the at least one sensor, based on the received information related to the exercise type.

7. The electronic device of claim 1, wherein the at least one external electronic device is an exercise machine comprising at least one short-range communication circuitry.

8. An electronic device comprising:
at least one communication circuitry;
a display;
at least one sensor;
a processor operatively connected to the at least one communication circuitry, the display, and the at least one sensor; and
a memory configured to store instruction, the memory operatively connected to the processor,
wherein the instructions stored in the memory, when executed, cause the processor to:
store first exercise-related information of a first user in the memory,
based on information measured during a first time interval by the at least one sensor, make a connection with at least one external electronic device through the at least one communication circuitry,
identify second exercise-related information of the first user measured during a second time interval after the first time interval, based on information received from the at least one external electronic device,
in response to a determination that the stored first exercise-related information and the identified second exercise-related information are information on a correlated exercise, based on a configured reference, merge the stored first exercise-related information and the identified second exercise-related information as one continuous exercise and display the merged first and second exercise-related information as the one continuous exercise through the display, and
in response to a determination that the stored first exercise-related information and the identified second exercise-related information are not information on the correlated exercise, based on the configured reference, display the stored first exercise-related information and the identified second exercise-related information separately through the display,
wherein the configured reference comprises at least one of a type of an exercise machine, location information, or environment information corresponding to each of the first and second time intervals, and
wherein the at least one external electronic device is an exercise machine comprising at least one short-range communication circuitry.

9. The electronic device of claim 8, wherein the instructions, when executed, further cause the processor to:
make the connection with the at least one external electronic device through a first communication circuitry and transmit connection information for sharing data,
make the connection with the at least one external electronic device through a second communication circuitry, based on the connection information for sharing data, and
transmit and receive exercise-related information to and from the at least one external electronic device through the second communication circuitry.

10. The electronic device of claim 9, wherein the connection information for sharing data comprises at least one of a bluetooth low energy (BLE) address, a local name, or a user account.

11. The electronic device of claim 8, wherein the instructions, when executed, further cause the processor to:
transmit user account information to the at least one external electronic device through the at least one communication circuitry, and
receive a login result from the at least one external electronic device.

12. The electronic device of claim 8, wherein the instructions, when executed, further cause the processor to:
receive information related to an exercise type from the at least one external electronic device when the connection with the at least one external electronic device is made through the at least one communication circuitry, and
drive a preset sensor among the at least one sensor, based on the received information related to the exercise type.

13. The electronic device of claim 8, wherein the at least one external electronic device is an exercise machine comprising at least one short-range communication circuitry.

14. An electronic device comprising:
at least one communication circuitry;
a display;
at least one sensor;
a processor operatively connected to the at least one communication circuitry, the display, and the at least one sensor; and
a memory configured to store instructions, the memory operatively connected to the processor,
wherein the instructions stored in the memory, when executed, cause the processor to:
make a connection with at least one external electronic device through the at least one communication circuitry,
store first exercise-related information of a first user measured during a first time interval in the memory, based on information received from the at least one external electronic device, store second exercise-related information of the first user in the memory, based on information measured during a second time interval after the first time interval by the at least one sensor, and in response to a determination that the stored first exercise-related information and the stored second exercise-related information are information on a correlated exercise, based on a configured reference, merge the first exercise-related information and the second exercise-related information as one continuous exercise and display the merged first and second exercise-related information as the one continuous exercise through the display, and in response to a determination that the stored first exercise-related information and the stored second exercise-related information are not information on the correlated exercise, based on the configured reference, display the stored first exercise-related information and the stored second exercise-related information separately through the display, wherein the configured reference comprises at least one of a type of an exercise machine, location information, or environment information corresponding to each of the first and second time intervals.

15. The electronic device of claim 14, wherein the instructions, when executed, further cause the processor to:
make the connection with the at least one external electronic device through a first communication circuitry and transmit connection information for sharing data,
make the connection with the at least one external electronic device through a second communication circuitry, based on the connection information for sharing data, and
transmit and receive exercise-related information to and from the at least one external electronic device through the second communication circuitry.

16. The electronic device of claim 15, wherein the connection information for sharing data includes at least one of a bluetooth low energy (BLE) address, a local name, or a user account.

17. The electronic device of claim 14, wherein the instructions, when executed, further cause the processor to:
transmit user account information to the at least one external electronic device through the at least one communication circuitry, and
receive a login result from the at least one external electronic device.

18. The electronic device of claim 14, wherein the instructions, when executed, further cause the processor to determine the correlated exercise based on the at least one external electronic device being located within a gymnasium.

19. The electronic device of claim 18, wherein the instructions, when executed, further cause the processor to determine that the at least one external electronic device is located within the gymnasium, by determining a number of the at least one external electronic device being greater than a predetermined number.

20. The electronic device of claim 19, wherein the instructions, when executed, further cause the processor to determine that the at least one external electronic device is located within the gymnasium, by detecting a checkin of a location corresponding to the gymnasium.

21. The electronic device of claim 14, wherein the at least one external electronic device is an exercise machine comprising at least one short-range communication circuitry.

* * * * *